US008568399B2

(12) United States Patent
Azamian et al.

(10) Patent No.: US 8,568,399 B2
(45) Date of Patent: Oct. 29, 2013

(54) METHODS FOR THERMALLY-INDUCED HEPATIC NEUROMODULATION

(71) Applicant: Metavention, Inc., Newport Beach, CA (US)

(72) Inventors: Bobak Robert Azamian, Newport Coast, CA (US); Scott Bradley Vafai, Boston, MA (US); Jonathan Allen Coe, Menlo Park, CA (US)

(73) Assignee: Metavention, Inc., Newport Beach, CA (US)

( * ) Notice: Subject to any disclaimer, the term of this patent is extended or adjusted under 35 U.S.C. 154(b) by 0 days.

(21) Appl. No.: 13/789,521

(22) Filed: Mar. 7, 2013

(65) Prior Publication Data
US 2013/0178910 A1 Jul. 11, 2013

Related U.S. Application Data

(63) Continuation of application No. PCT/US2012/068630, filed on Dec. 7, 2012.

(60) Provisional application No. 61/568,843, filed on Dec. 9, 2011.

(51) Int. Cl.
*A61B 18/18* (2006.01)

(52) U.S. Cl.
USPC .............................................. 606/33; 606/41

(58) Field of Classification Search
USPC ........................................ 606/32–45; 607/42
See application file for complete search history.

(56) References Cited

U.S. PATENT DOCUMENTS

| 4,033,331 | A  | 7/1977  | Guss et al.     |
| 5,561,165 | A  | 10/1996 | Lautt et al.    |
| 6,113,593 | A  | 9/2000  | Tu et al.       |
| 6,451,011 | B2 | 9/2002  | Tu et al.       |
| 6,832,114 | B1 | 12/2004 | Whitehurst et al. |
| 6,885,888 | B2 | 4/2005  | Rezai           |
| 6,936,047 | B2 | 8/2005  | Nasab et al.    |
| 6,978,174 | B2 | 12/2005 | Gelfand et al.  |

(Continued)

FOREIGN PATENT DOCUMENTS

| RU | 2277381 | 6/2006 |
| RU | 2421163 | 6/2011 |

(Continued)

OTHER PUBLICATIONS

Van Den Hoek, Anita M. et al., "Intracerebroventricular Administration of Neuropeptide Y Induces Hepatic Insulin Resistance via Sympathetic Innervation," Diabetes, vol. 57, pp. 2304-2310 (Sep. 2008).

(Continued)

*Primary Examiner* — Linda Dvorak
*Assistant Examiner* — Amanda Scott
(74) *Attorney, Agent, or Firm* — Knobbe, Martens, Olson & Bear LLP

(57) ABSTRACT

According to some embodiments, a method of treating a subject having diabetes or symptoms associated with diabetes is provided. The method includes delivering a neuromodulation catheter within a vessel (e.g., hepatic artery) having surrounding nerves that innervate the liver (e.g., sympathetic nerves of the hepatic plexus). The method may also include modulating (e.g., disrupting, ablating, stimulating) the nerves by mechanical compression, energy delivery, or fluid delivery.

69 Claims, 25 Drawing Sheets

(56) References Cited

U.S. PATENT DOCUMENTS

| | | |
|---|---|---|
| 7,048,716 B1 | 5/2006 | Kucharczyk et al. |
| 7,149,574 B2 | 12/2006 | Yun et al. |
| 7,162,303 B2 | 1/2007 | Levin et al. |
| 7,363,076 B2 | 4/2008 | Yun et al. |
| 7,477,945 B2 | 1/2009 | Rezai et al. |
| 7,510,536 B2 | 3/2009 | Foley et al. |
| 7,529,582 B1 | 5/2009 | DiLorenzo |
| 7,599,736 B2 | 10/2009 | DiLorenzo |
| 7,599,737 B2 | 10/2009 | Yomtov et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,655,006 B2 * | 2/2010 | Sauvageau et al. ............ 606/41 |
| 7,689,276 B2 | 3/2010 | Dobak |
| 7,689,277 B2 | 3/2010 | Dobak, III |
| 7,702,386 B2 | 4/2010 | Dobak et al. |
| 7,717,948 B2 | 5/2010 | Demarais et al. |
| 7,738,952 B2 | 6/2010 | Yun et al. |
| 7,756,583 B2 | 7/2010 | Demarais et al. |
| 7,778,704 B2 | 8/2010 | Rezai |
| 7,831,308 B2 | 11/2010 | Rezai et al. |
| 7,853,333 B2 | 12/2010 | Demarais |
| 7,865,237 B2 | 1/2011 | Machado et al. |
| 7,873,417 B2 | 1/2011 | Demarais et al. |
| 7,877,146 B2 | 1/2011 | Rezai |
| 7,881,784 B2 | 2/2011 | Pasricha et al. |
| 7,937,143 B2 | 5/2011 | Demarais et al. |
| 7,937,145 B2 | 5/2011 | Dobak |
| 7,963,287 B2 | 6/2011 | Lanphere et al. |
| RE42,961 E | 11/2011 | Rahme |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,299 B2 | 3/2012 | Dobak, III |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,172,693 B1 | 5/2012 | Guerzini et al. |
| 8,175,711 B2 | 5/2012 | Demarais et al. |
| 8,197,409 B2 | 6/2012 | Foley et al. |
| 8,277,398 B2 | 10/2012 | Weng et al. |
| 8,295,912 B2 | 10/2012 | Gertner |
| 8,372,009 B2 | 2/2013 | Emery et al. |
| 8,374,674 B2 | 2/2013 | Gertner |
| 2003/0065371 A1 * | 4/2003 | Satake ........................ 607/102 |
| 2005/0049293 A1 | 3/2005 | Lautt |
| 2005/0288730 A1 | 12/2005 | Deem et al. |
| 2006/0025821 A1 | 2/2006 | Gelfand et al. |
| 2006/0111704 A1 | 5/2006 | Brenneman et al. |
| 2006/0167498 A1 | 7/2006 | DiLorenzo |
| 2006/0212076 A1 | 9/2006 | Demarais et al. |
| 2006/0265014 A1 | 11/2006 | Demarais et al. |
| 2006/0271111 A1 | 11/2006 | Demarais et al. |
| 2007/0060971 A1 * | 3/2007 | Glasberg et al. ................ 607/40 |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2008/0213331 A1 | 9/2008 | Gelfand et al. |
| 2008/0255642 A1 | 10/2008 | Zarins et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0118777 A1 | 5/2009 | Iki et al. |
| 2009/0118780 A1 | 5/2009 | DiLorenzo |
| 2009/0324701 A1 | 12/2009 | Williams |
| 2010/0010567 A1 | 1/2010 | Deem et al. |
| 2010/0057161 A1 | 3/2010 | Machado et al. |
| 2010/0106207 A1 | 4/2010 | Dobak, III |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0249773 A1 | 9/2010 | Clark et al. |
| 2010/0249859 A1 | 9/2010 | DiLorenzo |
| 2010/0268307 A1 | 10/2010 | Demarais et al. |
| 2010/0286684 A1 | 11/2010 | Hata et al. |
| 2011/0029037 A1 | 2/2011 | Rezai et al. |
| 2011/0060324 A1 | 3/2011 | Wu et al. |
| 2011/0098762 A1 | 4/2011 | Rezai |
| 2011/0112400 A1 | 5/2011 | Emery et al. |
| 2011/0118726 A1 | 5/2011 | De La Rama et al. |
| 2011/0118747 A1 | 5/2011 | Pasricha et al. |
| 2011/0118812 A1 | 5/2011 | Pasricha et al. |
| 2011/0137298 A1 | 6/2011 | Nguyen et al. |
| 2011/0152974 A1 | 6/2011 | Rezai et al. |
| 2011/0160514 A1 | 6/2011 | Long et al. |
| 2011/0166499 A1 | 7/2011 | Demarais et al. |
| 2011/0168739 A1 | 7/2011 | Brouwer |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0208173 A1 | 8/2011 | Sobotka et al. |
| 2011/0208175 A1 | 8/2011 | Sobotka et al. |
| 2011/0230939 A1 | 9/2011 | Weinstock |
| 2011/0257523 A1 | 10/2011 | Hastings et al. |
| 2011/0257562 A1 | 10/2011 | Schaer |
| 2011/0257564 A1 | 10/2011 | Demarais et al. |
| 2011/0257641 A1 | 10/2011 | Hastings et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0301664 A1 | 12/2011 | Rezai |
| 2011/0306851 A1 | 12/2011 | Wang |
| 2011/0307034 A1 | 12/2011 | Hastings et al. |
| 2011/0313417 A1 | 12/2011 | De La Rama et al. |
| 2012/0089047 A1 | 4/2012 | Ryba et al. |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0158104 A1 | 6/2012 | Huynh et al. |
| 2012/0253239 A1 | 10/2012 | Gertner et al. |
| 2012/0271302 A1 | 10/2012 | Behl et al. |
| 2013/0035681 A1 | 2/2013 | Subramaniam et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0110106 A1 | 5/2013 | Richardson |

FOREIGN PATENT DOCUMENTS

| | | |
|---|---|---|
| WO | WO 2007/018788 | 2/2007 |
| WO | WO 2009/090440 | 7/2009 |

(56) References Cited

FOREIGN PATENT DOCUMENTS

| WO | WO 2010/111400 | 9/2010 |
|---|---|---|
| WO | WO 2011/046880 | 4/2011 |
| WO | WO 2012/019156 | 2/2012 |
| WO | WO 2012/025245 | 3/2012 |
| WO | WO 2012/025246 | 3/2012 |

OTHER PUBLICATIONS

DiCostanzo, Catherine A. et al., "Role of the Hepatic Sympathetic Nerves in the Regulation of Net Hepatic Glucose Uptake and the Mediation of the Portal Glucose Signal," American Journal of Physiology—Endocrinology and Metabolism, vol. 290, pp. E9-E16 (Aug. 16, 2005).

Yi, Chun-Xia et al., "The role of the autonomic nervous liver innervation in the control of energy metabolism," Biochimica et Biophysica Acta vol. 1802 (2010), pp. 416-431.

Loukas, Marios et al., "A Review of the Thoracic Splanchnic Nerves and Celiac Ganglia," Clinical Anatomy, vol. 23, pp. 512-522 (2010).

Yi, Chun-Xia et al., << A Major Role for Perifonical Orexin Neurons in the Control of Glucose Metabolism in Rats, >> Diabetes, vol. 58, Sep. 2009, pp. 1998-2005.

Tavares, Fabio Luis et al., << Hepatic denervation impairs the assembly and secretion of VLDL-TAG, >> Cell Biochemistry and Function, vol. 26, pp. 557-565 (2008).

Adkins-Marshall, B. et al., << Role of hepatic nerves in response of liver to intraportal glucose delivery in dogs, American Journal of Physiology—Endocrinology and Metabolism, vol. 262, pp. E679-E686 (1992).

Bruinstroop, Eveline et al., "Hypothalamic neuropeptide Y (NPY) controls hepatic VLDL-triglyceride secretion in rats via the sympathetic nervous system," Diabetes, vol. 61(5), pp. 1043-1050 (May 2012).

Buijs, Ruud M. et al., << The Suprachiasmatic Nucleus Balances Sympathetic and Parasympathetic Output to Peripheral Organs through Separate Preautonomic Neurons, Journal of Comparative Neurology, vol. 464, pp. 36-48 (2003).

Cailotto, Cathy et al., "The suprachiasmatic nucleus controls the daily variation of plasma glucose via the autonomic output to the liver: are the clock genes involved?" European Journal of Neuroscience, vol. 22, pp. 2531-2540 (2005).

Cardin, Sylvain et al., "Effect of hepatic vagotomy on hormonal response to exercise in gluconeogenesis-inhibited rats," American Journal of Physiology—Regulatory Integrative Comparative Physiology, vol. 260, pp. R67-R72 (1991).

Cardin, Sylvain et al., "Involvement of the vagus nerves in the regulation of basal hepatic glucose production in conscious dogs," American Journal of Physiology—Endocrinology and Metabolism, vol. 283, pp. E958-E964 (2002).

Jackson, Patricia A., "Effect of hepatic denervation on the counterregulatory response to insulin-induced hypoglycemia in the dog," American Journal of Physiology—Endocrinology and Metabolism, vol. 279, pp. E1249-E1257 (2000).

Wada, Masahiko et al., "Hepatic denervation does not significantly change the response of the liver to glucagon in conscious dogs," American Journal of Physiology—Endocrinology and Metabolism, vol. 268, pp. E194-E203 (1995).

Moore, Mary Courtney et al., "Effect of hepatic denervation on peripheral insulin sensitivity in conscious dogs," American Journal of Physiology—Endocrinology and Metabolism, vol. 282, pp. E286-E296 (2002).

Moore, Mary Courtney et al., "Chronic hepatic artery ligation does not prevent liver from differentiating portal vs. peripheral glucose delivery," American Journal of Physiology—Endocrinology and Metabolism, vol. 285, pp. E845-853 (2003).

Kalsbeek, Andries et al., "Suprachiasmatic GABAergic Inputs to the Paraventricular Nucleus Control Plasma Glucose Concentrations in the Rat via Sympathetic Innervation of the Liver," Journal of Neuroscience, vol. 24(35) pp. 7604-7613 (2004).

Kalsbeek, A. et al., "Hypothalamic control of energy metabolism via the autonomic nervous system," Annals of the New York Academy of Sciences, vol. 1212, pp. 114-129 (2010).

Klieverik, Lars P. et al., "Thyroid hormone modulates glucose production via a sympathetic pathway from the hypothalamic paraventricular nucleus to the liver," PNAS, vol. 106 (14), pp. 5966-5971 (2009).

Klieverik, Lars P. et al., "Effects of thyrotoxicosis and selective hepatic autonomic denervation on hepatic glucose metabolism in rats," American Journal of Physiology—Endocrinology and Metabolism, vol. 294, pp. E513-E520 (2008).

Lindfeldt, J. et al., "Hepatic sympathetic denervation potentiates glucagon-stimulated glycogenolysis and hyperinsulinaemia in the rat," Journal of the Autonomic Nervous System, vol. 19, pp. 211-217 (1987).

Wiersma, Mariska M.L. et al., Effect of liver denervation on glucose production during running in guinea pigs, >>American Journal of Physiology—Regulatory Integrative Comparative Physiology, vol. 268, pp. R72-R77 (1995).

Pocai, Alessasndro et al., "Hypothalamic $K_{ATP}$ channels control hepatic glucose production," Nature, vol. 434, pp. 1026-1031 (2005).

Uno, Kenji et al., << Neuronal Pathway from the Liver Modulates Energy Expenditure and Systemic Insulin Sensitivity, Science, vol. 312, pp. 1656-1659 (Jun. 16, 2006).

Xie, Hongheng et al., "Insulin resistance of skeletal muscle produced by hepatic parasympathetic interruption," American Journal of Physiology—Endocrinology and Metabolism, vol. 270, pp. E858-E863 (1996).

Yi, Chun-Xia et al., << Pituitary Adenylate Cyclase-Activating Polypeptide Stimulates Glucose Production via the Hepatic Sympathetic Innervation in Rats, >> Diabetes, vol. 59, pp. 1591-1600 (Jul. 2010).

Berthoud, H.R. et al., << Evidence for a role of the gastric, coeliac and hepatic branches in vagally stimulated insulin secretion in the rat, Journal of the Autonomic Nervous System, vol. 7, pp. 97-110 (1983).

Chen, J. et al., "Hepatic electrical stimulation reduces blood glucose in diabetic rats," Neurogastroeneterology & Motility vol. 22, pp. 1109-e286 (2010).

Niijima, Akira, "Glucose-Sensitive Afferent Nerve Fibres in the Hepatic Branch of the Vagus Nerve in the Guinea-Pig," Journal of Physiology, vol. 322, pp. 315-323 (1982).

Lautt, W. Wayne et al., "Hepatic glucose balance in response to direct stiumulation of sympathetic nerves in the intact liver of cats," Canadian Journal of Physiology and Pharmacology, vol. 56, pp. 1022-1028 (1978).

Lautt, W. Wayne et al., "Hepatic parasympathetic neural effect on glucose balance in the intact liver," Canadian Journal of Physiology and Phramacology, vol. 56, pp. 679-682 (1978).

Nobin, A. et al., "Organization and Function of the Sympathetic Innervation of Human Liver," Acta Physiologica Scandinavia Suppl., vol. 452, pp. 103-106 (1977).

Stiimpel, F., "Loss of regulation by sympathetic hepatic nerves of liver metabolism and haemodynamics in chronically streptozotocin-diabetic rats," Diabetologia, vol. 39, pp. 161-165 (1996).

Takahashi, Akira, "Effects of hepatic nerve stimulation on blood glucose and glycogenolysis in rat liver: Studies with in vivo microdialysis," Journal of the Autonomic Nervous System, vol. 61, pp. 181-185 (1996).

Atherton, Daniel S. et al., << Micro-anatomy of the Renal Sympathetic Nervous System : A Human Postmortem Histologic Study, >> Clinical Anatomy, vol. 25, pp. 628-633 (2012).

Rippy, Marian K. et al., << Catheter-based renal sympathetic denervation: chronic preclinical evidence for renal artery safety, >> Clinical Research in Cardiology, vol. 100, pp. 1095-1101 (2011).

Davies, Justin E. et al., << First-in-man safety evaluation of renal denervation for chronic systolic heart failure : Primary outcome from REACH-Pilot study, >> International Journal of Cardiology (2012).

Brandt, Mathias C. et al., << Renal Sympathetic Denervation Reduces Left Ventricular Hypertrophy and Improves Cardiac Function in Patients With Resistant Hypertension, >> Journal of the American College of Cardiology, vol. 59, No. 10, pp. 901-909 (2012).

(56) References Cited

OTHER PUBLICATIONS

Schlaich, Markus P. et al., "Renal Denervation in Human Hypertension: Mechanisms, Current Findings, and Future Prospects," Current Hypertension Reports, vol. 14, pp. 247-253 (2012).
Mahfoud, Felix et al., "Effect of Renal Sympathetic Denervation on Glucose Metabolism in Patients With Resistant Hypertension: A Pilot Study," Circulation, vol. 123, pp. 1940-1946 (Apr. 25, 2011).
Steigerwald, Kristin et al. "Morphological assessment of renal arteries after radiofrequency catheter-based sympathetic denervation in a porcine model," Journal of Hypertension, vol. 30, No. 1, pp. 1-10 (2012).
Schlaich, Markus P. et al., "Renal denervation: A potential new treatment modality for polycystic ovary syndrome?" Journal of Hypertension, vol. 29, pp. 991-996 (2011).
Schlaich, Markus P. et al., "Renal Sympathetic Nerve Ablation: The New Frontier in the Treatment of Hypertension," Current Hypertension Reports, vol. 12, pp. 39-46 (2010).
Schlaich, Markus P. et al., "Renal Sympathetic-Nerve Ablation for Uncontrolled Hypertension," New England Journal of Medicine, vol. 361, No. 9, pp. 932-934 (Aug. 27, 2009).
Thompson, Mary et al., "Renal Denervation Sparks Device Market Gold Rush," Elsevier Business Intelligence, Medtech Insight, vol. 24, No. 5 (May 2012).
Witkowski, Adam et al., "Effects of Renal Sympathetic Denervation on Blood Pressure, Sleep Apnea Course, and Glycemic Control in Patients With Resistant Hypertension and Sleep Apnea," Journal of Hypertension, vol. 58, pp. 559-565 (2011).
Zile, Michael R. et al., << Effects of Autonomic Modulation, >> Journal of the American College of Cardiology, vol. 59, No. 10, pp. 910-912 (2012).
King, Andrew J., "Splanchnic Circulation is a Critical Neural Target in Angiotensin II Salt Hypertension in Rats," Journal of Hypertension, vol. 50, pp. 547-556 (2007).
Anderson, Erling A. et al, "Hyperinsulinemia Produces both Sympathetic Neural Activation and Vasodilation in Normal Humans," Journal of Clinical Investigation, vol. 87, pp. 2246-2252 (1991).
Bruce, D.G. et al., << The effects of sympathetic nervous system activation and psychological stress on glucose metabolism and blood pressure in subjects with Type 2 (non-insulin-dependent) diabetes mellitus, Diabetologia, vol. 35, pp. 835-843 (1992).
Carnethon, Mercedes R. et al., << Prospective Investigation of Autonomic Nervous System Function and the Development of Type 2 Diabetes, >> Circulation, vol. 107, pp. 2190-2195 (2003).
Coker, Robert H. et al., << Glucoregulation During Exercise : The Role of the Neuroendocrine System, >> Sports Medicine, vol. 35, No. 7, pp. 575-583 (2005).
Flaa Arnljot et al., "Increased sympathetic reactivity may predict insulin resistance: An 18-year follow-up study," Metabolism Clinical and Experimental, vol. 57, pp. 1422-1427 (2008).
Grassi, G. et al., "Neuroadrenergic and reflex abnormalities in patients with metabolic syndrome," Diabetologia, vol. 48, pp. 1359-1365 (2005).
Haque, Mohammad Shahidul et al, "Role of the Sympathetic Nervous System and Insulin in Enhancing Glucose Uptake in Peripheral Tissues After Intrahypothalamic Injection of Leptin in Rats," Diabetes, vol. 48, pp. 1706-1712 (1999).
Lambert, Gavin W. et al., "Sympathetic Nervous Activation in Obesity and the Metabolic Syndrome—Causes, consequences and therapeutic implications," Pharmacology & Therapeutics, vol. 126, pp. 159-172 (2010).
Licht, Carmilla M. M. et al., << Increased Sympathetic and Decreased Parasympathetic Activity Rather Than Changes in Hypothalamic-Pituitary-Adrenal Axis Activity is Associated with Metabolic Abnormalities, Journal of Clinical Endocrinology and Metabolism, vol. 95, No. 5, pp. 2458-2466 (2010).
Mancia, Giuseppe et al., "The sympathetic nervous system and the metabolic syndrome," Journal of Hypertension, vol. 25, No. 5, pp. 909-920 (2007).
Nonogaki, K., "New insights into sympathetic regulation of glucose and fat metabolism," Diabetologia, vol. 43, pp. 533-549 (2000).
Straznicky, Nora E. et al., << Neuroadrenergic Dysfunction Along the Diabetes Continuum: A Comparative Study in Obese Metabolic Syndrome Subjects, >> Diabetes, vol. 61, pp. 2506-2516 (2012).
Takahashi, Kanji A. et al., << Fasting Induces a Large, Leptin-Dependent Increase in the Intrinsic Action Potential Frequency of Orexigenic Arcuate Nucleus NeuropeptideY/Agouti-Related Protein Neurons, >> Endocrinology, vol. 146, No. 3, pp. 1043-1047 (2005).
Tentolouris, N. et al., "Sympathetic System Activity in Obesity and Metabolic Syndrome," Annals New York Academy of Sciences, vol. 1083, pp. 129-152 (2006).
Tentolouris, Nicholas et al., Perturbed Autonomic Nervous System Function in Metabolic Syndrome, Neuromolecular Medicine, vol. 10, pp. 169-178 (2008).
Vaz, Mario et al., "Regional Sympathetic Nervous Activity and Oxygen Consumption in Obese Normotensive Human Subjects," Circulation, vol. 96, pp. 3423-3429 (1997).
Bergman, Richard N. et al., << Direct enhancement of insulin secretion by vagal stimulation of the isolated pancreas, >> American Journal of Physiology, vol. 225, No. 2, pp. 481-486 (1973).
Lee, King C. et al., "The Hepatic Vagus Nerve and the Neural Regulation of Insulin Secretion," Endocrinology, vol. 117, No. 1, pp. 307-315 (1985).
Okazaki, Hiroshi et al., "Modulation of Insulin Secretion by Hepatic Vagotomy in Cirrhotic Rats," Physiology & Behavior, vol. 53, pp. 521-525 (1993).
Imai, Junta et al., "Regulation of Pancreatic $\beta$ Cell Mass by Neuronal Signals from the Liver," Science, vol. 322, pp. 1250-1254 (2008).
Taborsky, Jr., Gerald J. et al., "Minireview: The Role of the Autonomic Nervous System in Mediating the Glucagon Response to Hypoglycemia," Endocrinology, vol. 153, pp. 1055-1062 (2012).
Unger, Roger H. et al., "Glucagonocentric restructuring of diabetes: A pathophysiologic and therapeutic makeover," The Journal of Clinical Investigation, vol. 122, No. 1 (2012).
Hiatt, Jonathan R. et al., "Surgical Anatomy of the Hepatic Arteries in 1000 Cases," Annals of Surgery, vol. 220, No. 1, pp. 50-52 (1994).
Liu, David M. et al., << Angiographic Considerations in Patients Undergoing Liver-directed Therapy, >> Journal of Vascular Interventional Radiology, vol. 16, pp. 911-935 (2005).
Lee, Aram J. et al., << The Road Less Traveled : Importance of the Lesser Branches of the Celiac Axis in Liver Embolotherapy, >> RadioGraphics, vol. 32, pp. 1121-1132 (2012).
Consiglieri, Luisa et al., "Theoretical analysis of the heat convection coefficient in large vessels and the significance for thermal ablative therapies," Physics in Medicine and Biology, vol. 487, pp. 4125-4134 (2003).
Haines, David E. et al., Tissue Heating During Radiofrequency Catheter Ablation—A Thermodynamic Model, PACE, vol. 12, pp. 963-976 (Jun. 1989).
Kolios, M. C. et al., << Large blood vessel cooling in heated tissues: A numerical study, Physics in Medicine and Biology, vol. 40, pp. 477-494 (1995).
Panescu, Dorin et al., "Three-Dimensional Finite Element Analysis of Current Density and Temperature Distributions During Radio-Frequency Ablation," IEEE Transactions on Biomedical Engineering, vol. 42, No. 9, pp. 879-890 (Sep. 1995).
Pearce, John A. et al., "Blood vessel architectural features and their effect on thermal phenomena," Critical Reviews, vol. CR75, pp. 231-277, SPIE Optical Engineering Press (2000).
Agah, Ramtin et al., "Rate Process Model for Arterial Tissue Thermal Damage: Implications on Vessel Photocoagulation," Lasers in Surgery and Medicine, vol. 15, pp. 176-184 (1994).
Roemer, R. B., << Optimal power deposition in hyperthermia, >> International Journal of Hyperthermia, vol. 7, No. 2, pp. 317-341 (1991).
Tangwongsan, Chanchana, "Fluid Velocity Measurement Using Convective Heat Transfer Coefficient Measuring System," 2007 IEEE/NIH Life Science Systems and Applications Workshop, pp. 81-87 (2007).
Tungjitkusolmun, Supan et al., "Three-Dimensional Finite-Element Analyses for Radio-Frequency Hepatic Tumor Ablation," IEEE Transactions on Biomedical Engineering, vol. 49, No. 1, pp. 3-9 (Jan. 2002).

(56) References Cited

OTHER PUBLICATIONS

Valvano, J.W. et al., << Thermal Conductivity and Diffusivity of Biomaterials Measured with Self-Heated Thermistors, >> International Journal of Thermophysics, vol. 6, No. 3, pp. 301-311 (1985).
Brace, Christopher L. "Temperature-dependent dielectric properties of liver tissue measured during thermal ablation: Toward an improved numerical model," $30^{th}$ Annual International IEEE EMBS Conference, pp. 230-233 (2008).
Coad, James E., "Thermal Tissue Injury and Host Response: A Pathologist Perspective," Slide Presentation (Mar. 2008).
Liu, Z. et al "Computer modeling of the effect of perfusion on heating patterns in radiofrequency tumor ablation," International Journal of Hyperthermia, vol. 23, No. 1, pp. 49-58 (Feb. 2007).
Lehmann, K. S. et al., "Ex situ quantification of the cooling effect of liver vessels on radiofrequency ablation," Langenbecks Archives of Surgery, vol. 394, pp. 475-481 (2009).
Wood, Thomas H., "Lethal Effects of High and Low Temperatures on Unicellular Organisms," Advanced Biology of Medicine and Physics, vol. 4, pp. 119-165 (1956).
Watton, Paul N. et al., "Modelling the mechanical response of elastin for arterial tissue," Journal of Biomechanics, vol. 42, pp. 1320-1325 (2009).
Yu, Nam C. et al., "Microwave Liver Ablation: Influence of Hepatic Vein Size on Heat-sink Effect in a Porcine Model," Journal of Vascular Interventional Radiology, vol. 19, pp. 1087-1092 (2008).
Wright, Neil T., "On a Relationship Between the Arrhenius Parameters from Thermal Damage Studies," Transactions of the ASME, vol. 125, pp. 300-304 (Apr. 2003).
Burdio, Fernando et al., "Research and development of a new RF-assisted device for bloodless rapid transection of the liver: Computational modeling and in vivo experiments," BioMedical Engineering OnLine, vol. 8, No. 6 (2009), available at http://www.biomeidcal-engineering-online.com/content/8/1/6.
Ulucakli, M. Erol, "Simulation of Radiofrequency Ablation and Thermal Damage to Tissue," IEEE Annual Northeast Bioengineering Conference, pp. 93-94 (2006).
Despa, F. et al., "The relative thermal stability of tissue macromolecules and cellular structure in burn injury," Burns, vol. 31, pp. 568-577 (2005).
Chang, Isaac A. et al., << Thermal modeling of lesion growth with radiofrequency ablation, BioMedical Engineering OnLine, vol. 3, No. 27 (2004), available at http://www.biomeidcal-engineering-online.com/content/3/1/27.
Borrelli, M.J. et al., << Time-Temperature Analysis of Cell Killing of BHK Cells Heated at Temperatures in the Range of 43.5° C. to 57.0° C., International Journal of Radiation Oncology, Biology and Physics, vol. 19, No. 2, pp. 389-399 (Aug. 1990).
Aytac, Suat K. et al., << Correlation Between the Diameter of the Main Renal Artery and the Presence of an Accessory Renal Artery, >> Journal of Ultrasound in Medicine, vol. 22, pp. 433-439 (2003).
Berthoud, Hans-Rudolf, "Anatomy and Function of Sensory Hepatic Nerves," The Anatomical Record Part A, vol. 280A, pp. 827-835 (2004).
Dodge, Jr., JT et al., "Lumen diameter of normal human coronary arteries. Influence of age, sex, anatomic variation, and left ventricular hypertrophy or dilation," Circulation, vol. 86, pp. 232-246 (1992).
Inomoto, Takuya et al., "Experiences of 120 microsurgical reconstructions of hepatic artery in living related liver transplantation," Surgery, vol. 119, No. 1, pp. 20-26 (Jan. 1996).
Jones, R.M. et al., << The hepatic artery: A reminder of surgical anatomy, >> Journal of the Royal College of Surgeons of Edinburgh, vol. 46, pp. 168-170 (Jun. 2001).
Kimani, SM et al., "Comparative intimal-media morphology of the human splenic and common hepatic arteries," Journal of Morphological Science, vol. 28, No. 1, pp. 52-56 (2011).

McCuskey, Robert S., "Anatomy of Efferent Hepatic Nerves," The Anatomical Record Part A, vol. 280A, pp. 821-826 (2004).
Schenk, Jr., Worthington G. et al., "Direct Measurement of Hepatic Blood Flow in Surgical Patients," Annals of Surgery, vol. 156, No. 3, pp. 463-469 (Sep. 1962).
Sherif, R.Z. et al., "Liver Anatomy," Surgical Clinics of North America, vol. 90, pp. 643-653 (2010).
Tziafalia, Christina et al., "Echo-Doppler Measurements of Portal Vein and Hepatic Artery in Asymptomatic Patients with Hepatitis B Virus and Healthy Adults," Journal of Gastrointestinal and Liver Diseases, vol. 15, No. 4, pp. 343-346 (Dec. 2006).
Uchida, Masfumi et al., "CT Image Fusion for 3D Depiction of Anatomic Abnormalities of the Hepatic Hilum," American Journal of Roentgenology, vol. 189, pp. W184-W191 (Oct. 2007).
Stovichek, GV, "Comparative evaluation of age-related and organic characteristics of the structure of the adventitial nerve plexuses in human arteries," Archives of Anatomy, Histology and Embryology, vol. 93, No. 9, pp. 77-82 (1987).
Stovichek, GV, "Myeloarchitectonics of visceral nerves during human ontogeny," Archives of Anatomy, Histology and Embryology, vol. 80, No. 1, pp. 30-38 (1981).
Stovichek, GV, "Regularities of the Morphogenesis of Visceral Organ Nervous Connections at Different Stages of Human Postnatal Development," Morphology, vol. 125, No. 3, pp. 14-18 (2004).
Stovichek, GV et al., "Morphological Regularities of Adventitial Nerve Plexus Variability in Visceral Arteries on Different Stages of Human Postnatal Ontogenesis," Morphology, vol. 112, No. 5, pp. 43-48 (1997).
Doumas, Michael et al., "Renal sympathetic denervation in hypertension," Current Opinion in Nephrology and Hypertension, vol. 20, pp. 647-653 (2011).
Esler, Murray D et al., << Renal sympathetic denervation in patients with treatment-resistant hypertension (The Symplicity HTN-2 Trial): A randomised controlled trial, >> Lancet, vol. 376, pp. 1903-1909 (2010).
Katona, Peter G., "Biomedical engineering in heart-brain medicine: A review," Cleveland Clinic Journal of Medicine, vol. 77, Supplement 3, pp. S46-S50 (Jul. 2010).
Krum, Henry et al., "Catheter-based renal sympathetic denervation for resistant hypertension: A multicentre safety and proof-of-principle cohort study," Lancet, vol. 373, pp. 1275-1281 (2009).
Prochnau, Dirk et al., "Catheter-based renal denervation for drug-resistant hypertension by using a standard electrophysiology catheter," EuroIntervention, vol. 7, pp. 1077-1080 (Sep. 2011).
Roth, Steven M., "Endovenous Radiofrequency Ablation of Superficial and Perforator Veins," Surgical Clinics of North America, vol. 87, pp. 1267-1284 (2007).
Medtronic ATAKR® II 4802 Ablation System Technical Manual (2001).
Buch, Eric et al., "A Novel Method to Prevent Phrenic Nerve Injury During Catheter Ablation," Heart Rhythm, vol. 4, No. 1, pp. 95-98 (Jan. 2007).
Bunch, T. Jared et al., "Mechanisms of Phrenic Nerve Injury During Radiofrequency Ablation at the Pulmonary Vein Orifice," Journal of Cardiovascular Electrophysiology, vol. 16, No. 12, pp. 1318-1325 (Dec. 2005).
Guiot, Aurelie et al., "Collateral Nervous Damages After Cryoballoon Pulmonary Vein Isolation," Journal of Cardiovascular Electrophysiology, vol. 23, No. 4, pp. 346-351 (Apr. 2012).
Lee, Bong-Ki et al., << Right Phrenic Nerve Injury Following Electrical Disconnection of the Right Superior Pulmonary Vein, >> PACE, vol. 27, pp. 1444-1446 (2004).
Sacher, Frederic et al, "Phrenic Nerve Injury After Atrial Fibrillation Catheter Ablation," Journal of the American College of Cardiology, vol. 47, No. 12, pp. 2498-2503 (2006).
Smith, Harold P. et al., "Radiofrequency neurolysis in a clinical model," Journal of Nerurosurgery, vol. 55, pp. 246-253 (1981).

\* cited by examiner

METHODS FOR THERMALLY-INDUCED HEPATIC NEUROMODULATION

RELATED APPLICATIONS

The present application is a continuation of International Application No. PCT/US2012/068630, filed Dec. 7, 2012, which claims priority to U.S. Provisional Application No. 61/568,843, filed Dec. 9, 2011, the entirety of which is hereby incorporated herein by reference herein.

FIELD

The disclosure relates generally to therapeutic neuromodulation and more specifically to embodiments of devices, systems and methods for therapeutically effecting neuromodulation of targeted nerve fibers of, for example, the hepatic system, to treat metabolic diseases or conditions, such as diabetes mellitus.

BACKGROUND

Chronic hyperglycemia is one of the defining characteristics of diabetes mellitus. Hyperglycemia is a condition in which there is an elevated blood glucose concentration. An elevated blood glucose concentration may result from impaired insulin secretion from the pancreas and also, or alternatively, from cells failing to respond to insulin normally. Excessive glucose release from the kidneys and the liver is a significant contributor to fasting hyperglycemia. The liver is responsible for approximately 90% of the excessive glucose production.

Type 1 diabetes mellitus results from autoimmune destruction of the pancreatic beta cells leading to inadequate insulin production. Type 2 diabetes mellitus is a more complex, chronic metabolic disorder that develops due to a combination of insufficient insulin production as well as cellular resistance to the action of insulin. Insulin promotes glucose uptake into a variety of tissues and also decreases production of glucose by the liver and kidneys; insulin resistance results in reduced peripheral glucose uptake and increased endogenous glucose output, both of which drive blood the glucose concentration above normal levels.

Current estimates are that approximately 26 million people in the United States (over 8% of the population) have some form of diabetes mellitus. Treatments, such as medications, diet, and exercise, seek to control blood glucose levels, which require a patient to closely monitor his or her blood glucose levels. Additionally, patients with type 1 diabetes mellitus, and many patients with type 2 diabetes mellitus, are required to take insulin every day. Insulin is not available in a pill form, however, but must be injected under the skin. Because treatment for diabetes mellitus is self-managed by the patient on a day-to-day basis, compliance or adherence with treatments can be problematic.

SUMMARY

Several embodiments described herein relate generally to devices, systems and methods for therapeutically effecting neuromodulation of targeted nerve fibers to treat various medical conditions, disorders and diseases. In some embodiments, neuromodulation of targeted nerve fibers is used to treat, or reduce the risk of occurrence of symptoms associated with, a variety of metabolic diseases. For example, neuromodulation of targeted nerve fibers can treat, or reduce the risk of occurrence of symptoms associated with, diabetes (e.g., diabetes mellitus) or other diabetes-related diseases. The methods described herein can advantageously treat diabetes without requiring daily insulin injection or constant monitoring of blood glucose levels. The treatment provided by the devices, systems and methods described herein can be permanent or at least semi-permanent (e.g., lasting for several weeks, months or years), thereby reducing the need for continued or periodic treatment. Embodiments of the devices described herein can be temporary or implantable.

In some embodiments, neuromodulation of targeted nerve fibers as described herein can be used for the treatment of insulin resistance, genetic metabolic syndromes, ventricular tachycardia, atrial fibrillation or flutter, arrhythmia, inflammatory diseases, hypertension, obesity, hyperglycemia, hyperlipidemia, eating disorders, and/or endocrine diseases. In some embodiments, neuromodulation of targeted nerve fibers treats any combination of diabetes, insulin resistance, or other metabolic diseases. In some embodiments, temporary or implantable neuromodulators may be used to regulate satiety and appetite. In several embodiments, modulation of nervous tissue that innervates (afferently or efferently) the liver is used to treat hemochromatosis, Wilson's disease, non-alcoholic steatohepatitis (NASH), non-alcoholic fatty liver disease (NAFLD), and/or other conditions affecting the liver and/or liver metabolism.

In some embodiments, sympathetic nerve fibers associated with the liver are selectively disrupted (e.g., ablated, denervated, disabled, severed, blocked, desensitized, removed) to decrease hepatic glucose production and/or increase hepatic glucose uptake, thereby aiding in the treatment of, or reduction in the risk of, diabetes and/or related diseases or disorders. The disruption can be permanent or temporary (e.g., for a matter of several days, weeks or months). In some embodiments, sympathetic nerve fibers in the hepatic plexus are selectively disrupted. In some embodiments, sympathetic nerve fibers surrounding the common hepatic artery proximal to the proper hepatic artery, sympathetic nerve fibers surrounding the proper hepatic artery, sympathetic nerve fibers in the celiac ganglion adjacent the celiac artery, other sympathetic nerve fibers that innervate or surround the liver, sympathetic nerve fibers that innervate the pancreas, sympathetic nerve fibers that innervate fat tissue (e.g., visceral fat), sympathetic nerve fibers that innervate the adrenal glands, sympathetic nerve fibers that innervate the small intestine (e.g., duodenum), sympathetic nerve fibers that innervate the stomach, sympathetic nerve fibers that innervate brown adipose tissue, sympathetic nerve fibers that innervate skeletal muscle, and/or sympathetic nerve fibers that innervate the kidneys are selectively disrupted or modulated to facilitate treatment or reduction of symptoms associated with diabetes (e.g., diabetes mellitus) or other metabolic diseases or disorders. In some embodiments, the methods, devices and systems described herein are used to therapeutically modulate autonomic nerves associated with any diabetes-relevant organs or tissues.

In accordance with several embodiments, any nerves containing autonomic fibers are modulated, including, but not limited to, the saphenous nerve, femoral nerves, lumbar nerves, median nerves, ulnar nerves, vagus nerves, and radial nerves. Nerves surrounding arteries or veins other than the hepatic artery may be modulated such as, but not limited to, nerves surrounding the superior mesenteric artery, the inferior mesenteric artery, the femoral artery, the pelvic arteries, the portal vein, pulmonary arteries, pulmonary veins, abdominal aorta, vena cavas, splenic arteries, gastric arteries, the internal carotid artery, the internal jugular vein, the vertebral artery, renal arteries, and renal veins.

In accordance with several embodiments, a therapeutic neuromodulation system is used to selectively disrupt sympathetic nerve fibers. The neuromodulation system can comprise an ablation catheter system and/or a delivery catheter system. An ablation catheter system may use radiofrequency (RF) energy to ablate sympathetic nerve fibers to cause neuromodulation or disruption of sympathetic communication. In some embodiments, an ablation catheter system uses ultrasonic energy to ablate sympathetic nerve fibers. In some embodiments, an ablation catheter system uses ultrasound (e.g., high-intensity focused ultrasound or low-intensity focused ultrasound) energy to selectively ablate sympathetic nerve fibers. In other embodiments, an ablation catheter system uses electroporation to modulate sympathetic nerve fibers. An ablation catheter, as used herein, shall not be limited to causing ablation, but also includes devices that facilitate the modulation of nerves (e.g., partial or reversible ablation, blocking without ablation, stimulation). In some embodiments, a delivery catheter system delivers drugs or chemical agents to nerve fibers to modulate the nerve fibers (e.g., via chemoablation). Chemical agents used with chemoablation (or some other form of chemically-mediated neuromodulation) may, for example, include phenol, alcohol, or any other chemical agents that cause chemoablation of nerve fibers. In some embodiments, cryotherapy is used. For example, an ablation catheter system is provided that uses cryoablation to selectively modulate (e.g., ablate) sympathetic nerve fibers. In other embodiments, a delivery catheter system is used with brachytherapy to modulate the nerve fibers. The catheter systems may further utilize any combination of RF energy, ultrasonic energy, focused ultrasound (e.g., HIFU, LIFU) energy, ionizing energy (such as X-ray, proton beam, gamma rays, electron beams, and alpha rays), electroporation, drug delivery, chemoablation, cryoablation, brachytherapy, or any other modality to cause disruption or neuromodulation (e.g., ablation, denervation, stimulation) of autonomic (e.g., sympathetic or parasympathetic) nerve fibers.

In some embodiments, a minimally invasive surgical technique is used to deliver the therapeutic neuromodulation system. For example, a catheter system for the disruption or neuromodulation of sympathetic nerve fibers can be delivered intra-arterially (e.g., via a femoral artery, brachial artery, radial artery). In some embodiments, an ablation catheter system is advanced to the proper hepatic artery to ablate (completely or partially) sympathetic nerve fibers in the hepatic plexus. In other embodiments, the ablation catheter system is advanced to the common hepatic artery to ablate sympathetic nerve fibers surrounding the common hepatic artery. In some embodiments, the ablation catheter system is advanced to the celiac artery to ablate sympathetic nerve fibers in the celiac ganglion or celiac plexus. An ablation or delivery catheter system can be advanced within other arteries (e.g., left hepatic artery, right hepatic artery, gastroduodenal artery, gastric arteries, splenic artery, renal arteries, etc.) in order to disrupt targeted sympathetic nerve fibers associated with the liver or other organs or tissue (such as the pancreas, fat tissue (e.g., visceral fat of the liver), the adrenal glands, the stomach, the small intestine, bile ducts, brown adipose tissue, skeletal muscle), at least some of which may be clinically relevant to diabetes.

In some embodiments, a therapeutic neuromodulation or disruption system is delivered intravascularly through the venous system. For example, the therapeutic neuromodulation system may be delivered either through the portal vein or through the inferior vena cava. In some embodiments, the neuromodulation system is delivered percutaneously to the biliary tree to modulate or disrupt sympathetic nerve fibers.

In other embodiments, the neuromodulation system is delivered transluminally or laparoscopically to modulate or disrupt sympathetic nerve fibers. For example, the neuromodulation system may be delivered transluminally either through the stomach, or through the duodenum.

In some embodiments, minimally invasive surgical delivery of the neuromodulation system is accomplished in conjunction with image guidance techniques. For example, a visualization device such as a fiberoptic scope can be used to provide image guidance during minimally invasive surgical delivery of the neuromodulation system. In some embodiments, fluoroscopic, computerized tomography (CT), radiographic, optical coherence tomography (OCT), intravascular ultrasound (IVUS), Doppler, thermography, and/or magnetic resonance (MR) imaging is used in conjunction with minimally invasive surgical delivery of the neuromodulation system. In some embodiments, radiopaque markers are located at a distal end of the neuromodulation system to aid in delivery and alignment of the neuromodulation system.

In some embodiments, an open surgical procedure is used to access the nerve fibers to be modulated. In some embodiments, any of the modalities described herein, including, but not limited to, RF energy, ultrasonic energy, HIFU, thermal energy, light energy, electrical energy other than RF energy, drug delivery, chemoablation, cryoablation, steam or hot-water, ionizing energy (such as X-ray, proton beam, gamma rays, electron beams, and alpha rays) or any other modality are used in conjunction with an open surgical procedure to modulate or disrupt sympathetic nerve fibers. In other embodiments, nerve fibers are surgically cut (e.g., transected) to disrupt conduction of nerve signals.

In some embodiments, a non-invasive (e.g., transcutaneous) procedure is used to modulate or disrupt sympathetic nerve fibers. In some embodiments, any of the modalities described herein, including, but not limited, to RF energy, ultrasonic energy, HIFU energy, radiation therapy, light energy, infrared energy, thermal energy, steam, hot water, magnetic fields, ionizing energy, other forms of electrical or electromagnetic energy or any other modality are used in conjunction with a non-invasive procedure to modulate or disrupt sympathetic nerve fibers.

In accordance with some embodiments, the neuromodulation system is used to modulate or disrupt sympathetic nerve fibers at one or more locations or target sites. For example, an ablation catheter system may perform ablation in a circumferential or radial pattern, and/or the ablation catheter system may perform ablation at a plurality of points linearly spaced apart along a vessel length. In other embodiments, an ablation catheter system performs ablation at one or more locations in any other pattern capable of causing disruption in the communication pathway of sympathetic nerve fibers (e.g., spiral patterns, zig-zag patterns, multiple linear patterns, etc.). The pattern can be continuous or non-continuous (e.g., intermittent). The ablation may be targeted at certain portions of the circumference of the vessels (e.g., half or portions less than half of the circumference).

In accordance with embodiments of the invention disclosed herein, therapeutic neuromodulation to treat various medical disorders and diseases includes neural stimulation of targeted nerve fibers. For example, autonomic nerve fibers (e.g., sympathetic nerve fibers, parasympathetic nerve fibers) may be stimulated to treat, or reduce the risk of occurrence of, diabetes (e.g., diabetes mellitus) or other conditions, diseases and disorders.

In some embodiments, parasympathetic nerve fibers that innervate the liver are stimulated. In some embodiments, parasympathetic nerve fibers that innervate the pancreas, fat tissue (e.g., visceral fat of the liver), the adrenal glands, the stomach, the kidneys, brown adipose tissue, skeletal muscle, and/or the small intestine (e.g., duodenum) are stimulated. In accordance with some embodiments, any combination of parasympathetic nerve fibers innervating the liver, the pancreas, fat tissue, the adrenal glands, the stomach, the kidneys, brown adipose tissue, skeletal muscle, and the small intestine are stimulated to treat, or alleviate or reduce the risk of occurrence of the symptoms associated with, diabetes (e.g., diabetes mellitus) or other conditions, diseases, or disorders. In some embodiments, the organs or tissue are stimulated directly either internally or externally.

In some embodiments, a neurostimulator is used to stimulate sympathetic or parasympathetic nerve fibers. In some embodiments, the neurostimulator is implantable. In accordance with some embodiments, the implantable neurostimulator electrically stimulates parasympathetic nerve fibers. In some embodiments, the implantable neurostimulator chemically stimulates parasympathetic nerve fibers. In still other embodiments, the implantable neurostimulator uses any combination of electrical stimulation, chemical stimulation, or any other method capable of stimulating parasympathetic nerve fibers.

In other embodiments, non-invasive neurostimulation is used to effect stimulation of parasympathetic nerve fibers. For example, transcutaneous electrical stimulation may be used to stimulate parasympathetic nerve fibers. Other energy modalities can also be used to affect non-invasive neurostimulation of parasympathetic nerve fibers (e.g., light energy, ultrasound energy).

In some embodiments, neuromodulation of targeted autonomic nerve fibers treats diabetes (e.g., diabetes mellitus) and related conditions by decreasing systemic glucose. For example, therapeutic neuromodulation of targeted nerve fibers can decrease systemic glucose by decreasing hepatic glucose production. In some embodiments, hepatic glucose production is decreased by disruption (e.g., ablation) of sympathetic nerve fibers. In other embodiments, hepatic glucose production is decreased by stimulation of parasympathetic nerve fibers.

In some embodiments, therapeutic neuromodulation of targeted nerve fibers decreases systemic glucose by increasing hepatic glucose uptake. In some embodiments, hepatic glucose uptake is increased by disruption (e.g., ablation) of sympathetic nerve fibers. In other embodiments, hepatic glucose uptake is increased by stimulation of parasympathetic nerve fibers. In some embodiments, triglyceride or cholesterol levels are reduced by the therapeutic neuromodulation.

In some embodiments, disruption or modulation of the sympathetic nerve fibers of the hepatic plexus has no effect on the parasympathetic nerve fibers surrounding the liver. In some embodiments, disruption or modulation (e.g., ablation or denervation) of the sympathetic nerve fibers of the hepatic plexus causes a reduction of very low-density lipoprotein (VLDL) levels, thereby resulting in a beneficial effect on lipid profile. In several embodiments, the invention comprises neuromodulation therapy to affect sympathetic drive and/or triglyceride or cholesterol levels, including high-density lipoprotein (HDL) levels, low-density lipoprotein (LDL) levels, and/or very-low-density lipoprotein (VLDL) levels. In some embodiments, denervation or ablation of sympathetic nerves reduces triglyceride levels, cholesterol levels and/or central sympathetic drive.

In other embodiments, therapeutic neuromodulation of targeted nerve fibers (e.g., hepatic denervation) decreases systemic glucose by increasing insulin secretion. In some embodiments, insulin secretion is increased by disruption (e.g., ablation) of sympathetic nerve fibers (e.g., surrounding branches of the hepatic artery). In other embodiments, insulin secretion is increased by stimulation of parasympathetic nerve fibers. In some embodiments, sympathetic nerve fibers surrounding the pancreas may be modulated to decrease glucagon levels and increase insulin levels. In some embodiments, sympathetic nerve fibers surrounding the adrenal glands are modulated to affect adrenaline or noradrenaline levels. Fatty tissue (e.g., visceral fat) of the liver may be targeted to affect glycerol or free fatty acid levels.

In accordance with several embodiments of the invention, a method of decreasing blood glucose levels within a subject is provided. The method comprises forming an incision in a groin of a subject to access a femoral artery and inserting a neuromodulation catheter into the incision. In some embodiments, the method comprises advancing the neuromodulation catheter from the femoral artery through an arterial system to a proper hepatic artery and causing a therapeutically effective amount of energy to thermally inhibit neural communication along a sympathetic nerve in a hepatic plexus surrounding the proper hepatic artery to be delivered intravascularly by the ablation catheter to the inner wall of the proper hepatic artery, thereby decreasing blood glucose levels within the subject. Other incision or access points may be used as desired or required.

In some embodiments, the neuromodulation catheter is a radiofrequency (RF) ablation catheter comprising one or more electrodes. In some embodiments, the neuromodulation catheter is a high-intensity focused ultrasound ablation catheter. In some embodiments, the neuromodulation catheter is a cryoablation catheter. The method can further comprise stimulating one or more parasympathetic nerves associated with the liver to decrease hepatic glucose production or increase glucose uptake.

In accordance with several embodiments, a method of treating a subject having diabetes or symptoms associated with diabetes is provided. The method can comprise delivering an RF ablation catheter to a vicinity of a hepatic plexus of a subject and disrupting neural communication along a sympathetic nerve of the hepatic plexus by causing RF energy to be emitted from one or more electrodes of the RF ablation catheter. In some embodiments, the RF ablation catheter is delivered intravascularly through a femoral artery to a location within the proper hepatic artery. In some embodiments, the RF energy is delivered extravascularly by the RF ablation catheter.

In some embodiments, disrupting neural communication comprises permanently disabling neural communication along the sympathetic nerve of the hepatic plexus. In some embodiments, disrupting neural communication comprises temporarily inhibiting or reducing neural communication along the sympathetic nerve of the hepatic plexus. In some embodiments, disrupting neural communication along a sympathetic nerve of the hepatic plexus comprises disrupting neural communication along a plurality of sympathetic nerves of the hepatic plexus.

The method can further comprise positioning the RF ablation catheter in the vicinity of the celiac plexus of the subject and disrupting neural communication along a sympathetic nerve of the celiac plexus by causing RF energy to be emitted from one or more electrodes of the RF ablation catheter. In some embodiments, the method comprises positioning the RF ablation catheter in the vicinity of sympathetic nerve fibers that innervate the pancreas and disrupting neural communication along the sympathetic nerve fibers by causing RF energy to be emitted from one or more electrodes of the RF ablation catheter, positioning the RF ablation catheter in the vicinity of sympathetic nerve fibers that innervate the stomach and disrupting neural communication along the sympathetic nerve fibers by causing RF energy to be emitted from one or more electrodes of the RF ablation catheter, and/or positioning the RF ablation catheter in the vicinity of sympathetic nerve fibers that innervate the duodenum and disrupting neural communication along the sympathetic nerve fibers by causing RF energy to be emitted from one or more electrodes of the RF ablation catheter. In some embodiments, drugs or therapeutic agents can be delivered to the liver or surrounding organs or tissues.

In accordance with several embodiments, a method of decreasing blood glucose levels within a subject is provided. The method comprises inserting an RF ablation catheter into vasculature of the subject and advancing the RF ablation catheter to a location of a branch of a hepatic artery (e.g., the proper hepatic artery or the common hepatic artery). In one embodiment, the method comprises causing a therapeutically effective amount of RF energy to thermally inhibit neural communication within sympathetic nerves of a hepatic plexus surrounding the proper hepatic artery to be delivered intravascularly by the ablation catheter to the inner wall of the proper hepatic artery, thereby decreasing blood glucose levels within the subject.

In one embodiment, the therapeutically effective amount of RF energy at the location of the inner vessel wall of the target vessel or at the location of the target nerves is in the range of between about 100 J and about 1 kJ (e.g., between about 100 J and about 500 J, between about 250 J and about 750 J, between about 500 J and 1 kJ, or overlapping ranges thereof). In one embodiment, the therapeutically effective amount of RF energy has a power between about 0.1 W and about 10 W (e.g., between about 0.5 W and about 5 W, between about 3 W and about 8 W, between about 2 W and about 6 W, between about 5 W and about 10 W, or overlapping ranges thereof).

In one embodiment, the RF ablation catheter comprises at least one ablation electrode. The RF ablation catheter may be configured to cause the at least one ablation electrode to contact the inner wall of the hepatic artery branch and maintain contact against the inner wall with sufficient contact pressure while the RE energy is being delivered. In one embodiment, the RF ablation catheter comprises a balloon catheter configured to maintain sufficient contact pressure of the at least one electrode against the inner wall of the hepatic artery branch. In one embodiment, the RF ablation catheter comprises a steerable distal tip configured to maintain sufficient contact pressure of the at least one electrode against the inner wall of the hepatic artery branch. In various embodiments, the sufficient contact pressure may range from about 0.1 g/mm$^2$ to about 100 g/mm$^2$ (e.g., between about 0.1 g/mm$^2$ and about 10 g/mm$^2$). In some embodiments, the RF ablation catheter comprises at least one anchoring member configured to maintain contact of the at least one electrode against the inner wall of the hepatic artery branch.

In accordance with several embodiments, a method of treating a subject having diabetes or symptoms associated with diabetes is provided. In one embodiment, the method comprises delivering an RF ablation catheter to a vicinity of a hepatic plexus within a hepatic artery branch (e.g., proper hepatic artery, common hepatic artery or adjacent or within a bifurcation between the two). In one embodiment, the RF ablation catheter comprises at least one electrode. The method may comprise positioning the at least one electrode in contact with an inner wall of the hepatic artery branch. In one embodiment, the method comprises disrupting neural communication of sympathetic nerves of the hepatic plexus surrounding the hepatic artery branch by applying an electric signal to the at least one electrode, thereby causing thermal energy to be delivered by the at least one electrode to heat the inner wall of the hepatic artery branch. Non-ablative heating, ablative heating, or combinations thereof, are used in several embodiments.

In one embodiment, disrupting neural communication comprises permanently disabling neural communication of sympathetic nerves of the hepatic plexus. In one embodiment, disrupting neural communication comprises temporarily inhibiting or reducing neural communication along sympathetic nerves of the hepatic plexus. In some embodiments, the method comprises positioning the RF ablation catheter in the vicinity of the celiac plexus of the subject and disrupting neural communication along sympathetic nerves of the celiac plexus, positioning the RF ablation catheter in the vicinity of sympathetic nerve fibers that innervate the pancreas and disrupting neural communication along the sympathetic nerve fibers, positioning the RF ablation catheter in the vicinity of sympathetic nerve fibers that innervate the stomach and disrupting neural communication along the sympathetic nerve fibers, and/or positioning the RF ablation catheter in the vicinity of sympathetic nerve fibers that innervate the duodenum and disrupting neural communication along the sympathetic nerve fibers by causing RF energy to be emitted from the at least one electrode of the RF ablation catheter. In several embodiments, a feedback mechanism is provided to facilitate confirmation of neuromodulation and to allow for adjustment of treatment in real time.

In accordance with several embodiments, a method of treating a subject having diabetes or symptoms associated with diabetes is provided. In one embodiment, the method comprises delivering a neuromodulation catheter within a hepatic artery to a vicinity of a hepatic plexus of a subject and modulating nerves of the hepatic plexus by causing RF energy to be emitted from one or more electrodes of the RF ablation catheter. In one embodiment, the step of modulating the nerves of the hepatic plexus comprises denervating sympathetic nerves of the hepatic plexus and/or stimulating parasympathetic nerves of the hepatic plexus. In one embodiment, the sympathetic denervation and the parasympathetic stimulation are performed simultaneously. In one embodiment, the sympathetic denervation and the parasympathetic stimulation are performed sequentially. In one embodiment, sympathetic nerves are modulated without modulating parasympathetic nerves surrounding the same vessel or tissue.

In accordance with several embodiments, an apparatus configured for hepatic neuromodulation is provided. In one embodiment, the apparatus comprises a balloon catheter configured for intravascular placement within a hepatic artery branch. In one embodiment, the balloon catheter comprises at least one expandable balloon and a bipolar electrode pair. In one embodiment, at least one of the bipolar electrode pair is configured to be positioned to be expanded into contact with an inner wall of the hepatic artery branch upon expansion of the at least one expandable balloon. In one embodiment, the bipolar electrode pair is configured to deliver a thermal dose of energy configured to achieve hepatic denervation. The at least one expandable balloon may be configured to maintain sufficient contact pressure between the at least one electrode of the bipolar electrode pair and the inner wall of the hepatic artery branch. In some embodiments, the balloon catheter comprises two expandable balloons, each having one electrode of the bipolar electrode pair disposed thereon. In one embodiment, the balloon catheter comprises a single expandable balloon and the bipolar electrode pair is disposed on the expandable balloon. In one embodiment, the balloon comprises a cooling fluid within a lumen of the balloon.

In accordance with several embodiments, an apparatus configured for hepatic neuromodulation is provided. In one embodiment, the apparatus comprises a catheter comprising a lumen and an open distal end and a steerable shaft configured to be slidably received within the lumen of the catheter. In one embodiment, at least a distal portion of the steerable shaft comprises a shape memory material having a pre-formed shape configured to cause the distal portion of the steerable shaft to bend to contact a vessel wall upon advancement of the distal portion of the steerable shaft out of the open distal end of the catheter. In one embodiment, a distal end of the steerable shaft comprises at least one electrode that is configured to be activated to deliver a thermal dose of energy configured to achieve denervation of a branch of a hepatic artery or other target vessel. In one embodiment, the shape memory material of the steerable shaft is sufficiently resilient to maintain sufficient contact pressure between the at least one electrode and an inner wall of the branch of the hepatic artery during a hepatic denervation procedure. The outside diameter at a distal end of the catheter may be smaller than the outside diameter at a proximal end of the catheter to accommodate insertion within vessels having a small inner diameter. In various embodiments, the outside diameter at the distal end of the catheter is between about 1 mm and about 4 mm. In one embodiment, the at least one electrode comprises a coating having one or more windows.

In accordance with several embodiments, a neuromodulation kit is provided. In one embodiment, the kit comprises a neuromodulation catheter configured to be inserted within a vessel of the hepatic system for modulating nerves surrounding the hepatic artery. In one embodiment, the kit comprises a plurality of energy delivery devices configured to be inserted within the lumen of the neuromodulation catheter. In one embodiment, each of the energy delivery devices comprises at least one modulation element at or near a distal end of the energy delivery device. In one embodiment, each of the energy delivery devices comprises a distal portion comprising a different pre-formed shape memory configuration. The at least one modulation element may be configured to be activated to modulate at least a portion of the nerves surrounding the hepatic artery to treat symptoms associated with diabetes.

In several embodiments, the invention comprises modulation of the nervous system to treat disorders affecting insulin and/or glucose, such as insulin regulation, glucose uptake, metabolism, etc. In some embodiments, nervous system input and/or output is temporarily or permanently modulated (e.g., decreased). Several embodiments are configured to perform one or a combination of the following effects: ablating nerve tissue, heating nerve tissue, cooling the nerve tissue, deactivating nerve tissue, severing nerve tissue, cell lysis, apoptosis, and necrosis. In some embodiments, localized neuromodulation is performed, leaving surrounding tissue unaffected. In other embodiments, the tissue surrounding the targeted nerve(s) is also treated.

In accordance with several embodiments, methods of hepatic denervation are performed with shorter procedural and energy application times than renal denervation procedures. In several embodiments, hepatic denervation is performed without causing pain or mitigates pain to the subject during the treatment. In accordance with several embodiments, neuromodulation (e.g., denervation or ablation) is performed without causing stenosis or thrombosis within the target vessel (e.g., hepatic artery). In embodiments involving thermal treatment, heat lost to the blood stream may be prevented or reduced compared to existing denervation systems and methods, resulting in lower power and shorter treatment times. In various embodiments, the methods of neuromodulation are performed with little or no endothelial damage to the target vessels. In several embodiments, energy delivery is delivered substantially equally in all directions (e.g., omnidirectional delivery). In various embodiments of neuromodulation systems (e.g., catheter-based energy delivery systems described herein), adequate electrode contact with the target vessel walls is maintained, thereby reducing power levels, voltage levels and treatment times.

For purposes of summarizing the disclosure, certain aspects, advantages, and novel features of embodiments of the invention have been described herein. It is to be understood that not necessarily all such advantages may be achieved in accordance with any particular embodiment of the invention disclosed herein. Thus, the embodiments disclosed herein may be embodied or carried out in a manner that achieves or optimizes one advantage or group of advantages as taught or suggested herein without necessarily achieving other advantages as may be taught or suggested herein.

DETAILED DESCRIPTION

I. Introduction and Overview

Figure 1:
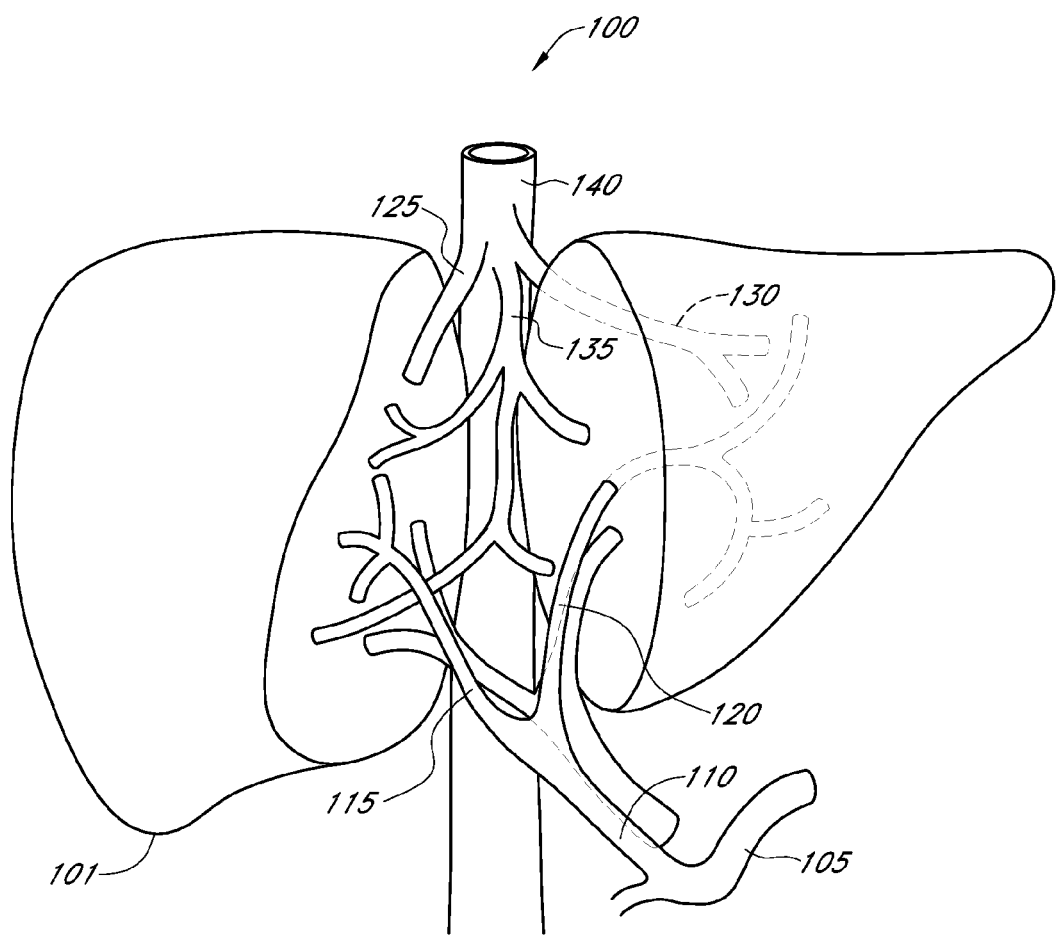
FIG. 1 illustrates the anatomy of a target treatment location including the liver and hepatic blood supply, in accordance with an embodiment of the invention.

Embodiments of the invention described herein are generally directed to therapeutic neuromodulation of targeted nerve fibers to treat, or reduce the risk of occurrence or progression of, various metabolic diseases, conditions, or disorders, including but not limited to diabetes (e.g., diabetes mellitus). While the description sets forth specific details in various embodiments, it will be appreciated that the description is illustrative only and should not be construed in any way as limiting the disclosure. Furthermore, various applications of the disclosed embodiments, and modifications thereto, which may occur to those who are skilled in the art, are also encompassed by the general concepts described herein.

The autonomic nervous system includes the sympathetic and parasympathetic nervous systems. The sympathetic nervous system is the component of the autonomic nervous system that is responsible for the body's "fight or flight" responses, those that can prepare the body for periods of high stress or strenuous physical exertion. One of the functions of the sympathetic nervous system, therefore, is to increase availability of glucose for rapid energy metabolism during periods of excitement or stress, and to decrease insulin secretion.

The liver can play an important role in maintaining a normal blood glucose concentration. For example, the liver can store excess glucose within its cells by forming glycogen, a large polymer of glucose. Then, if the blood glucose concentration begins to decrease too severely, glucose molecules can be separated from the stored glycogen and returned to the blood to be used as energy by other cells. The liver is a highly vascular organ that is supplied by two independent blood supplies, one being the portal vein (as the liver's primary blood supply) and the other being the hepatic artery (being the liver's secondary blood supply).

The process of breaking down glycogen into glucose is known as glycogenolysis, and is one way in which the sympathetic nervous system can increase systemic glucose. In order for glycogenolysis to occur, the enzyme phosphorylase must first be activated in order to cause phosphorylation, which allows individual glucose molecules to separate from branches of the glycogen polymer. One method of activating phosphorylase, for example, is through sympathetic stimulation of the adrenal medulla. By stimulating the sympathetic nerves that innervate the adrenal medulla, epinephrine is released. Epinephrine then promotes the formation of cyclic AMP, which in turn initiates a chemical reaction that activates phosphorylase. An alternative method of activating phosphorylase is through sympathetic stimulation of the pancreas. For example, phosphorylase can be activated through the release of the hormone glucagon by the alpha cells of the pancreas. Similar to epinephrine, glucagon stimulates formation of cyclic AMP, which in turn begins the chemical reaction to activate phosphorylase.

Another way in which the liver functions to maintain a normal blood glucose concentration is through the process of gluconeogenesis. When the blood glucose concentration decreases below normal, the liver will synthesize glucose from various amino acids and glycerol in order to maintain a normal blood glucose concentration. Increased sympathetic activity has been shown to increase gluconeogenesis, thereby resulting in an increased blood glucose concentration.

The parasympathetic nervous system is the second component of the autonomic nervous system and is responsible for the body's "rest and digest" functions. These "rest and digest" functions complement the "fight or flight" responses of the sympathetic nervous system. Stimulation of the parasympathetic nervous system has been associated with decreased blood glucose levels. For example, stimulation of the parasympathetic nervous system has been shown to increase insulin secretion from the beta-cells of the pancreas. Because the rate of glucose transport through cell membranes is greatly enhanced by insulin, increasing the amount of insulin secreted from the pancreas can help to lower blood glucose concentration. In some embodiments, stimulation of the parasympathetic nerves innervating the pancreas is combined with denervation of sympathetic nerves innervating the liver to treat diabetes or the symptoms associated with diabetes (e.g., high blood glucose levels, high triglyceride levels, high cholesterol levels) low insulin secretion levels). Stimulation and/or denervation of sympathetic and/or parasympathetic nerves surrounding other organs or tissues may also be performed in combination.

FIG. 1 illustrates a liver 101 and vasculature of a target hepatic treatment location 100. The vasculature includes the common hepatic artery 105, the proper hepatic artery 110, the right hepatic artery 115, the left hepatic artery 120, the right hepatic vein 125, the left hepatic vein 130, the middle hepatic vein 135, and the inferior vena cava 140. In the hepatic blood supply system, blood enters the liver by coursing through the common hepatic artery 105, the proper hepatic artery 110, and then either of the left hepatic artery 120 or the right hepatic artery 115. The right hepatic artery 115 and the left hepatic artery 120 (as well as the portal vein, not shown) provide blood supply to the liver 101, and directly feed the capillary beds within the hepatic tissue of the liver 101. The liver 101 uses the oxygen provided by the oxygenated blood flow provided by the right hepatic artery 115 and the left hepatic artery 120. Deoxygenated blood from the liver 101 leaves the liver 101 through the right hepatic vein 125, the left hepatic vein 130, and the middle hepatic vein 135, all of which empty into the inferior vena cava 140.

Figure 2:
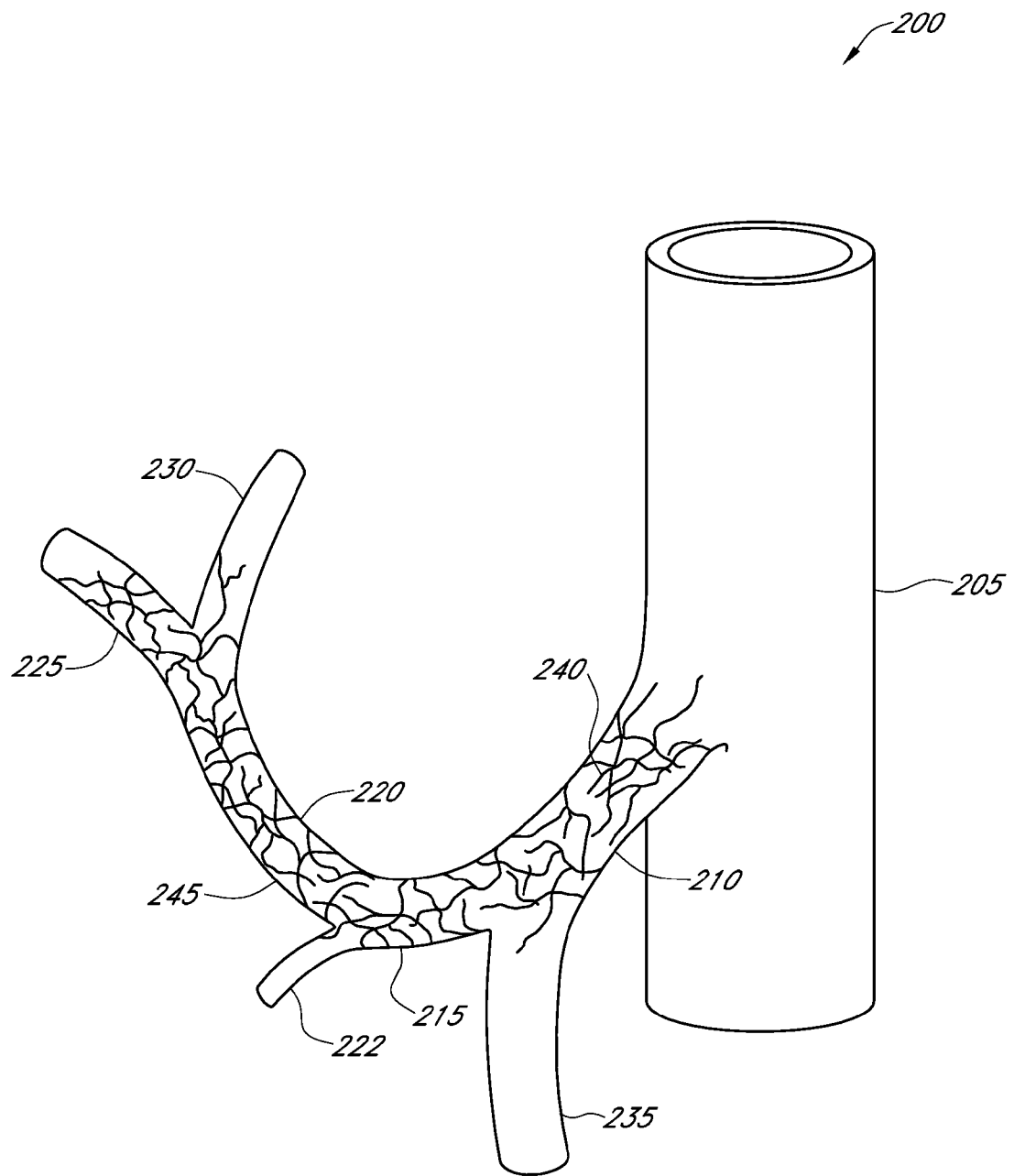
FIG. 2 illustrates various arteries supplying blood to the liver and its surrounding organs and tissues and nerves that innervate the liver and its surrounding organs and tissues.

FIG. 2 illustrates various arteries surrounding the liver and the various nerve systems 200 that innervate the liver and its surrounding organs and tissue. The arteries include the abdominal aorta 205, the celiac artery 210, the common hepatic artery 215, the proper hepatic artery 220, the gastroduodenal artery 222, the right hepatic artery 225, the left hepatic artery 230, and the splenic artery 235. The various nerve systems 200 illustrated include the celiac plexus 240 and the hepatic plexus 245. Blood supply to the liver is pumped from the heart into the aorta and then down through the abdominal aorta 205 and into the celiac artery 210. From the celiac artery 210, the blood travels through the common hepatic artery 215, into the proper hepatic artery 220, then into the liver through the right hepatic artery 225 and the left hepatic artery 230. The common hepatic artery 215 branches off of the celiac trunk. The common hepatic artery 215 gives rise to the gastric and gastroduodenal arteries. The nerves innervating the liver include the celiac plexus 240 and the hepatic plexus 245. The celiac plexus 240 wraps around the celiac artery 210 and continues on into the hepatic plexus 245, which wraps around the proper hepatic artery 220, the common hepatic artery 215, and may continue on to the right hepatic artery 225 and the left hepatic artery 230. In some anatomies, the celiac plexus 240 and hepatic plexus 245 adhere tightly to the walls (and some of the nerves may be embedded in the adventitia) of the arteries supplying the liver with blood, thereby rendering intra-to-extra-vascular neuromodulation particularly advantageous to modulate nerves of the celiac plexus 240 and/or hepatic plexus 245. In several embodiments, the media thickness of the vessel (e.g., hepatic artery) ranges from about 0.1 cm to about 0.25 cm. In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements. In some embodiments, low-power or low-energy (e.g., less than 10 W of power output and/or less than 1 kJ of energy delivered to the inner wall of the target vessel or to the target nerves) intravascular energy delivery may be used because the nerves are tightly adhered to or within the outer walls of the arteries supplying the liver with blood (e.g. hepatic artery branches).

With continued reference to FIGS. 1 and 2, the hepatic plexus 245 is the largest offset from the celiac plexus 240. The hepatic plexus 245 is believed to carry primarily afferent and efferent sympathetic nerve fibers, the stimulation of which can increase blood glucose levels by a number of mechanisms. For example, stimulation of sympathetic nerve fibers in the hepatic plexus 245 can increase blood glucose levels by increasing hepatic glucose production. Stimulation of sympathetic nerve fibers of the hepatic plexus 245 can also increase blood glucose levels by decreasing hepatic glucose uptake. Therefore, by disrupting sympathetic nerve signaling in the hepatic plexus 245, blood glucose levels can be decreased or reduced.

In several embodiments, any of the regions (e.g., nerves) identified in FIGS. 1 and 2 may be modulated according to embodiments described herein. Alternatively, in one embodiment, localized therapy is provided to the hepatic plexus, while leaving one or more of these other regions unaffected. In some embodiments, multiple regions (e.g., of organs, arteries, nerve systems) shown in FIGS. 1 and 2 may be modulated in combination (simultaneously or sequentially).

Figure 3:
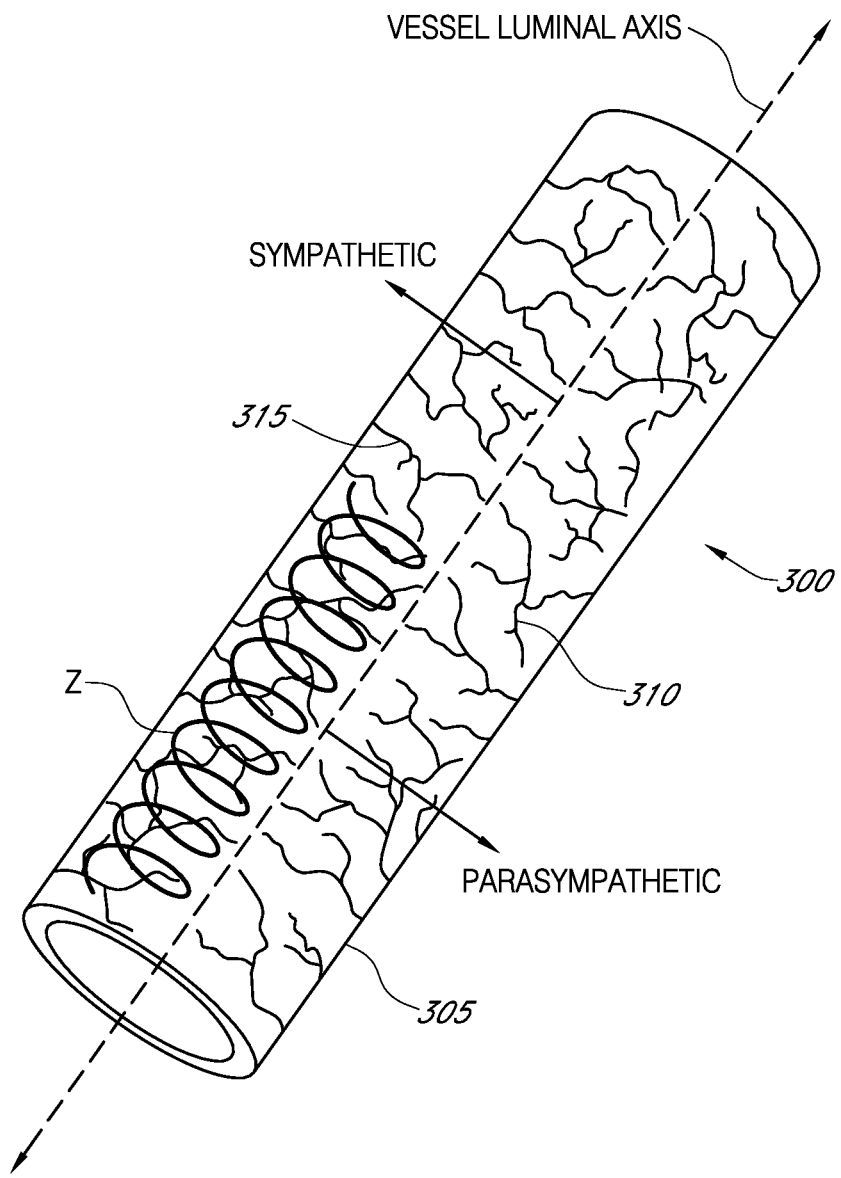
FIG. 3 illustrates a schematic drawing of a common hepatic artery and nerves of the hepatic plexus.

FIG. 3 is a schematic illustration of the nerve fibers of the hepatic plexus 300. A portion of the common hepatic artery 305 (or, alternatively, the proper hepatic artery) is shown with the hepatic plexus 300 wrapping around the artery. Some of the nerve fibers of the hepatic plexus may be embedded within the adventitia of the common hepatic artery 305 (or proper hepatic artery), or at least tightly adhered to or within the outer vascular walls. As shown, there is a vessel luminal axis that follows the center of the artery lumen. The hepatic plexus 300 is comprised of parasympathetic nerves 310 and sympathetic nerves 315. In some anatomies, the parasympathetic nerves 310 tend to course down one half of the circumference of an artery and the sympathetic nerves 315 tend to course down the other half of the artery.

As shown in FIG. 3, the portion of the common hepatic artery 305 is roughly cylindrical, with parasympathetic nerves 310 innervating approximately a 180° arc of the cylinder, and the sympathetic nerves of the hepatic plexus 315 innervating the opposite approximately 180° arc of the cylinder. In some anatomies, there is very little overlap (if any) between the parasympathetic nerves 310 and the sympathetic nerves 315 of the hepatic plexus. Such discretization may be advantageous in embodiments where only sympathetic nerves 315 or parasympathetic nerves 310 of the hepatic plexus are to be modulated. In some embodiments, modulation of the sympathetic nerves 315 of the hepatic plexus may be desirable while modulation of the parasympathetic nerves 310 of the hepatic plexus may not be desirable (or vice-versa).

In some embodiments, only selective regions of the adventitial layer of target vasculature is modulated. In some subjects, parasympathetic and sympathetic nerves may be distributed distinctly on or in the adventitial layer of blood vessels. For example, using an axis created by the lumen of a blood vessel, parasympathetic nerves of the hepatic plexus may lie in one 180 degree arc of the adventitia while sympathetic nerves may lie in the other 180 degree arc of the adventitia, such as shown in FIG. 3. Generally, the sympathetic nerve fibers tend to run along the anterior surface of the hepatic artery, while the parasympathetic nerve fibers are localized toward the posterior surface of the hepatic artery. In these cases, it may be advantageous to selectively disrupt either the sympathetic or the parasympathetic nerves by modulating nerves in either the anterior region or the posterior region.

In some subjects, sympathetic nerve fibers may run along a significant length of the hepatic artery, while parasympathetic nerve fibers may join toward the distal extent of the hepatic artery. Research has shown that the vagus nerve joins the liver hilus near the liver parenchyma (e.g., in a more distal position than the nerves surrounding the hepatic arterial tree). As the vagal nerves are parasympathetic, the nerves surrounding the hepatic artery proximally may be predominantly sympathetic. In accordance with several embodiments, modulation (e.g., ablation) of the proper hepatic artery towards its proximal extent (e.g., halfway between the first branch of the celiac artery and the first branch of the common hepatic artery) is performed when it is desired to disrupt sympathetic nerves in the hepatic plexus. Ablation of the proximal extent of the hepatic artery could advantageously provide the concomitant benefit of avoiding such critical structures as the bile duct and portal vein (which approaches the hepatic artery as it courses distally towards the liver).

In one embodiment, only the anterior regions of the hepatic artery are selectively modulated (e.g., ablated). In one embodiment, approximately 180 degrees of the arterial circumference is ablated. In some embodiments, it is desirable to ablate in the range of about 60° to about 240°, about 80° to about 220°, about 100° to about 200°, about 120° to about 180°, about 140° to about 160°, or overlapping ranges thereof. In some embodiments, the portion of the vessel wall not being targeted opposite the portion of the vessel wall being targeted is actively cooled during the modulation procedure. Such cooling may decrease collateral injury to the nerve fibers not intended for treatment. In many embodiments, cooling is not used.

In embodiments in which only selective portions of the vessel wall are to be treated, a zig-zag, overlapping semicircular, spiral, lasso, or other pattern of ablation may be used to treat only selective regions of nerve tissue in the adventitia. An example of a spiral ablation pattern Z, in accordance with one embodiment, is shown in FIG. 3. In some embodiments, one or more ablation electrodes having an inherent zig-zag, spiral or other pattern are used. In some embodiments, a single point ablation electrode (regardless of electrode pattern) is advanced longitudinally and circumferentially about substantially 180 degrees of the vessel circumference to ablate in a zig-zag, spiral or other pattern, thereby selectively ablating only approximately 180 degrees of the vessel wall and the accompanying nerve tissues. In some embodiments, other patterns of electrode configurations are used. In some embodiments, other patterns of ablation electrode movement (regardless of inherent conformation) are used.

In some embodiments, where only selective regions of the vessel wall are to be modulated (e.g., ablated or stimulated) it may be helpful to have a high degree of catheter control, stability and/or precision. To achieve the control necessary for a high degree of precision, a guide catheter may be used to engage the osteum of a nearby branch (e.g., the branch of the common hepatic artery off of the celiac artery) to provide a constant reference point from which to position an ablation catheter. Alternatively, the catheter could also be anchored in other branches, either individually or simultaneously, to further improve control. Simultaneous anchoring may be achieved by means of a compliant, inflatable balloon (e.g., having a shape and size configured to match an osteum or another portion of a particular vessel), which may substantially occlude the vascular lumen (e.g., osteum), thereby anchoring the catheter and providing increased stability. Such an approach may obviate the need for angiography to map the course of treatment, including the concomitant deleterious contrast agent and x-ray exposure, because treatment guidance can be performed relative to a reference angiogram, with distance of the neuromodulation catheter from the guide catheter measured outside of the patient. In some embodiments, the inflatable balloon may have a size and shape configured to engage multiple ostia or to be anchored in multiple branches.

The anatomy of the vascular branches distal of the celiac plexus may be highly disparate between subjects and variations in the course of the sympathetic and parasympathetic nerves tend to be associated predominantly with branches distal of the celiac plexus, rather than being associated with any specific distance distally along the hepatic artery. In some embodiments, a neuromodulation location is selected based on a position relative to the branching anatomy rather than on any fixed distance along the hepatic artery in order to target the sympathetic nerve fibers; for example, within the common hepatic artery and about 1 cm-6 cm (e.g., about 2 cm-3 cm, or substantially at the midpoint of the common hepatic artery) from the branching of the celiac axis.

Parasympathetic and sympathetic nerve fibers tend to have opposing physiologic effects, and therefore, in some embodiments, only the sympathetic nerve fibers and not the parasympathetic nerve fibers are disrupted (e.g., denervated, ablated) in order to achieve the effects of reducing endogenous glucose production and increasing hepatic and peripheral glucose storage. In some embodiments, only the parasympathetic nerve fibers and not the sympathetic nerve fibers are stimulated in order to achieve the effects of reducing endogenous glucose production and increasing hepatic and peripheral glucose storage. In some embodiments, the sympathetic nerve fibers are denervated while the parasympathetic nerve fibers are simultaneously stimulated in order to achieve the effects of reducing endogenous glucose production and increasing hepatic and peripheral glucose storage. In some embodiments, the denervation of the sympathetic nerve fibers and the stimulation of the parasympathetic nerve fibers are performed sequentially.

In accordance with several embodiments, methods of therapeutic neuromodulation for preventing or treating disorders (such as diabetes mellitus) comprise modulation of nerve fibers (e.g., the sympathetic nerve fibers of the hepatic plexus). In one embodiment, neuromodulation decreases hepatic glucose production and/or increases hepatic glucose uptake, which in turn can result in a decrease of blood glucose levels. Disruption of the nerve fibers can be effected by ablating, denervating, severing, destroying, removing, desensitizing, disabling, reducing, crushing or compression, or inhibiting neural activity through, blocking, or otherwise modulating (permanently or temporarily) the nerve fibers or surrounding regions. In some embodiments, the disruption is carried out using one or more energy modalities. Energy modalities include, but are not limited to, microwave, radiofrequency (RF) energy, thermal energy, electrical energy, ultrasonic energy, focused ultrasound such as high-intensity or low-intensity focused ultrasound, laser energy, phototherapy or photodynamic therapy (e.g., in combination with one or more activation agents), ionizing energy delivery (such as X-ray, proton beam, gamma rays, electron beams, and alpha rays), cryoablation, and chemoablation, or any combination thereof. In some embodiments, the disruption of the sympathetic nerve fibers is carried out by chemicals or therapeutic agents (for example, via drug delivery), either alone or in combination with an energy modality. In some embodiments, ionizing energy is delivered to a target region to prevent regrowth of nerves.

In accordance with several embodiments disclosed herein, the invention comprises modulation of nerve fibers instead of or in addition to nerve fibers in the hepatic plexus to treat diabetes or other metabolic conditions, disorders, or other diseases. For example, sympathetic nerve fibers surrounding the common hepatic artery proximal to the proper hepatic artery, sympathetic nerve fibers surrounding the celiac artery (e.g., the celiac ganglion or celiac plexus, which supplies nerve fibers to multiple organs including the pancreas, stomach, and small intestine), sympathetic nerve fibers that innervate the pancreas, sympathetic nerve fibers that innervate fat tissue (e.g., visceral fat), sympathetic nerve fibers that innervate the adrenal glands (e.g., the renal plexus or suprarenal plexus), sympathetic nerve fibers that innervate the gut, stomach or small intestine (e.g., the duodenum), sympathetic nerve fibers that innervate brown adipose tissue, sympathetic nerve fibers that innervate skeletal muscle, the vagal nerves, the phrenic plexus or phrenic ganglion, the gastric plexus, the splenic plexus, the splanchnic nerves, the spermatic plexus, the superior mesenteric ganglion, the lumbar ganglia, the superior or inferior mesenteric plexus, the aortic plexus, or any combination of sympathetic nerve fibers thereof may be modulated in accordance with the embodiments herein disclosed. In some embodiments, instead of being treated, these other tissues are protected from destruction during localized neuromodulation of the hepatic plexus. In some embodiments, one or more sympathetic nerve fibers (for example, a ganglion) can be removed (for example, pancreatic sympathectomy). The nerves (sympathetic or parasympathetic) surrounding the various organs described above may be modulated in a combined treatment procedure (either simultaneously or sequentially).

In some embodiments, modulation of the nerves (e.g., sympathetic denervation) innervating the stomach results in reduction of ghrelin secretion and greater satiety, decreased sympathetic tone leading to increased motility and/or faster food transit time, thereby effecting a "neural gastric bypass." In some embodiments, modulation of the nerves (e.g., sympathetic denervation) innervating the pylorus results in decreased efferent sympathetic tone, leading to faster transit time and effecting a "neural gastric bypass." In some embodiments, modulation of the nerves (e.g., sympathetic denervation) innervating the duodenum results in disrupted afferent sympathetic activity leading to altered signaling of various receptors and hormones (e.g., GLP-1, GIP, CCK, PYY, 5-HT), thereby causing increased insulin secretion and insulin sensitivity, and/or decreased efferent sympathetic tone leading to faster transit time, thereby effecting a "neural duodenal bypass."

In some embodiments, modulation of the nerves (e.g., sympathetic denervation) innervating the pancreas results in decreased efferent sympathetic tone, thereby causing increased beta cell insulin production and beta cell mass, and decreased alpha cell glucagon production. In some embodiments, modulation of the afferent sympathetic nerves innervating the liver results in reflexive decreased sympathetic tone to the pancreas, GI tract, and/or muscle. In some embodiments, modulation of the afferent sympathetic nerves innervating the liver results in an increase in a hepatokine hormone with systemic effects (e.g., hepatic insulin sensitizing substance. In some embodiments, stimulation of the common hepatic branch of the vagus nerves could result in similar effects.

II. Types of Neuromodulation

A. Mechanical Neuromodulation

The selective modulation or disruption of nerve fibers may be performed through mechanical or physical disruption, such as, but not limited to, cutting, ripping, tearing, or crushing. Several embodiments of the invention comprise disrupting cell membranes of nerve tissue. Several embodiments involve selective compression of the nerve tissue and fibers. Nerves being subjected to mechanical pressure, such as, but not limited to, selective compression or crushing forces may experience effects such as, but not limited to, ischemia, impeded neural conduction velocity, and nervous necrosis. Such effects may be due to a plurality of factors, such as decreased blood flow.

In several embodiments, many of the effects due to selective compression or mechanical crushing forces are reversible. Beyond using mechanical compression to selectively and reversibly modulate neural response, mechanical compression may be used to permanently modulate neural response through damage to select myelin sheaths and individual nerve fascicles. In some embodiments, the level of neural modulation is tuned by modulating the mechanical compressive forces applied to the nerve. For example, a large compressive force applied to a nerve may completely inhibit neural response, while a light compressive force applied to the same nerve may only slightly decrease neural response. In some embodiments, a mechanical compressive force or crushing force may be applied to a nerve, such as a sympathetic nerve in the hepatic plexus, with a removable crushing device. In some embodiments, the removable crushing device is removed and replaced with a stronger or weaker removable crushing device depending on the individual needs of the subject (e.g., the strength of the removable crushing device being keyed to the needed neural response levels). The ability of such removable crushing devices to be fine-tuned to selectively modulate neural response is advantageous over the binary (e.g., all or nothing) response of many types of neural ablation.

In various embodiments, the compressive or crushing forces necessary to compress or crush nerves or cause ischemia within the hepatic artery or other vessels may range from about 1 to about 100 $g/mm^2$, from about 1 $g/mm^2$ to about 10 $g/mm^2$, from about 3 $g/mm^2$ to about 5 $g/mm^2$ (e.g., 8 $g/mm^2$), from about 5 $g/mm^2$ to about 20 $g/mm^2$, from about 10 $g/mm^2$ to about 50 $g/mm^2$, from about 20 $g/mm^2$ to about 80 $g/mm^2$, from about 50 $g/mm^2$ to about 100 $g/mm^2$, or overlapping ranges thereof. These compressive forces may be effected by the various embodiments of mechanical neuromodulation devices or members described herein.

Figure 4A:
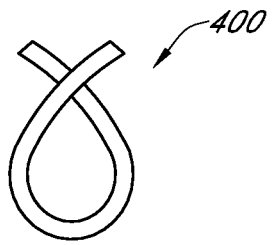
FIGS. 4A-4C, 5A and 5B, 6 and 7 illustrate embodiments of compression members configured to facilitate modulation of nerves.
Figure 4B:
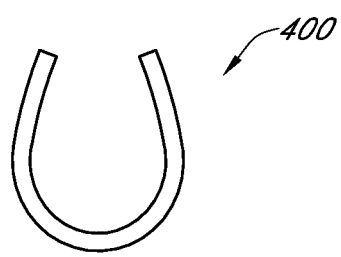
Figure 4C:
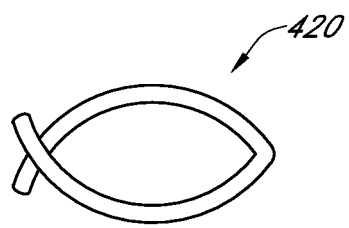

FIGS. 4A-4C, 5A, 5B, 6 and 7 illustrate various embodiments of mechanical neuromodulation devices or members. FIGS. 4A-4C illustrate embodiments of a shape memory compression clip 400. In some embodiments, the shape memory compression clip 400 is used to mechanically compress target nerves. In some embodiments, the shape memory compression clip 400 is removable. FIG. 4A illustrates a resting conformation of the shape memory compression clip 400. FIG. 4B illustrates a strained conformation of the shape memory compression clip 400, which looks like a capital "U" in the illustrated embodiment The shape memory compression clip 400 may be applied to a nerve, such as a nerve of the hepatic plexus by forcibly placing the shape memory compression clip 400 in its strained conformation, placing the target nerve in the bottom well of the shape memory compression clip 400, and then allowing the shape memory compression clip 400 to return to its resting conformation, thereby applying the desired compressive forces to the target nerve by causing it to be crushed or pinched. FIG. 4C illustrates an alternative embodiment of a shape memory compression clip 420 in which the bottom well forms an acute bend instead of being curvate when in a resting shape. The compression clip 400, 420 may be allowed to return to a resting configuration through either removal of external forces biasing the compression clip in a strained configuration (e.g., utilizing superelastic properties of shape memory materials) or heating the compression clip above a transition temperature, thereby allowing the compression clip to assume a native or resting configuration in an austenitic phase above the transition temperature.

In some embodiments, mechanical compressive forces are held at substantially constant levels after application. In some embodiments, the shape memory compression clip 400 may be tailored to the anatomy of different target nerves. In some embodiments, the shape memory compression clip 400 varies in size or shape to compensate for anatomical variance. In some embodiments, varying sizes or shapes of shape memory compression clips may be used, in addition to compensating for anatomical variance, to selectively apply varying levels of compressive stresses to the target nerve (e.g., smaller clip or stronger material for higher forces and larger clip or weaker material for smaller forces). In one embodiment, the shape memory material is nitinol. In various embodiments, the shape memory material is a shape memory polymer or any other appropriate material having shape memory material properties. In some embodiments, compression members comprise simple spring clips or any other devices capable of applying a substantially constant force. In some embodiments, a compression member is configured to clamp the entire artery and the nerves in the adventitial layer, thereby applying the desired compressive forces to both the target nerves and the artery around which the target nerves travel.

Applying compressive forces to hepatic arteries is uniquely feasible, in some embodiments, because the liver is supplied with blood from both the hepatic arteries, around which many of the target nerves described herein may travel, as well as the portal vein. If at least one of the hepatic arteries is clamped (for the purpose of applying compressive forces to the nerves in its adventitia), the liver would lose the blood supply from that artery, but would be fully supplied by the portal vein, thereby leaving the liver viable and healthy.

In some embodiments, mechanical compressive forces are variable across time following application. In some embodiments, the mechanical compressive forces are varied according to a pre-set duty cycle, thereby titrating the effects of the neuromodulation. One or more embodiments may comprise a transcutaneous delivery of energy to a circuit coupled to a compression member (e.g., a nitinol clip) having a transition between martensitic and austenitic states at a specific temperature induced by a temperature that is substantially different from body temperature. In several embodiments, a variance in temperature is provided through, but is not limited to: a thermocouple (e.g., a Peltier junction) thermally coupled to the compression member to which the circuit may apply power, or a heating element thermally coupled to the compression member to which the circuit may apply resistive power, thereby altering the physical conformation of the compression member and varying (either increasing or decreasing depending on the power applied) the compressive forces generated by the compression member. In one embodiment, the compression member itself acts as a resistive element and the circuit is coupled directly to the compression member to apply resistive power to the compression member, thereby altering the physical conformation of the compression member and varying (either increasing or decreasing depending on the power applied) the compressive forces generated by the compression member. Other embodiments combine the compression member with a thermocouple to allow the selective application of electric power to vary the compressive stresses created by the compression member.

Figure 5A:
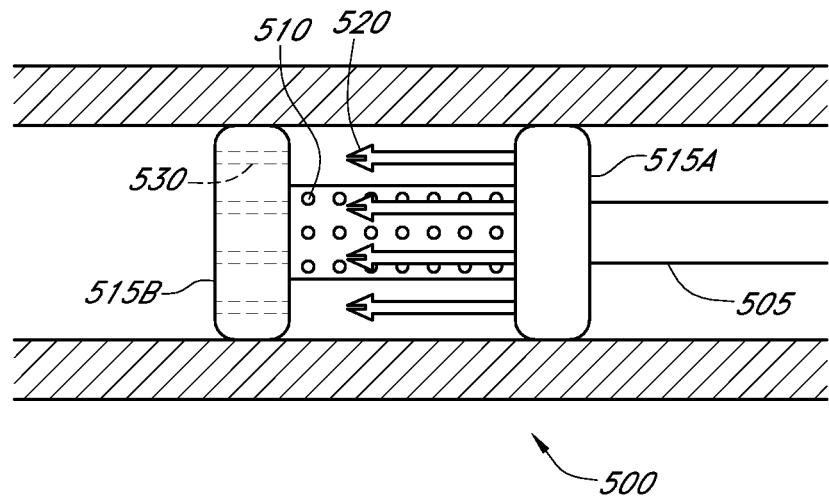
Figure 5B:
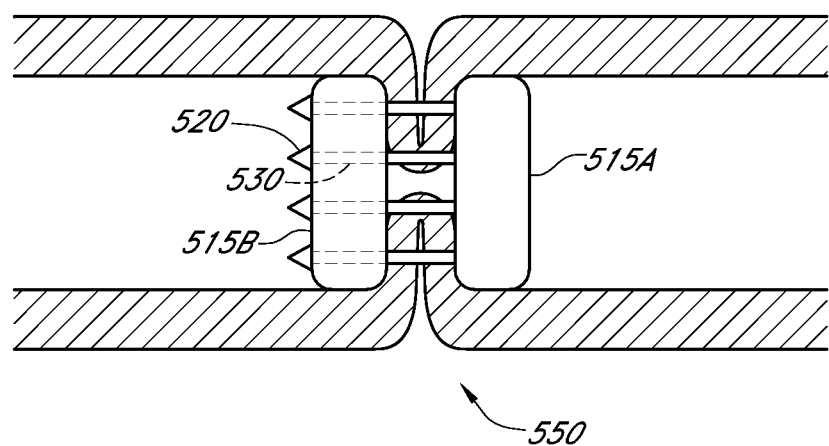

FIGS. 5A and 5B illustrate another embodiment of a compression device. FIG. 5A illustrates a catheter-based vascular wall compression system 500 including a vascular wall clamp 515 in an open conformation. The catheter-based vascular wall compression system 500 includes a detachable insertion catheter 505, suction holes 510, an engagement portion 515A of the vascular wall clamp 515, an anchoring mechanism 520, a receiving portion 515B of the vascular wall clamp, and an anchoring mechanism accepting portion 530. In operation, the vascular wall clamp 515 may be inserted into the target vessel on the distal end of the detachable insertion catheter 505. In one embodiment, the receiving portion 515B of the vascular wall clamp 515 is located at the distal end of the detachable insertion catheter 505, while the engagement portion 515A of the vascular wall clamp 515 is located slightly proximal to the receiving portion 515B. The surface of the detachable insertion catheter 505 between the receiving portion 515B and the engagement portion 515A may include a plurality of suction holes 510.

In further operation, once the vascular wall clamp 515 is placed at the desired target location, the suction holes 510, in one embodiment, create a vacuum, or suction, which brings the walls of the target vessel in substantially direct apposition to the surface of the detachable insertion catheter portion that includes the plurality of suction holes 510. While maintaining suction, and therefore the position of the vessel wall in apposition to the detachable insertion catheter 505, the engagement portion 515A is moved toward the receiving portion 515B (or vice versa), thereby pinching the vascular wall which remained in direct apposition to the detachable insertion catheter between the receiving portion 515B and the engagement portion 515A.

The anchoring mechanism 520, which is attached to the engagement portion 515A engages the anchoring member accepting portion 530 of the receiving portion 515B, thereby securing the receiving portion 515B to the engagement portion 515A and clamping the vascular wall portion that remains in direct apposition to the detachable insertion catheter 505 between the receiving portion 515B and the engagement portion 515A. Once the receiving portion 515B has fully engaged with the engagement portion 515A, the detachable insertion catheter 505 may be disengaged from the vascular wall clamp 515 and removed by the same path it was inserted.

FIG. 5B illustrates the vascular wall clamp 515 in a closed conformation. In FIG. 5B, the anchoring mechanism 520, which is attached to the engagement portion 515A of the vascular wall clamp 515 has engaged the anchoring member accepting portion 530 of the receiving portion 515B of the vascular wall clamp 515, thereby clamping a portion of the vascular wall between the receiving portion 515B and the engagement portion 515A. FIG. 5B shows that the detachable insertion catheter 505 has already been removed.

In some embodiments, the engagement portion 515A and the receiving portion 515B of the vascular wall clamp 525 both include a hollow center. In these embodiments, when the detachable insertion catheter 505 is removed, the hole at the center of the engagement portion 515A of the vascular wall clamp 515 and the hole at the center of the receiving portion 515B of the vascular wall clamp 525 creates a patent lumen between the receiving portion 515B and the engagement portion 515A, thereby allowing continued blood flow from one side to the other. In some embodiments, the detachable insertion catheter 505 is attached to either the engagement portion 515A or the receiving portion 515B of the vascular wall clamp 515 by means of a threaded portion, which may be unthreaded once the receiving portion 515B and engagement portion 515A have engaged, and the detachable insertion catheter 505 is no longer needed.

In some embodiments, the vascular wall clamp 515 is inserted to the target anatomy using an over-the-wire approach. In some embodiments, the detachable insertion catheter 505 is hollow and has suction holes 510 in communication with an internal hollow lumen of the detachable insertion catheter 505. The suction holes 510 may be a series of small openings, a screen, or any other structure which allows a lower pressure area to be created between the receiving portion 515B and the engagement portion 515A of the vascular wall clamp 515 to bring the vessel wall and perivascular tissue in substantially direct apposition with the detachable insertion catheter 505. In some embodiments, the vascular wall clamp 515 is deployed by pulling proximally on the detachable insertion catheter 505, thereby bringing the distal receiving portion 515B of the vascular wall clamp 525 into engagement with the proximal engagement portion 515A of the vascular wall clamp 515, thereby compressing and/or severing arterial and nerve tissue captured therein. In some embodiments, rotation of the catheter 505 is effective to disengage the catheter 505 from the vascular wall clamp 515. In some embodiments, removal of the detachable insertion catheter 505 from the vascular wall clamp 515 leaves a patent lumen permitting blood flow to the liver.

In some embodiments, the engagement mechanism 520 comprises at least one spear-shaped clip and the engagement accepting portion 530 comprises at least one hole aligned to accept the at least one spear shaped clip and to engage the two the at least one spear shaped clip engagement mechanism 520 enters the at least one hole engagement accepting portion 530 and snaps into place. In some embodiments, the engagement mechanism 520 and engagement accepting portion 530 are simply magnets which hold the receiving portion 515B of the vascular wall clamp 515 and the engagement portion 515A of the vascular wall clamp 515 together. In still other embodiments, the engagement mechanism 520 and the engagement accepting portion 530 are any structures that allow the engagement portion 515A to engage the receiving portion 515B and remain in that engaged conformation. In some embodiments, the vascular wall clamp 515 comprises a biologically inert material with decreased thrombogenicity, such as Teflon®.

Figure 6:
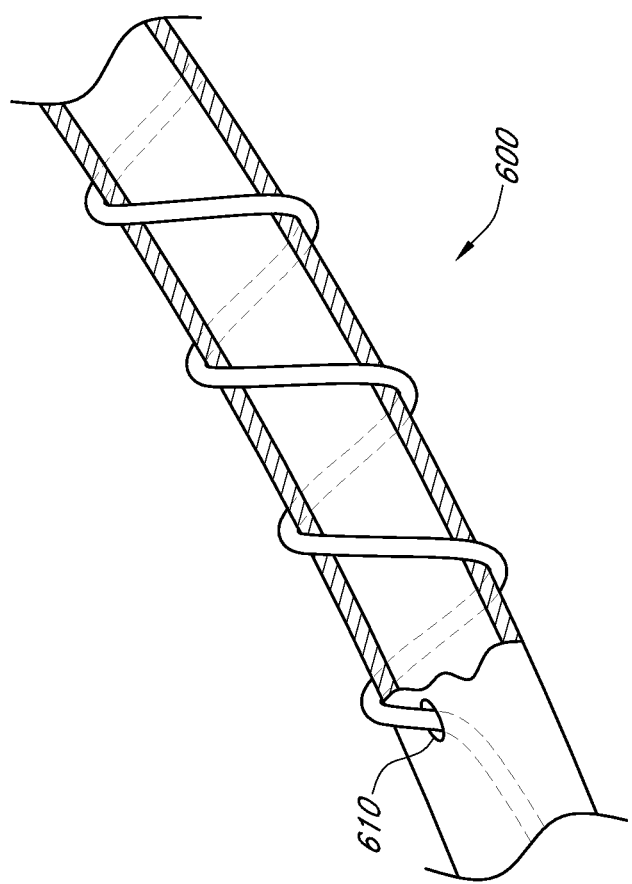

FIG. 6 illustrates an embodiment of an extravascular compression coil 600 inserted within a vessel. In operation, the extravascular compression coil 600 may be advanced through a hole in the vascular wall 610 in a spiraling intra-vascular to extra-vascular manner into the vessel adventitia, thereby placing the extravascular compression coil 600 around the target vessel. In some embodiments, the extravascular compression coil 600 has the effect of compressing the nerves located within the vascular wall of the target vessel. In some embodiments, to prevent occlusion and stenosis, an intravascular stent is subsequently placed within the lumen of the target vessel, thereby both propping open the vessel for continued flow and providing a resilient surface against which the target nerves may be compressed.

In embodiments where stenosis is of particular concern, a stent is placed in the target vessel after treatment to retain patency. In some embodiments, the placement of a stent within the lumen of the target vessel provides the added benefit of compressing the vascular wall to a higher degree, thereby disrupting the target nerves even more. In some embodiments, a stent is placed in the portal vein due to the risk of portal vein stenosis from hepatic arterial ablation procedures. In some embodiments, to protect the portal vein from possible stenosis, anal cooling is used because the gut venous flow travels to the portal system (in some embodiments, anal cooling has the direct result of cooling the portal vein and decreasing the likelihood of stenosis due to treatment of the hepatic artery).

In some embodiments, magnets may be delivered separately into the portal vein and hepatic artery. Upon placement of the two magnets, opposite poles of the two magnets will attract each other and subsequently mate, thereby resulting in substantial compression of the nerves disposed between the two magnets. The force created by the mating of the two magnets may be selectively modulated by increasing or decreasing the strength of magnets used for any given patient morphology, as desired or required.

Figure 7:
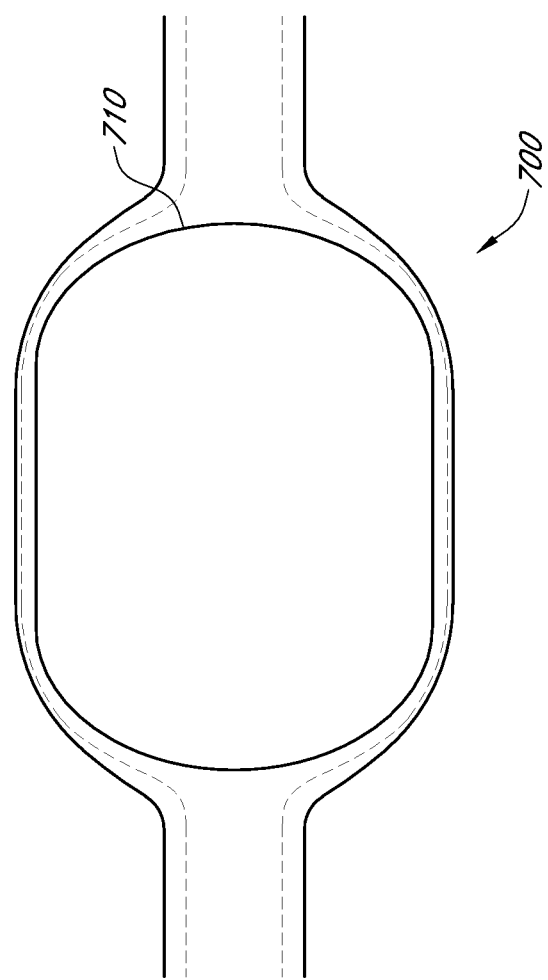

FIG. 7 illustrates an embodiment of a fully occluding balloon 700 inserted within a target blood vessel. In operation, a fully occluding balloon 710 is inserted into a target vessel, inflated and used to expand or stretch the vascular lumen to sufficiently stretch the surrounding nerves to either the point of ischemia or physical disruption. The fully occluding balloon 710 may be removed after physical disruption or after the target nerves have been destroyed due to ischemia. Alternatively, the fully occluding balloon 710 may be left in place permanently because, as discussed previously, the liver is supplied by blood from the portal vein as well, rendering the hepatic artery at least somewhat redundant. In some embodiments, the level of balloon compression is adjusted in an ambulatory fashion, thereby allowing for titration of the neuromodulation effect.

In some embodiments, rather than using a fully occluding balloon 710, a non-occluding balloon or partially occluding balloon is inserted into a target vessel, inflated, and used to expand or stretch the vascular lumen to sufficiently stretch the surrounding nerves to the point of ischemia or physical disruption. The non-occluding or partially occluding balloon may have similar structural features as the fully occluding balloon 710, but may include at least one hollow lumen (e.g., a central lumen) to allow for continued blood flow after placement. In some embodiments, the level of balloon compression can be adjusted in an ambulatory fashion, thereby allowing for titration of the neuromodulation effect.

In some embodiments, similar to the occlusion techniques described above, a balloon catheter may be inserted into the target vessel and then filled with a fluid which is infused and withdrawn at a specific frequency (e.g., pressurized in an oscillating fashion), thereby causing mechanical disruption of the nerve fibers surrounding the target vessel (e.g., hepatic artery). In some embodiments, the fluid used to fill the balloon catheter may be a contrast agent to aid in visualization of the arterial structure (and thereby limiting the amount of contrast agent used in the procedure).

In some embodiments, a fluid is injected into the interstitial space surrounding the vasculature around which the target nerve lies, thereby applying compressive forces to the nerve bundle which surrounds the vessel(s). In some embodiments, the fluid is air. In some embodiments, the fluid is any noble gas (e.g., heavy gas), including but not limited to: helium, neon, argon, krypton, and xenon. In some embodiments, the fluid is nitrogen gas. In some embodiments, the fluid is any fluid capable of being injected to apply the desired compressive forces. In some embodiments, the fluid is injected by a catheter inserted transluminally through a blood vessel in substantially close proximity to the target site (e.g., location where nervous compression is desired). In some embodiments, the fluid is injected by a needle or trocar inserted transdermally through the skin and surrounding tissues to the target site. Any method of fluid injection may be used to deliver the requisite amount of fluid to the target site in order to create compressive forces that are applied to the target nerve, such as nerves of the hepatic plexus.

In some embodiments, a target vessel is completely transected, thereby causing a complete and total physical disruption of the vessel wall and the surrounding nerves in the adventitial tissues. The target vessel may then be re-anastamosed, thereby allowing continued perfusion through the vessel. The nerve tissue either does not reconnect, or takes a significant amount of time to do so. Therefore, all neural communication surrounding the transected vessel may temporarily or permanently the disrupted. In some embodiments, a cutting device is advanced in a catheter through the subject's vasculature until it reaches a target vessel. The cutting device may then be twisted along the axis of the target vessel to cut through the target vessel from the inside out. In some embodiments, an expandable element, such as a balloon catheter, is inserted into the vessel to compress the vessel wall and provide a controlled vessel thickness to permit transection. A rotational cutter may then be advanced circumferentially around the expandable element to effect transection of the vessel and the nerves disposed within the adventitia of the vessel. In one embodiment, the target vessel is transected during open surgery.

Re-anastomoses of vessels could be achieved using any of several methods, including laser, RF, microwave, direct thermal, or ultrasonic vessel sealing. In some embodiments, thermal energy may be delivered through an expandable element to effect anastomosis of the vessel under the mechanical pressure provided by the expandable element. The combination of pressure, time, and temperature (e.g., 60° C., 5 seconds, and 120 psi in one embodiment) may be an effective means to seal vessels such as the hepatic arteries.

B. Catheter-Based Neuromodulation

In accordance with some embodiments, neuromodulation (e.g., the disruption of sympathetic nerve fibers) is performed using a minimally invasive catheter system, such as an ablation catheter system. In some embodiments, an ablation catheter system for ablating nerve fibers is introduced using an intravascular (e.g., intra-arterial) approach. In one embodiment, an ablation catheter system is used to ablate sympathetic nerve fibers in the hepatic plexus. As described above, the hepatic plexus surrounds the proper hepatic artery, where it branches from the common hepatic artery. In some embodiments, the ablation catheter system is introduced via an incision in the groin to access the femoral artery. The ablation catheter system may be advanced from the femoral artery to the proper hepatic artery via the iliac artery, the abdominal aorta, the celiac artery, and the common hepatic artery. In other embodiments, any other suitable percutaneous intravascular incision point or approach is used to introduce the ablation catheter system into the arterial system (e.g., a radial approach via a radial artery or a brachial approach via a brachial artery).

In some embodiments, the catheter may be placed into the target region substantially close to the target nerve through percutaneous injection. Using such a percutaneous placement may allow less destructive, less invasive selective destruction or disruption of the target nerve.

In some embodiments, the catheter system comprises a visualization device substantially close to the distal end of the catheter. The visualization device may promote nervous visualization, thereby possibly allowing higher levels of precision in targeted nervous disruption. In some embodiments, the catheter system comprises a light source configured to aid in visualization. In some embodiments, a light source and a visualization device (such as a camera) are used in tandem to promote visibility. In some embodiments, the catheter system comprises a distal opening out of which active elements (such as any camera, light, drug delivery port, and/or cutting device, etc.) are advanced. In some embodiments, the catheter system comprises a side opening out of which the active elements (such as any camera, light, drug delivery port, and/or cutting device, etc.) may be advanced, thereby allowing the user to access the vessel wall in vessels with tortuous curves and thereby allowing nerve destruction with the axis of the catheter aligned parallel to the vessel.

Animal studies have shown that the force of electrode contact against the vessel wall may be a critical parameter for achieving ablative success in some embodiments. Therefore, ablation catheter devices may advantageously not only be small enough to access the target vasculature, but also to incorporate low-profile features for facilitating sufficient electrode contact pressure during the length of the treatments.

In some embodiments, the catheter of the catheter system has a diameter in the range of about 2-8 Fr, about 3-7 Fr, about 4-6 Fr (including about 5 Fr), and overlapping ranges thereof. The catheter may have a varying diameter along its length such that the distal portion of the catheter is small enough to fit into progressively smaller vessels as the catheter is advanced within vasculature. In one embodiment, the catheter has an outside diameter sized to fit within the common hepatic artery (which may be as small as about 1 mm) or the proper hepatic artery. In some embodiments, the catheter is at least about 150 cm long, at least about 140 cm long, at least about 130 cm long, at least about 120 cm long, at least about 110 cm long, at least about 100 cm long, or at least about 90 cm long. In some embodiments, the flexibility of the catheter is sufficient to navigate tortuous hepatic arterial anatomy having bend radii of about 10 mm, about 9 mm, about 8 mm, about 7 mm, about 6 mm, about 5 mm, about 4 mm, about 3 mm, about 2 mm, about 1 mm, or about 0.5 mm.

In accordance with several embodiments, catheters of the catheter-based systems described herein have steerable, precurved, deflectable or flexible distal tip components or distal segments. The deflectability or flexibility may advantageously bias an energy applicator against the arterial wall to ensure effective and/or safe delivery of therapy, permit accurate positioning of the energy applicator, maintain contact of an energy delivery element against a vascular wall maintain sufficient contact pressure with a vascular wall, and/or help navigate the catheter to the target anatomy. In some embodiments, catheters with steerable, curvable or articulatable or distal portions provide the ability to cause articulation, bending, or other deployment of the distal tip (which may contain an ablation element or energy delivery element) even when a substantial portion of the catheter remains within a guide catheter. In some embodiments, the neuromodulation catheters provide the ability to be delivered over a guidewire, as placing guide catheters may be unwieldy and time-consuming to navigate.

In various embodiments, the contact force exerted on the vessel wall to maintain sufficient contact pressure is between about 1 g to about 500 g, from about 20 g to about 200 g, from about 10 g to about 100 g, from about 50 g to about 150 g, from about 100 g to about 300 g, from about 200 g to about 400 g, from about 300 g to about 500 g, or overlapping ranges thereof. In some embodiments, the same ranges may be used but expressed as $g/mm^2$ numbers. The contact pressures described above may be achieved by any of the neuromodulation (e.g., ablation) devices and systems described herein.

Figure 8:
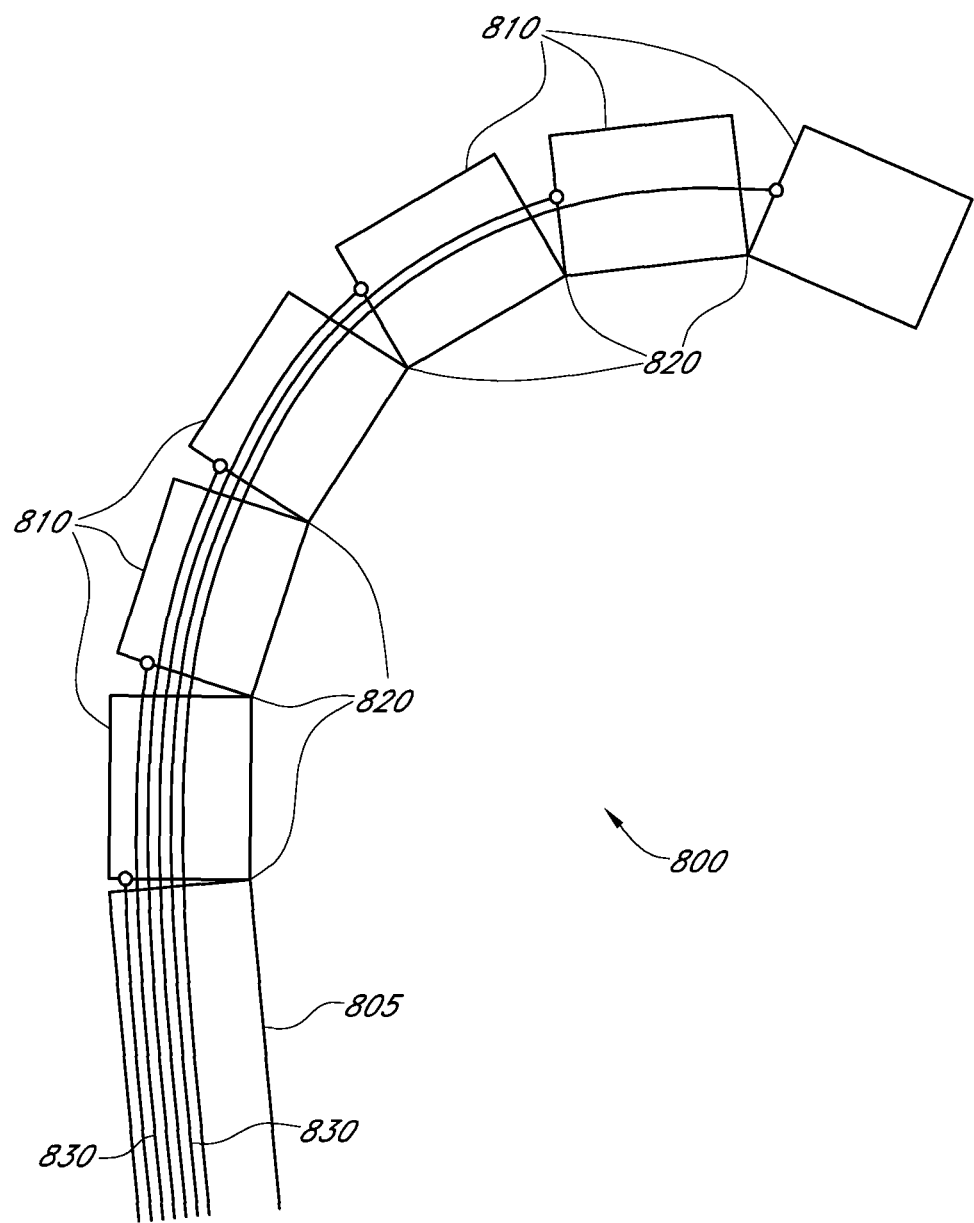
FIGS. 8 and 9 illustrate embodiments of neuromodulation catheters.

FIG. 8 illustrates an embodiment of a steerable neuromodulation catheter 800 having an articulatable tip. The neuromodulation catheter 800 comprises a catheter body 805, multiple segments 810, multiple corresponding hinges 820, and multiple corresponding articulation wires 830. In some embodiments, the neuromodulation catheter 800 includes fewer than six segments, hinges, and/or articulation wires (e.g., two, three, four, or five). In some embodiments, the neuromodulation catheter 800 includes more than six segments, hinges, and/or articulation wires (e.g., seven, eight, nine, ten, eleven to twenty, or more than twenty). In one embodiment, the segments 810 and the hinges 820 are hollow.

Each of the segments 810 is coupled to adjacent segment(s) by one of the hinges 820. Each of the articulation wires is attached to one of the segments and passes from the segment to which it is attached through the other segments toward the catheter body 805. In operation, the articulation wires may be extended or retracted as desired, thereby pivoting the articulatable tip of the catheter 800.

In some embodiments, all of the articulation wires 830 are extended and retracted in combination. In other embodiments, each of the articulation wires 830 is individually actuatable. In such embodiments, each individual segment 810 could be individually actuatable by each corresponding articulation wire 830. For example, even when the third segment, the fourth segment, the fifth segment, and the sixth segment are constrained within a guide catheter, the first segment and the second segment may be articulated by extending or retracting the first articulation wire and/or the second articulation wire, respectively, with sufficient force. The steerable catheter 800 may advantageously permit improved contact pressure between the distal tip of the steerable catheter 800 and the vascular wall of the target vessel, thereby improving treatment efficacy.

Figure 9:
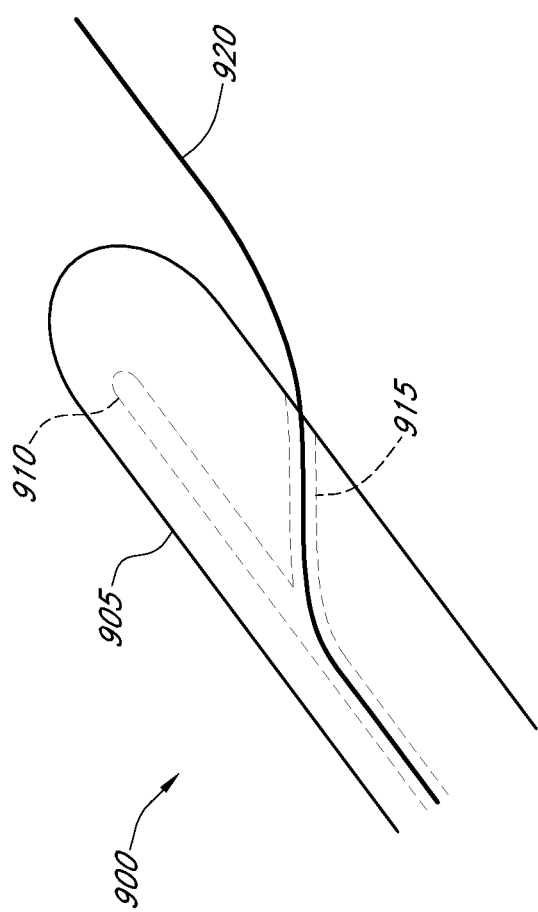

FIG. 9 illustrates an embodiment of a neuromodulation catheter 900 with a deflectable distal tip. The neuromodulation catheter 900 comprises a guidewire configured to facilitate steerability. The neuromodulation catheter 900 includes an ablation catheter tip 905, a guidewire housing 910, a guide wire channel 915, and a guidewire 920. In operation, the guidewire 920 may be extended out through guide wire channel 915 to be used in its guiding capacity to navigate through vasculature. When it is not desirable to use the guidewire 920 in its guiding capacity, the guide wire 920 may be retracted into the ablation catheter tip 905 and then extended into the guide wire housing 910, where it may be stored until needed or desired.

In some embodiments, the guidewire 920 is plastically deformable with a permanent bend in the distal tip. In such embodiments, the guidewire 920 may be rotated within the body of the neuromodulation catheter 900 to plastically deform and be pushed into the guide wire housing 910, or may be rotated 180 degrees and regain its bent configuration to exit through the guide wire channel 915. In some embodiments, a thermocouple temperature sensor may be incorporated into the guide wire 920. In some embodiments, the guide wire 920 is used to deliver ablative energy (such as RF energy) to at least one electrode. In one embodiment, delivery of the ablative energy is facilitated by disposing a conductive gel between the guidewire and the at least one ablation electrode.

In some embodiments, a catheter system is configured to extravascularly and selectively disrupt target nerves. In some embodiments, a catheter is advanced through a cardiovascular system, such as described above, to the target site. The catheter may be passed transluminally to the extravascular space or may create a virtual space between the vascular media and adventitia of the vessel. In some embodiments, the catheter, once positioned at the desired location is activated to selectively modulate or disrupt the target nerve or nerves. The selective disruption may be accomplished or performed through chemo-disruption, such as supplying any type of nerve destroying agent, including, but not limited to, neurotoxins or other drugs detrimental to nerve viability. In some embodiments, selective disruption is performed through energy-induced disruption, such as thermal or light ablation (e.g., radiofrequency ablation, ultrasound ablation, or laser ablation). In one embodiment, a camera or other visualization device (e.g., fiberoptic scope) is disposed on a distal end of the catheter to ensure that nerves are targeted and not surrounding tissue. If a target location is adjacent the branch between the common hepatic artery and the proper hepatic artery, a less acute catheter bend may be required due to the angulation between the bifurcation of the common hepatic artery and the proper hepatic artery. In some embodiments, the catheter comprises a side port, opening or window, thereby allowing for delivery of fluid or energy to denervate or ablate nerves with the longitudinal axis of the catheter aligned parallel or substantially parallel to the target vessel portion. In some embodiments, the catheter or probe is inserted percutaneously and advanced to the target location for extravascular delivery of energy or fluid.

C. Energy-Based Neuromodulation

1. Radiofrequency

In some embodiments, a catheter system comprises an ablation device coupled to a pulse-generating device. For example, the ablation device may be an ablation catheter. The ablation catheter may have a proximal end and a distal end. In some embodiments, the distal end of the ablation catheter comprises one or more electrodes. The one or more electrodes can be positioned on an external surface of the ablation catheter or can extend out of the distal end of the ablation catheter. In some embodiments, the electrodes comprise one or more bipolar electrode pairs. In some embodiments, the electrodes comprise one or more active electrodes and one or more return electrodes that cooperate to form electrode pairs. In some embodiments, one or more electrodes are monopolar electrodes. In some embodiments, the distal end of the ablation catheter comprises at least one bipolar electrode pair and at least one monopolar electrode. One or more electrically conductive wires may connect one or more electrodes located at the distal end of the ablation catheter to the pulse-generating device. In some embodiments, multiple electrodes can extend from the ablation catheter on multiple wires to provide multiple energy delivery locations or points within a vessel (e.g., a hepatic artery).

In some embodiments, the pulse-generating device delivers electrical (e.g., radiofrequency (RF)) signals or pulses to the electrodes located at or near the distal end of the ablation catheter. The electrodes may be positioned to deliver RF energy in the direction of sympathetic nerve fibers in the hepatic plexus to cause ablation due to thermal energy. In some embodiments, the electrodes are positioned on top of reflective layers or coatings to facilitate directivity of the RF energy away from the ablation catheter. In some embodiments, the electrodes are curved or flat. The electrodes can be dry electrodes or wet electrodes. In some embodiments, the catheter system comprises one or more probes with one or more electrodes. For example, a first probe can include an active electrode and a second probe can include a return electrode. In some embodiments, the distal ends of the one or more probes are flexible. The ablation catheter can comprise a flexible distal end. Variable regions of flexibility or stiffness are provided in some embodiments.

In one embodiment, a pair of bipolar electrodes is disposed at a location that is substantially tangential to the inner lumen of the hepatic artery, each individual electrode having an arc length of 20 degrees, with an inter-electrode spacing of 10 degrees. The edges of the two electrodes may have radii sufficient to reduce current concentrations. In some embodiments, the two electrodes are coated with a thin layer of non-conductive material to reduce current concentrations such that energy is delivered to target tissue via capacitive coupling. The arc length and spacing of the bipolar electrodes may be varied to alter the shape of the energy delivery zones and thermal lesions created by the delivery of energy from the electrodes.

In some embodiments, peripheral active or grounding conductors are used to shape an electric field. In one embodiment, a grounding needle is positioned perivascularly to direct ablative current towards nerves within the perivascular space. In a non-invasive embodiment to accomplish the same effect, high ion content material is infused into the portal vein. In another embodiment, a shaping electrode is positioned within the portal vein using percutaneous techniques such as employed in transjugular intrahepatic portosystemic (TIPS) techniques. In one embodiment, a second shaping electrode is positioned in the biliary tree endoscopically.

In some embodiments, a plurality of electrodes are spaced apart longitudinally with respect to a center axis of the ablation catheter (e.g., along the length of the ablation catheter). In some embodiments, a plurality of electrodes are spaced apart radially around a circumference of the distal end of the ablation catheter. In some embodiments, a plurality of electrodes are spaced apart both longitudinally along a longitudinal axis of the ablation catheter and radially around a circumference of the ablation catheter from each other. In various embodiments, the electrodes are positioned in various other patterns (e.g., spiral patterns, checkered patterns, zigzag patterns, linear patterns, randomized patterns).

One or more electrodes can be positioned so as to be in contact with the inner walls (e.g., intima) of the blood vessel (e.g., common hepatic artery or proper hepatic artery) at one or more target ablation sites adjacent the autonomic nerves to be disrupted or modulated, thereby providing intravascular energy delivery. In some embodiments, the electrodes are coupled to expandable and collapsible structures (e.g., self-expandable or mechanically expandable) to facilitate contact with an inner vessel wall. The expandable structures can comprise coils, springs, prongs, tines, scaffolds, wires, stents, balloons, and/or the like. The expandable electrodes can be deployed from the distal end of the catheter or from the external circumferential surface of the catheter. The catheter can also include insulation layers adjacent to the electrodes or active cooling elements. In some embodiments, cooling elements are not required. In some embodiments, the electrodes can be needle electrodes configured to penetrate through a wall of a blood vessel (e.g., a hepatic artery) to deliver energy extravascularly to disrupt sympathetic nerve fibers (e.g., the hepatic plexus). For example, the catheter can employ an intra-to-extravascular approach using expandable needle electrodes having piercing elements. The electrodes can be disposable or reusable.

In some embodiments, the ablation catheter includes electrodes having a surface area of about 2 to about 5 mm$^2$, 5 to about 20 mm$^2$, about 7.5 to about 17.5 mm$^2$, about 10 to about 15 mm$^2$, overlapping ranges thereof, less than about 5 mm$^2$, greater than about 20 mm$^2$, 4 mm$^2$, or about 12.5 mm$^2$. In some embodiments, the ablation catheter relies only on direct blood cooling. In some embodiments, the surface area of the electrodes is a function of the cooling available to reduce thrombus formation and endothelial wall damage. In some embodiments, lower temperature cooling is provided. In some embodiments, higher surface areas are used, thereby increasing the amount of energy delivered to the perivascular space, including surface areas of about 5 to about 120 mm$^2$, about 40 to about 110 mm$^2$, about 50 to about 100 mm$^2$, about 60 to about 90 mm$^2$, about 70 to about 80 mm$^2$, overlapping ranges thereof, less than 5 mm$^2$, or greater than 120 mm$^2$. In some embodiments, the electrodes comprise stainless steel, copper, platinum, gold, nickel, nickel-plated steel, magnesium, or any other suitably conductive material. In some embodiments, positive temperature coefficient (PTC) composite polymers having an inverse and highly non-linear relationship between conductivity and temperature are used. In some embodiments, PTC electrodes (such as the PTC electrodes described in U.S. Pat. No. 7,327,951, which is hereby incorporated herein by reference) are used to control the temperature of RF energy delivered to the target tissue. For example, PTC electrodes may provide high conductivity at temperatures below 60° C. and substantially lower conductivity at temperatures above 60° C., thereby limiting the effect of energy delivery to tissue above 60° C.

Figure 10:
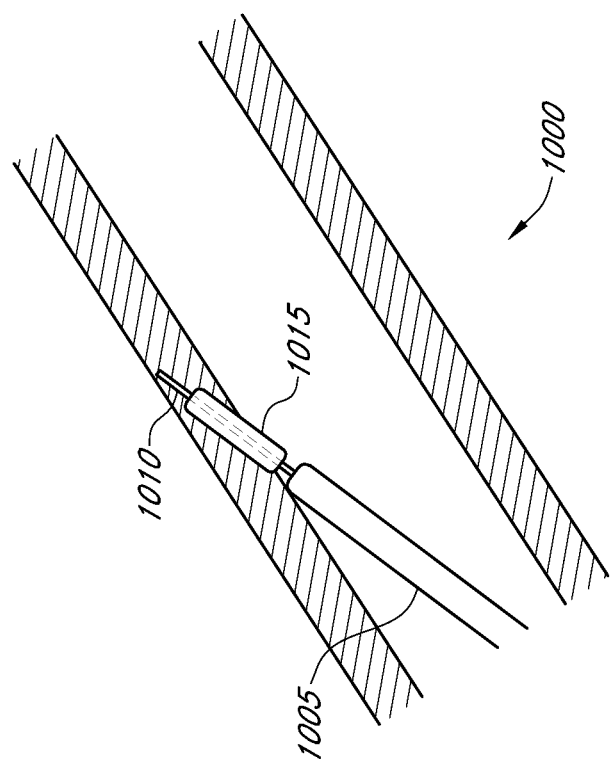
FIGS. 10 and 11 illustrate embodiments of electrode catheters.

FIG. 10 illustrates a self-repairing ablation catheter 1000. The self-repairing ablation catheter 1000 comprises a catheter body 1005, a needle electrode 1010, and a vascular wall plug 1015. In one embodiment, the needle electrode 1010 is placed at or near the distal end of the catheter body 1005 and used to heat tissue (which may result in nerve ablation). The vascular wall plug 1015 may be placed around the needle electrode 1010 such that when the needle electrode 1010 is pushed into or through the vascular wall, the vascular wall plug 1015 is pushed into or through the vascular wall as well. Upon retracting the self-repairing ablation catheter 1000, the needle electrode 1010 fully retracts in some embodiments, leaving the vascular wall plug 1015 behind, and thereby plugging or occluding the hole left by the needle electrode 1010.

In embodiments used to modulate (e.g., ablate) extravascularly, the vascular wall plug 1015 may comprise a hydrogel jacket or coating disposed on the needle electrode 1010. In some embodiments, the vascular wall plug 1015 is glued or otherwise adhered or fixed in a frangible manner at its distal end to the needle electrode 1010, yet may be sufficiently thin so it does not prevent smooth passage of the needle electrode 1010 as it is advanced into the perivascular space. In some embodiments, once the proximal end of the vascular wall plug 1015 passes out of the guiding lumen, it cannot be pulled proximally. Therefore, upon ablation completion, removal of the needle electrode 1010 from the perivascular space places the hydrogel jacket in compression in the hole made by the needle electrode 1010 in the vessel wall, thereby forming a plug which prevents or reduces the likelihood of vessel leakage or rupture. In some embodiments, the vascular wall plug 1015 is be made of a hydrogel that swells when exposed to tissues, such as polyvinyl alcohol, or a thrombogenic material, such as those employed during interventional radiology procedures to coil off non-target vessels.

Figure 11:
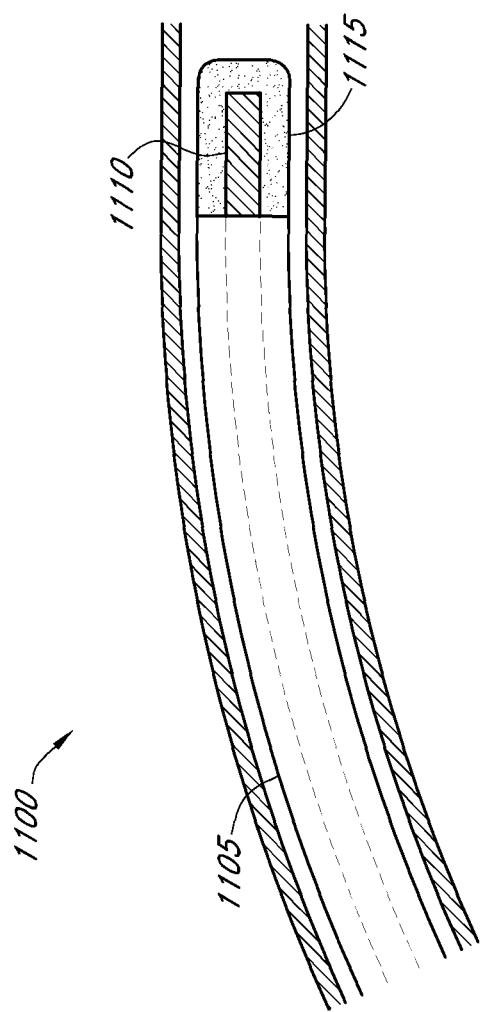

FIG. 11 illustrates an embodiment of a hydrogel-coated electrode catheter 1100. The hydrogel-coated electrode catheter 1100 includes a catheter body 1105, an ablation electrode 1110, and a hydrogel coating 1115. In one embodiment, the ablation electrode 1110 is attached to the distal end of the catheter body 1105 and the hydrogel coating 1115 coats the electrode 1110.

In some embodiments, the hydrogel coating 1115 is a previously-desiccated hydrogel. Upon insertion into the target anatomy, the hydrogel coating 1115 on the ablation electrode 1110 may absorb water from the surrounding tissues and blood. Ions drawn in from the blood (or included a priori in the hydrogel coating 1115) may impart conductive properties to the hydrogel coating 1115, thereby permitting delivery of energy to tissue. In accordance with several embodiments, the hydrogel-coated electrode catheter 1100 requires less cooling during ablation, as the hydrogel coating resists desiccation. A smaller catheter size may also be used, as construction requirements and number of components may be reduced. In some embodiments, the electrode impedance replicates native tissue impedance for better impedance matching. In some embodiments, temperature measurements at the surface of the hydrogel-coated electrode are possible.

In some embodiments, a balloon catheter comprises a catheter body and a distal balloon. The catheter body comprises a lumen configured to continuously infuse saline or other fluid into the balloon. The distal balloon comprises one or more hydrogel portions spaced around the circumference of the distal balloon. In one embodiment, if saline is used, any water that vaporizes from the surface of the distal balloon is replenished by diffusion from the balloon lumen, thereby preventing free saline to travel into the vessel interface and reducing any undesired effects of saline infusion.

In accordance with several embodiments, the branches of the forks between the common hepatic artery, the proper hepatic artery and the gastroduodenal artery are advantageously simultaneously or sequentially targeted (e.g., with RF energy) because sympathetic nerves supplying the liver and pancreas are generally tightly adhered to or within the walls of these arteries. Forks between other arteries or vessels may similarly be simultaneously or sequentially be targeted (e.g., with RF energy). In some embodiments, coiled electrodes opposing the artery walls are used.

Figure 12A:
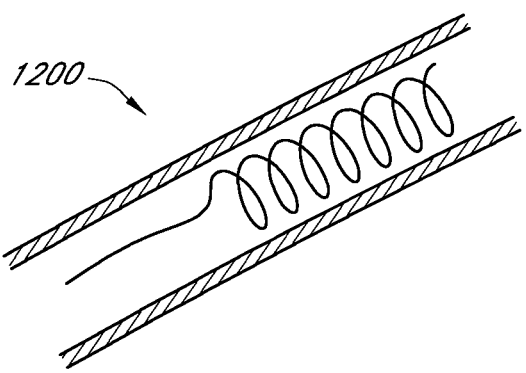
FIGS. 12A and 12B illustrate embodiments of ablation coils.

FIG. 12A illustrates an embodiment of a single ablation coil 1200 device. The single ablation coil device 1400 may be inserted into target vasculature and activated to ablate the nerves within or surrounding the vasculature. To ablate a vascular fork, it may be necessary to insert the single ablation coil 1200 into one branch of the fork (e.g., proper hepatic artery branch) and ablate that branch, then insert the single ablation coil 1200 into the other branch of the fork (e.g., gastroduodenal artery branch) and ablate that branch.

Figure 12B:
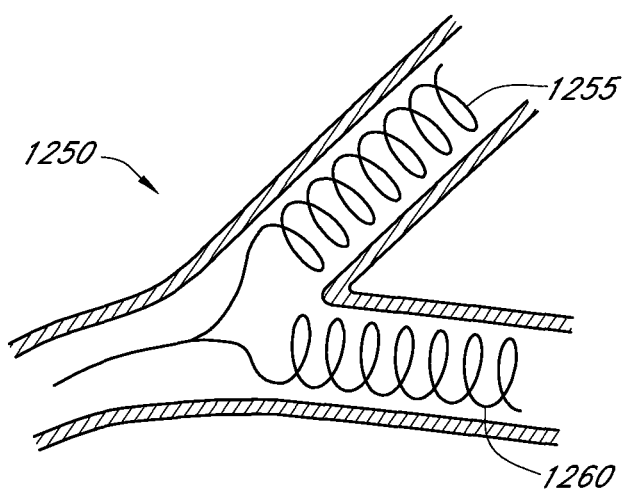

FIG. 12B illustrates a forked ablation coil device 1250. The forked ablation coil device 1250 comprises two ablation coils, a first ablation coil 1255 and a second ablation coil 1260. In accordance with several embodiments, the forked ablation coil device 1250 allows an entire vascular fork to be ablated simultaneously. In operation, the forked ablation coil device 1250 may be inserted to the target vasculature by overlapping the first ablation coil 1255 and the second ablation coil 1260 (effectively creating a single double helix coil). Once the target fork is reached, the first ablation coil 1255 and the second ablation coil 1260 may be separated and the first ablation coil 1255 inserted into a first branch of the target fork and the second ablation coil 1260 inserted into a second branch of the target fork. The branches of the target vessel fork (and the nerves within or surrounding the vessels of the fork branches) may then be simultaneously ablated.

In some embodiments, the coiled electrodes (e.g., ablation coil device 1200 or forked ablation coil device 1250) are created out of a memory material, such as nitinol or any other shape memory material. In some embodiments, energy may be delivered by the one or more coiled electrodes in a manner so as not to cause nerve ablation (temporary or permanent). In some embodiments, the thermal dose delivered may modulate nerves without causing ablation. The ablation coils may be delivered by one or more catheters. The ablation coils may be coupled to a catheter such that the ablation coils may be removed or repositioned following ablation of a target location. Balloon electrodes or other ablation elements may be used instead of ablation coils. In some embodiments, a single balloon with multiple electrodes may be used instead of the coiled electrodes. A portion of the balloon with an electrode may be positioned in each of the branches. In other embodiments, each of the branches may be occluded with an occlusion member and fluid may be infused to create a wet electrode effect for ablation.

In some embodiments, energy is delivered between two ablation elements positioned to span a vessel bifurcation in a bipolar manner, thereby concentrating delivery of energy and denervation between the ablation elements in a bifurcation region where a higher density of nerve fibers may exist.

Figure 13A:
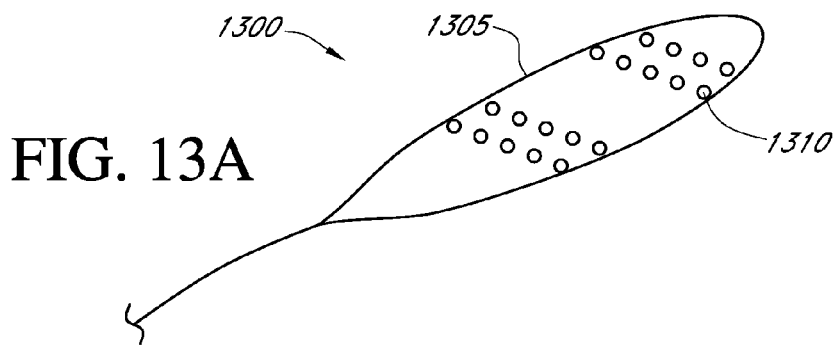
FIGS. 13A-13C, 14A and 14B illustrate embodiments of energy delivery catheters.
Figure 13B:
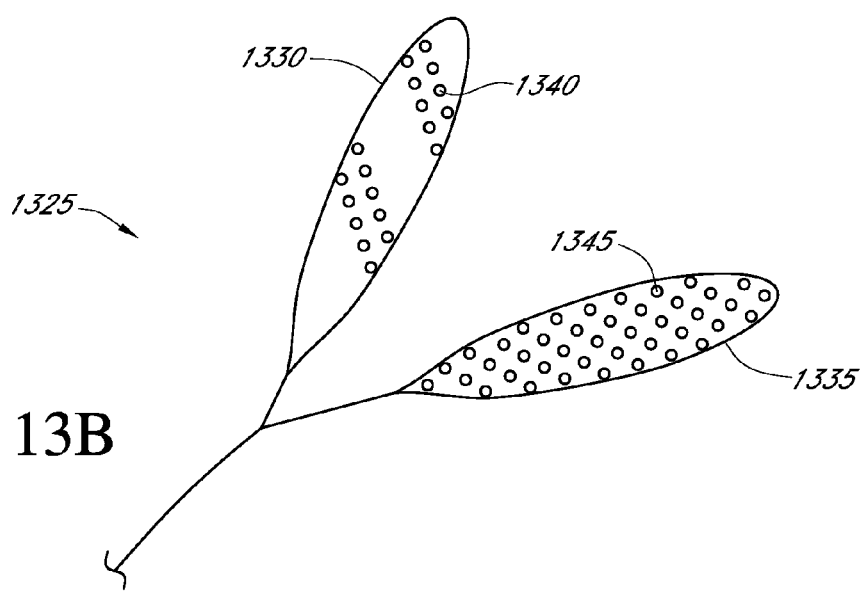
Figure 13C:
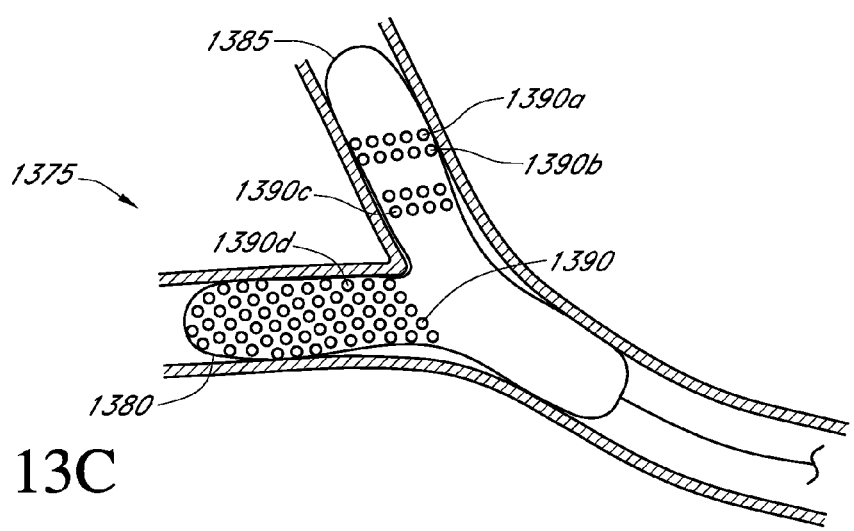

FIGS. 13A-13C illustrate embodiments of balloon ablation catheters. FIG. 13A illustrates an embodiment of a single balloon ablation catheter 1300, FIG. 13B illustrates an embodiment of a forked double balloon ablation catheter 1325, and FIG. 13C illustrates an embodiment of a forked balloon ablation catheter 1375.

The single balloon ablation catheter 1300 of FIG. 13A comprises an electrode balloon 1305 having at least one electrode 1310 (e.g., one electrode, two electrodes, three electrodes, four electrodes, five to ten electrodes, ten to twenty electrodes, or more than twenty electrodes). The electrode patterns and configurations shown in FIGS. 13A-13C illustrate various embodiments of electrode patterns and configurations; however, other patterns and configurations may be used as desired or required. In some embodiments, a high dielectric constant material may be used in the place of at least one electrode. The single balloon ablation catheter 1300 may be inserted into target vasculature and then inflated and used to ablate the vasculature (and thereby ablate the nerves within or surrounding the vessel). To ablate a vascular fork, it may be necessary to insert the single balloon ablation catheter 1300 into one branch of the fork and ablate that branch, then retract the single balloon ablation catheter 1300 from that branch and insert the single balloon ablation catheter 1300 into the other branch of the fork and ablate that branch.

The forked two balloon ablation catheter 1325 of FIG. 13B includes a first electrode balloon 1330 and a second electrode balloon 1335. The first electrode balloon 1330 includes at least a first electrode 1340, and the second electrode balloon 1330 includes at least a second electrode 1345. In several embodiments, the forked two balloon ablation catheter 1325 allows an entire vascular fork (e.g., all branches) to be ablated simultaneously. In operation, the forked two balloon ablation catheter 1325 is inserted into the vasculature and advanced to the target fork. Once the target fork is reached, the left electrode balloon 1330 and the right electrode balloon 1335 may be inflated and the left electrode balloon 1330 inserted into the left branch of the target fork and the right electrode balloon 1335 inserted into the right branch of the target fork (or vice versa). The target fork may then be simultaneously ablated. As discussed above, the first balloon and the second balloon can comprise a plurality of electrodes, or in some embodiments, at least one of the electrodes is replaced with a high dielectric constant material. The one or more electrodes may be individually connected to a pulse generator. By selectively and/or sequentially activating one or more electrode pair simultaneously, energy delivery to the surrounding tissue can be uniquely directed toward target anatomy with respect to balloon position. For example, referring now to FIG. 13C, energy could be directed between electrode 1390A and electrode 1390B in order to create a focused lesion within the vessel wall, or between electrode 1390C and 1390D to focus energy delivery at the vessel bifurcation.

The forked balloon ablation catheter 1375 of FIG. 13C includes a single balloon which has a left fork 1380 and a right fork 1385 with at least one balloon electrode 1390. In some embodiments the forked balloon ablation catheter 1375 comprises at least one balloon electrode for each balloon fork. The electrodes can be spaced and distributed along the balloon to facilitate positioning of at least one balloon electrode in each branch of the target fork. The forked balloon ablation catheter 1375 operates in the same manner as the forked double balloon ablation catheter 1325; however, it may advantageously allow for more effective ablation of the crotch of the vascular fork. In some embodiments, the balloon of the forked balloon ablation catheter 1375 is substantially the shape of the target fork or is configured to conform to the shape of the target fork. In some embodiments, the forked balloon ablation catheter 1375 is configured to be used in vessels having forks with three or more branches (such as the fork between the common hepatic artery, proper hepatic artery and the gastroduodenal artery). In some embodiments, each of the branches of the vessel fork may be occluded with an occlusion member and fluid may be infused to form a wet electrode for ablation.

An electrode balloon may be used to ablate (or otherwise modulate) target vasculature. In some embodiments, the electrode balloon is inserted via a catheter and inflated such that the balloon is in contact with substantially all of the fork intimal walls. In some embodiments, the electrode balloon is substantially oval. A two-step approach may be used to ablate the entire surface of the fork: first, the balloon can be put in place in one branch of the fork (e.g., the proper hepatic artery branch), inflated, and then used to ablate; second, the balloon can be retracted and then advanced into the other fork (e.g., the gastroduodenal artery branch), inflated, and then used to ablate. In some embodiments, the electrode balloon comprises ablation electrodes on an external surface in sufficient density that simultaneous ablation of the entire intimal wall in contact with the electrode balloon is possible. In some embodiments, the ablation electrodes on the surface of the electrode balloon are arranged in a predetermined pattern. In some embodiments, the ablation electrodes on the surface of the electrode balloon are activated simultaneously. In some embodiments, the ablation electrodes on the surface of the electrode balloon are individually addressable (e.g., actuatable), thereby allowing selective areas to be ablated as desired. In some embodiments, at least one electrode on the electrode balloon is an ablation electrode and at least one electrode on the electrode balloon is a sensing electrode (used for example to sense impedance, temperature, etc.).

In some embodiments, the electrode balloon comprises a proximal electrode and a distal electrode configured to be individually actuatable and configured to be used in a stimulation mode, ablation mode, and/or sensing mode. The proximal electrode and distal electrode may be positioned in two different branches (e.g., the proximal electrode in the proper hepatic artery and the distal electrode in the gastroduodenal artery). The electrode balloon may be deployed from a guide catheter positioned in the common hepatic artery. In one embodiment, the proximal electrode is stimulated and the distal electrode is sensed and if the correct territory is identified (e.g., nerve fibers emanating to the proper hepatic artery but not the gastroduodenal artery), then the proximal electrode may be activated for ablation. The electrode balloon may be used to map and selectively ablate various vessel portions.

In some embodiments, a round electrode balloon may be used to selectively ablate only a select area. In some embodiments, the round electrode balloon has approximately the same electrode properties as described above, including electrode density, and the presence of at least one ablation electrode. In some embodiments, the round electrode balloon comprises at least one sensor electrode.

In some embodiments, a dielectric ablating balloon is used. The dielectric ablating balloon may have the same shape characteristics as do the other electrode balloon embodiments described herein. In some embodiments, the dielectric ablating balloon comprises at least one piece of a high conductivity material on its outer surface. In some embodiments, use of the dielectric ablating balloon comprises advancing the dielectric ablating balloon into position in the target vessel through methods described herein and inflating the dielectric ablating balloon so that its outer surface is proximate to the intimal walls of the target vessel. In some embodiments, a microwave generator is then placed near the surface of the body of the subject and microwaves are directed from the microwave generator toward the dielectric ablating balloon within the subject such that the microwaves interact with the at least one piece of a high conductivity material to create heat and such that the heat created thermally ablates the region (e.g., vessel wall surface) proximate to the at least one high permittivity material. In some embodiments, the dielectric ablating balloon comprises a plurality of (e.g., two, three, four or more than four) pieces or portions of high conductivity material on its outer surface.

In some embodiments, lower power and longer timed ablations may be used for ablation procedures involving occlusion within the hepatic arteries than in other arteries. Such treatment may be uniquely possible because of the liver's dual source blood supply (as described above). Balloon ablation of the hepatic artery may employ full occlusion for a substantial period of time, not previously possible or not previously attempted in other locations for safety reasons (e.g., to avoid potential stroke due to ischemia). In some embodiments, balloons may be inflated and used for ablation in the range of about 1 to about 10 minutes, about 10 minutes to about 20 minutes, about 20 minutes to about 60 minutes, about 15 minutes to about 45 minutes, about 10 minutes to about 40 minutes, about 15 minutes to about 20 minutes, about 25 minutes, about 30 minutes, about 35 minutes, about 40 minutes, about 45 minutes, about 50 minutes, about 55 minutes, about 60 minutes. Longer ablation times may have several advantages in accordance with several embodiments. First, longer exposure times mean that lower treatment temperatures may be used because tissue and nerve death is a function of both temperature and time. In some embodiments, temperatures are used in the ranges of about 30° C. to about 80° C., about 40° C. to about 70° C., or about 50° C. to about 60° C. In one embodiment, temperatures greater than 45° C. and less than 60° C. are used.

In some embodiments, the arterial lumen may be simultaneously protected by infusing a low temperature coolant through the balloon cavity (thereby keeping the intima cool) while focusing RF energy and thermal heating at the level of the adventitia (where the target nerves are located). Second, balloon occlusion may facilitate improved contact and contact pressure between the electrodes disposed on the outside of the balloon and the arterial wall. Third, balloon occlusion may compress the tissues of the arterial wall and thereby reduce the distance from the electrode(s) to the target nerves, which improves the efficiency of thermal energy delivery to the target nerves. Fourth, less contrast/imaging agent may be required by using a balloon catheter because an occluding device is reliably and accurately positioned (and maintains that position once in place), and serves as a reliable marker of device and therapy placement. Additionally, when a balloon engages the vascular wall, heating of the blood is avoided entirely (because energy is transferred directly from the electrode(s) to the vessel wall without directly contacting the blood), thereby reducing the risk of vapor bubble formation or thrombosis (e.g., clot formation).

Balloon ablation catheter systems may be advantageous for denervating nerves surrounding the hepatic artery branches may be advantageous in that the hepatic artery can be occluded by one or more balloons and then coolant can be circulated in the region of the ablation (e.g., through a lumen of a balloon). In various embodiments, balloon ablation catheters advantageously facilitate both higher power net energy through larger electrode surface area (enabled, for example, by large electrode sizes that can be included on a balloon) and increased deposition time (which may be permitted by the ability to occlude flow to the hepatic artery for longer periods of time). In some embodiments, the risk of damage to the endothelial wall is mitigated by the flow of coolant even with an increase in energy density through higher power. Accordingly, higher power energy delivery (e.g., about 40 to 50% higher power) may be used than denervation systems used for denervation of other vessels or organs without risk of damage to the endothelial region of the hepatic artery due to maintained less than hyperthermic temperatures up to 1 mm from the lumen of the hepatic artery.

In some embodiments, an actively-cooled balloon catheter is used to ablate target vasculature. A pump sufficient to deliver high flow coolant to the cooling element may be used to facilitate the active cooling. In several embodiments, the range of drive pressures to deliver an appropriate flow rate (e.g., between about 100 and 500 mL/min) of coolant into a 4 to 6 Fr balloon catheter to maintain an appropriate temperature is between about 25 and about 150 psi. The flow rate may be adjusted on the basis of the actual temperature inside the balloon. In some embodiments, the desired coolant temperature in the balloon is between about 5° C. and about 10° C. In some embodiments, thermocouples are included inside the balloon to constantly monitor the coolant temperature. The pump output may be increased or decreased based on the difference between the desired temperature and the actual temperature of the coolant.

Figure 14A:
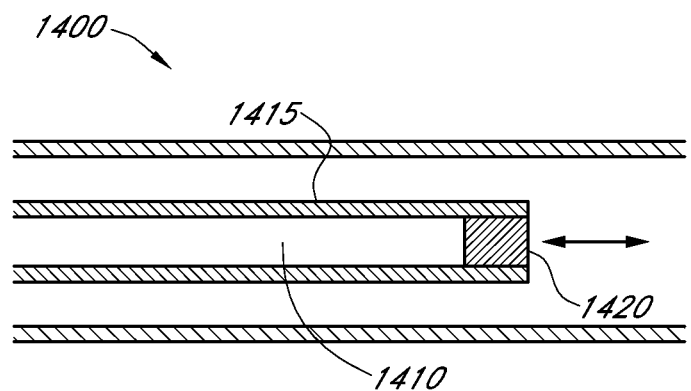
Figure 14B:
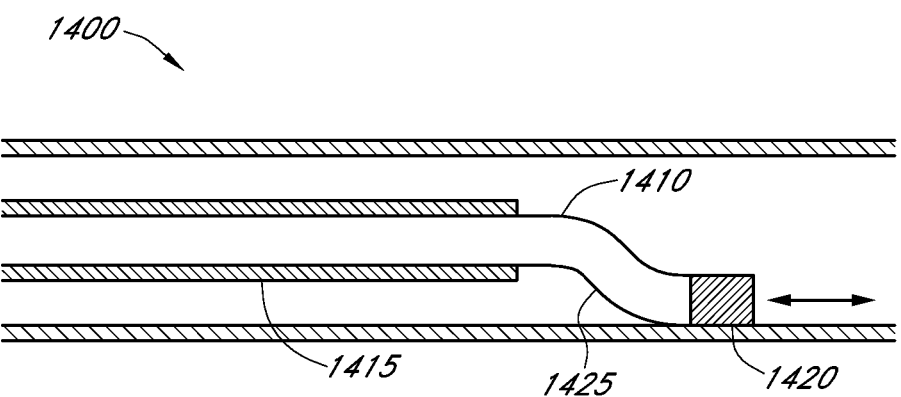

The hepatic artery anatomy is generally more tortuous and variable than anatomies of other vessels in other areas. Maintaining good contact of electrodes or other energy delivery elements in the tortuous hepatic artery anatomy can be difficult and may require the use of different catheter devices than existing catheter devices for nerve ablation. FIGS. 14A and 14B illustrate an embodiment of a low-profile ablation catheter 1400 that may advantageously facilitate contact of electrodes or other energy delivery elements with the inner walls of arteries of the tortuous hepatic vascular anatomy. The low-profile ablation catheter 1400 comprises an inner electrode member 1410 and an outer sheath 1415. The inner electrode member 1410 may comprise a reversibly deflectable, pre-shaped cylindrical shaft comprising resilient (e.g., shape memory) material and at least one electrode 1420. In one embodiment, the outer sheath 1415 comprises a guide catheter having a lumen. The inner electrode member 1410 may be configured to be delivered within the lumen of the outer sheath 1415 and to be translatable relative to the outer sheath 1415 such that the inner electrode member 1410 may be advanced out of a distal end of the outer sheath 1415 and retracted back in. In one embodiment, the inner electrode member 1410 assumes a generally deflected (e.g., off-axis) configuration when advanced out of the distal end of the outer sheath 1415, as shown in FIG. 14B. In this unconstrained state, the distal end of the inner electrode member 1410 deviates from a longitudinal axis defined by the proximal portion of the electrode. When the inner electrode member 1410 is retracted within the outer sheath 1415, the inner electrode member 1410 is resiliently deformed to assume a substantially straight shape defined by the substantially straight shape of the lumen of the outer sheath 1415, as shown in FIG. 14A. In some embodiments, when the inner electrode member 1410 is advanced out of the distal end of the outer sheath 1415, the distal end portion of the inner electrode member 1410 deflects to contact a vessel wall (e.g., arterial wall). The shape of the distal end of the inner electrode member 1410 in the unconstrained state may be pre-formed to ensure contact with the vessel wall.

In some embodiments, the outer sheath 1415 has a diameter of less than about 4 mm, less than about 3 mm, less than about 2 mm, or less than about 1 mm. In some embodiments, the inner electrode member 1410 comprises a shaft formed, at least partly, of memory material such as a nickel titanium alloy material. The inner electrode member 1410 may have an outer cross-sectional dimension that is substantially equal to the outside diameter of the outer sheath 1415 or may have an outer cross-sectional dimension that is smaller or larger than the outside diameter of the outer sheath 1415. In some embodiments, when the inner electrode member 1410 is slid out of the outer sheath 1415 past a pre-formed step 1425 at or near its distal end, the step 1425 at or near the distal end places the surface of the distal end of the inner electrode member 1410 away from the natural axis of the outer sheath 1415. In some embodiments, the step 1425 near the distal end of the inner electrode member 1410 places the surface of the inner electrode member 1410 between about the same plane as the outer surface of the outer sheath 1415 and about double the diameter from the center of the outer sheath 1415 to the outer surface of the outer sheath 1415.

In some embodiments, the magnitude of the off-axis deflection created in the step 1425 near the distal end is tailored to satisfy varying anatomic requirements (e.g., larger step near the distal end for larger blood vessels and smaller step near the distal end for smaller blood vessels). In some embodiments, the inner electrode member 1410 is interchangeable and may be replaced with a different inner electrode member with different size parameters. The different sizes of inner electrode members or electrode members with different pre-formed shapes may be provided in a kit and an appropriate inner electrode member may be selected after evaluating patient anatomy (for example, by CT, fluoroscopy, or ultrasound imaging methods). In some embodiments, the inner electrode member 1410 is rotated within the catheter body In some embodiments, the at least one electrode 1420 of the inner electrode member 1410 comprises one or more monopolar, bipolar or multipolar electrodes (the addition of additional pre-shaped electrodes may enable bipolar and multi-polar RF energy delivery). Any combination of electrodes may be incorporated into the design of the inner electrode member 1410 to create a catheter with any desired properties.

In some embodiments, the shaft of the inner electrode member 1410 comprises an insulation member to prevent heat transfer away from or electrically insulate portions of the inner electrode member 1410. In some embodiments, the insulation member is a tubing, coating or heat shrink comprised of polyamide, polytetrafluoroethylene, polyetheretherketone, polyethylene, or any other high dielectric material. The insulation member may comprise one or more openings to expose portions of the distal end portion of the inner electrode member 1410. In some embodiments, the insulation member is used to define specific electrode geometries by selective removal of the insulation member in whatever geometry is desired. In other embodiments, the inner electrode member 1410 comprises a shape memory polymer or shape-biased polymer with one or more electrode leads disposed therein. In one embodiment, the low-profile ablation catheter comprises a catheter coextruded with a shape memory electrode spine, where the extruded catheter provides electrical insulation. In one embodiment, the at least one electrode 1420 comprises a spherical electrode. In one embodiment, the distal end of the inner electrode shaft comprises a series of electrodes.

In some embodiments, the low-profile ablation catheter 1400 comprises a radial window or slot in a side portion near the distal end of the ablation catheter. In one embodiment, the distal end of the inner electrode member 1410 is configured to be deployed out of the radial window or slot. In one embodiment, the lumen of the ablation catheter 1400 comprises a ramp leading up to the radial window or slot to direct the distal end of the inner electrode member out of the radial window or slot.

In accordance with several embodiments, the low-profile ablation catheter 1400 advantageously provides a device that comprises a low profile (e.g., small outer cross-sectional dimension) and uses the same mechanism to actuate the electrode deflection as well as the electrode itself, thereby reducing the number of distinct components. The inner electrode 1410 of the low-profile ablation catheter may also advantageously be at least partially deployed to facilitate navigation by providing a variety of tip curvature options for "hooking" vascular branches or navigating tortuous vessels during catheter insertion. In accordance with several embodiments, the low-profile ablation catheter 1400 advantageously facilitates solid and continuous contact with the vessel wall, thereby allowing for substantially constant voltage to maintain a desired electrode tip temperature.

Figure 15:
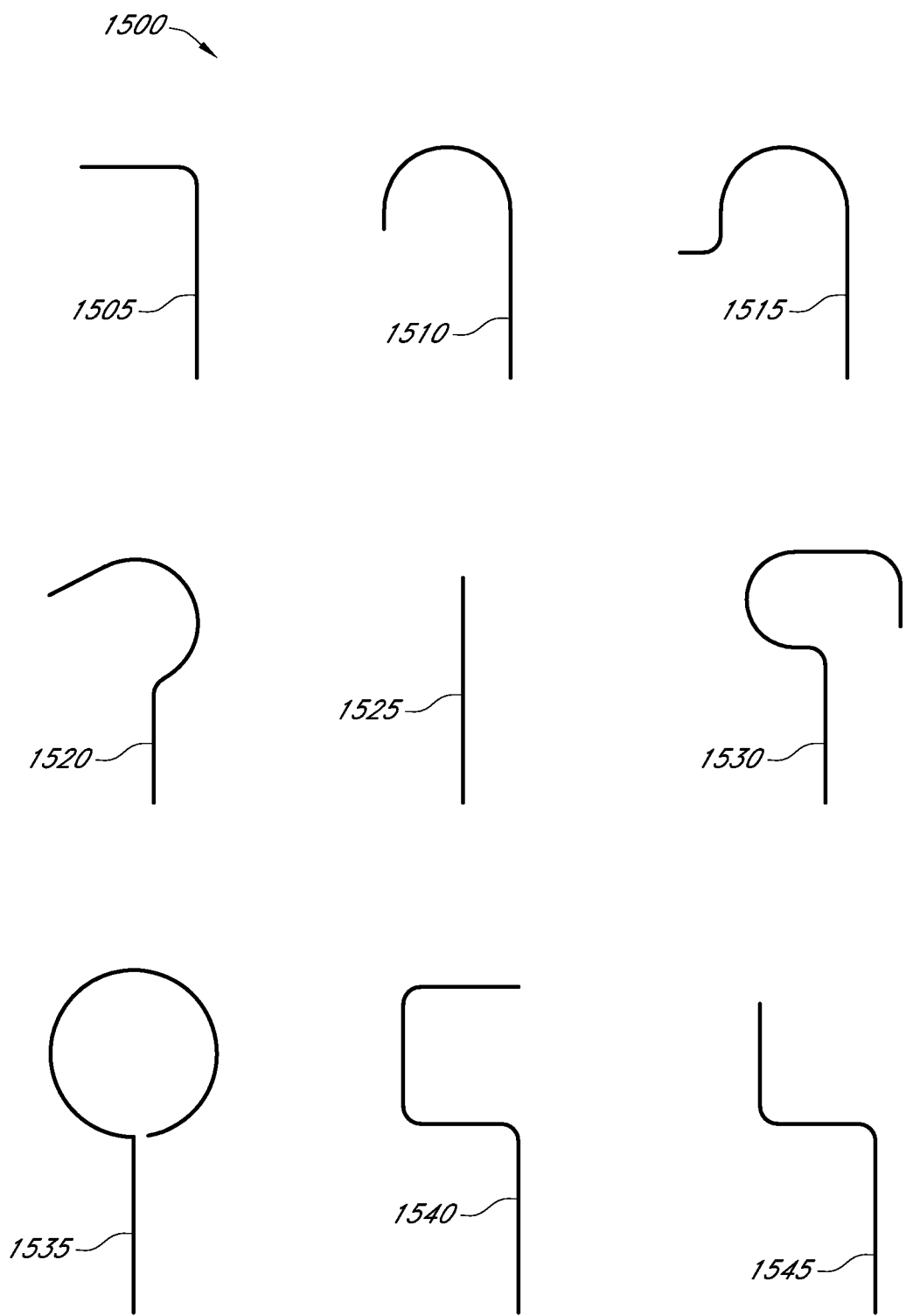
FIG. 15 illustrates several embodiments of catheter distal tip electrode and guide wire shapes.

FIG. 15 illustrates various embodiments of distal tip electrode and guide wire shapes 1500. The distal tip electrode and guide wire shapes 1500 may include an "L" shaped tip 1505, a "J" shaped tip 1510, a "shepherds crook"-shaped tip 1515, a "hook" shaped tip 1520, a "line" shaped tip 1525, a "key" shaped tip 1530, a "circle" shaped tip 1535, a "square hook" shaped tip 1540, or a "step" shaped hook 1545. A spiral-shaped tip (such as shown in FIG. 12A) may also be used. In one embodiment, a lasso-shaped tip is used. The lasso-shaped tip may have a similar configuration to the "circle" shaped tip 1535 but with the "circle"- or "lasso"-shaped tip portion being oriented substantially perpendicular to the straight line portion. The various shapes illustrated in FIG. 15 may advantageously be selected from and used in conjunction with the low-profile ablation catheter 1400 or other catheter devices to facilitate contact of electrodes or other energy delivery elements with the inner walls of arteries of the tortuous hepatic vascular anatomy (e.g., based on the particular vascular anatomy of the subject being treated or the particular vessels being treated). Any of the shapes 1500 shown in FIG. 15 may comprise a plurality of electrodes arranged in different patterns.

In some embodiments, the distal tip electrode itself, or a guide wire, may be partially or fully extended from an insertion catheter, to aid in navigation, thereby providing for a variety of tip curvature options for "hooking" vascular branches during catheter insertion. In some embodiments, shape-memory electrodes may be interchangeable by a clinician-user. For example, the clinician may select the most appropriate shape conformation for the patient's unique anatomy from a kit of different shaped devices, rather than being bound to a single device conformation or configuration. The various shaped tips may advantageously be selected to optimize the ability for the one or more electrodes or energy delivery elements to contact the target vessel due to the tortuosity and variability of the vascular anatomy at and/or surrounding the target vessel. The electrode assembly may also include a sensing element, such as a thermal sensing element (thermistor or thermocouple) to permit measurement of tissue temperatures and energy delivery during the treatment. The sensing element may provide feedback regarding confirmation of denervation or blocking of nerve conduction.

In accordance with several embodiments, once a particular shape is selected, forces (F) can be applied to the proximal end of the electrode to adjust the contact force F' against a vessel wall. In some embodiments, the degree of strain of the electrode distal portion is proportional to the force applied to the vessel wall. Radiopaque markers may be placed along the length of the inner electrode 1410 and the relative angle Φ between lines drawn between two of the radiopaque markers can be designed such that F'=f(Φ(F)). A clinician may then adjust the force on the proximal end of the electrode to achieve the desired contact force.

In some embodiments, a catheter having an outer diameter substantially matching the target vessel's inner diameter is used, thereby minimizing mechanical and footprint requirements for precise targeting. A catheter may be selected from a kit of catheters having various outside diameter dimensions based on a measured inner diameter of the target vessel. In some embodiments, the outside diameter of a catheter can be modified using spacers provided in a procedure kit. The catheter may be advanced through the patient's vasculature (the inner diameter of which may decrease as the target location nears). Once the catheter is advanced to the target vessel location, it may then advantageously engage the vessel wall with substantially uniform contact pressure about its circumference. In some embodiments, because application of energy to the entire circumference of the vessel is undesirable (due to the risk of stenosis,) any of the designs herein disclosed that employ selective electrode placement or electrode "windows" are used, thereby allowing the delivery of energy in discrete locations about the vessel wall.

Figure 16A:
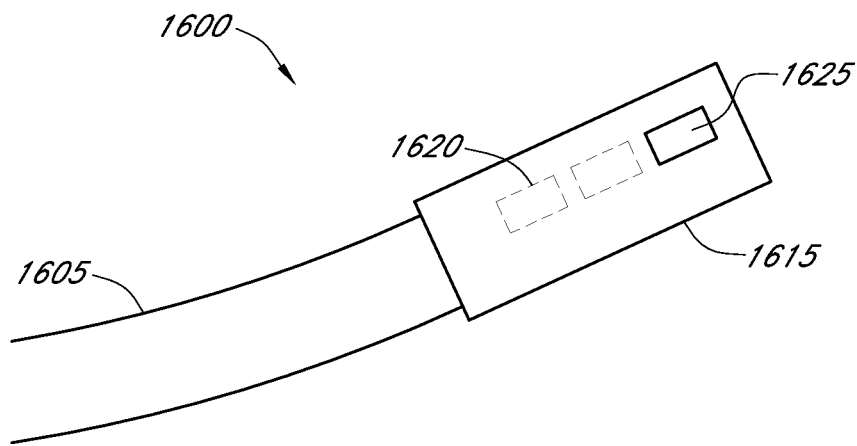
FIGS. 16A and 16B illustrate an embodiment of a windowed ablation catheter.
Figure 16B:
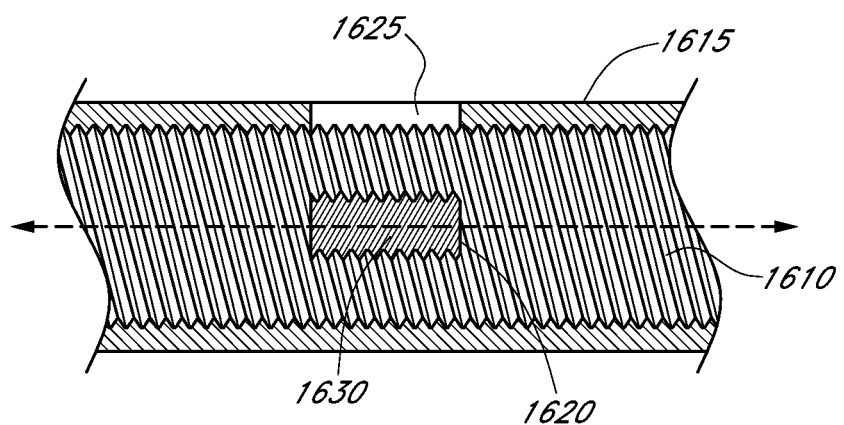

FIGS. 16A and 16B illustrate an embodiment of a windowed ablation catheter 1600. The windowed ablation catheter 1600 comprises a catheter body 1605, an inner sleeve 1610 having a first window 1620 and at least one ablation electrode 1630 and an outer sleeve 1615 having a second window 1625. FIG. 16A shows a view of the distal end of the windowed ablation catheter 1600 and FIG. 16B shows a detailed cut-away view of the distal end of the windowed ablation catheter 1600.

In some embodiments, the ablation electrode 1630 is disposed within a lumen of the inner sleeve 1610. The inner sleeve 1610 is rotatably received within the outer sleeve 1615 such that the outer sleeve 1615 is rotatable about the inner sleeve 1610. Energy can be delivered by the catheter by aligning the second window 1625 of the outer sleeve 1615 with the first window 1620 of the inner sleeve 1610 by rotating the inner sleeve 1610 with respect to the outer sleeve 1615, or vice-versa. In one embodiment, the inner sleeve 1610 comprises a dielectric covering to provide insulation.

In some embodiments, when the first window 1620 of the inner sleeve 1610 and the second window 1625 of the outer sleeve 1615 overlap, the ablating electrode 1630 is exposed to the outside of the outer sleeve 1615 (which may be placed against the wall of the target vessel). In one embodiment, energy only reaches the wall of the target vessel when the first window 1620 and the second window 1625 overlap, or are at least partially aligned. The degree of overlap may be controlled by the rotation or translation of the inner sleeve 1610 relative to the outer sleeve 1615. In one embodiment, the catheter is inserted by a user, the inner sleeve 1610 is turned based on user control, and the outer sleeve 1615 is turned based on user control, thereby allowing selective application of energy generated by the at least one ablation electrode to substantially any portion of the target vessel.

In some embodiments, the inner sleeve 1610 comprises multiple openings spaced along the length of the inner sleeve 1610 at different locations. For example, the inner sleeve 1610 may have openings spaced linearly along the axis of the inner sleeve 1610 and openings rotated about the axis of the inner sleeve 1610. In one embodiment, the openings of the inner sleeve 1610 define a spiral pattern. As shown in FIG. 16B, the external surface of the inner sleeve 1610 and the internal surface of the outer sleeve 1615 may be threaded such that the inner sleeve 1610 is translated with respect to the outer sleeve 1615 by rotation of the outer sleeve 1615 relative to the inner sleeve 1610. In some embodiments, relative rotation of the outer sleeve 1615 with respect to the inner sleeve 1610 serves to both translate and rotate window 1625 of the outer sleeve 1615, sequentially exposing vascular tissue to the ablation electrode 1635 through each of the openings of the inner sleeve 1610. In accordance with several embodiments, a windowed ablation catheter as described herein may facilitate creation of a spiral lesion along a length of the vessel wall. By selectively creating openings in the inner sleeve 1610, and rotating the outer sleeve 1615 with respect to the inner sleeve 1610, substantially any pattern of ablation along a helical path may be created.

To improve ablation catheter-vascular wall contact and thereby improve treatment efficacy, some embodiments include a window on the distal tip of the ablation catheter, or incorporated into one or more of the electrode windows, to provide suction (or vacuum pressure). The suction provided to the lumen wall places the artery in direct contact with the device to thereby achieve more efficient and less damaging ablation.

Figure 17:
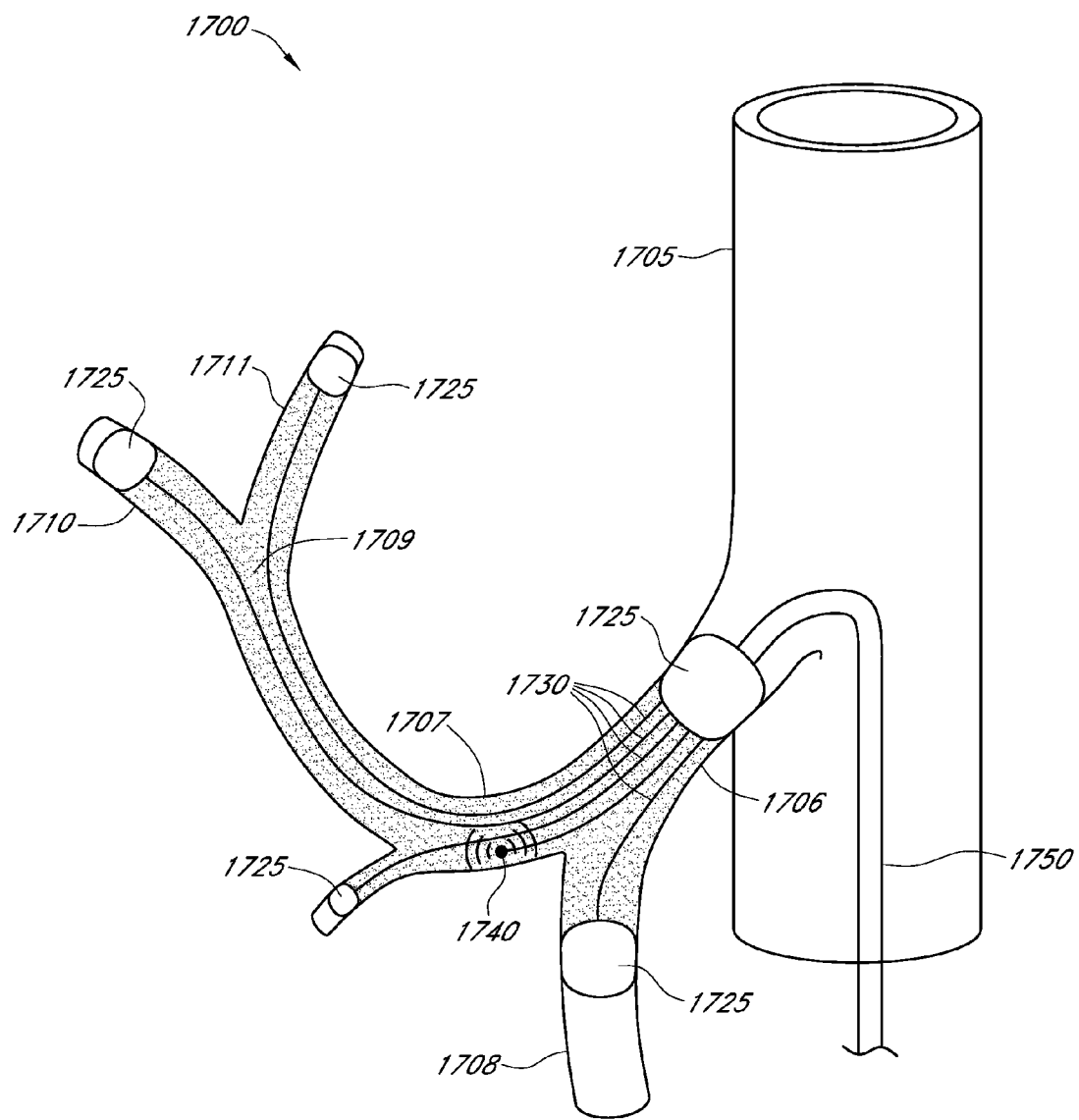
FIG. 17 illustrates an embodiment of a balloon-based volume ablation catheter system.

FIG. 17 is an embodiment of a balloon-based volume ablation system 1700, which can be used, for example, in the celiac, common hepatic, and proper hepatic arteries. In the illustrated embodiment, the balloon-based volume ablation system 1700 comprises a plurality of occlusive balloons 1725, a plurality of balloon guide wires 1730, a catheter 1750, and an electrode 1740. FIG. 17 also illustrates the abdominal aorta 1705, the celiac artery 1706, the common hepatic artery 1707, the splenic artery 1708, the proper hepatic artery 1709, the right hepatic artery 1710, and the left hepatic artery 1711 as an example of a target treatment site. In operation, the balloon-based volume ablation system 1700 may be inserted to the target treatment site through the abdominal aorta 1705 and into the celiac artery 1706. Individual occlusive balloons 1725 may then be advanced into subsequent vessels, such as the splenic artery 1708, the right hepatic artery 1710 and the left hepatic artery 1711. When the appropriate occlusive balloons 1725 have been placed such that they define the desired volume of vasculature to be ablated, the occlusive balloons 1725 may be inflated, thereby occluding the vessels in which they have been placed. In one embodiment, the target volume is then filled with saline and the electrode 1740 is activated to deliver electrical energy to heat the entire target volume simultaneously. The electrode 1740 may be configured to deliver sufficient energy to the target volume to ablate all or at least a portion of the nerves of the vessels within the target treatment site. Upon completion, the occlusive balloons 1725 may be deflated and the entire balloon-based volume ablation system 1700 may be retracted.

In some embodiments, it may be advantageous to simultaneously ablate a region of nerves innervating a portion of all, or a subset of all, arteries arising from the celiac artery (such as the left gastric artery, the splenic artery, the right gastric artery, the gastroduodenal artery, and the hepatic artery). In some embodiments, ablation is achieved by using balloon catheters or other occlusion members deployed from a guide catheter within the celiac artery or abdominal aorta to block off or occlude portions of vessels not to be ablated (the target volume may be adjusted by inflating balloons or placing occlusion members upstream and downstream of the desired volume, thereby creating a discrete volume), filling the target volume with saline solution through a guide catheter, and applying RF or other energy to the saline to thereby ablate the tissues surrounding the target volume in a manner that maintains vessel patency with hydraulic pressure while also providing for direct cooling of the endothelial surfaces of the vessels through circulation of chilled saline. In some embodiments, the described "saline electrode" system is used to pressurize the target arteries with saline. The contact pressure of the saline electrode against the arterial walls can be assessed by measurement of the arterial diameter on angiography and utilizing the pre-defined relationship between arterial diameter and fluid pressure or by using one or more pressure sensors, which in one embodiment, are included as a component of the saline electrode system. The saline electrode system may advantageously facilitate omnidirectional delivery of energy.

In some embodiments, hypertonic (e.g., hyperosmolar) saline is used in the ablation of the target volume. Using hypertonic saline may cause "loading" of the endothelial cells with ions, effectively increasing their conductivity. The loading of the endothelial cells with ions may have one or more of the following effects: decreasing ion friction in the endothelial lining (and other cells affected along the osmosis gradient, such as those in the media); reducing the heat deposited in the endothelial cell locations; preventing significant thermal damage to the endothelial cells; and increasing current density as a result of the increased conductivity in the region near the electrode, which may advantageously increase the efficiency of heating deeper in the vessel wall where the target nerves may be located.

In various embodiments, capacitive coupling or resistive heating catheter devices are used to deliver thermal energy. In one embodiment, a capacitive coupling catheter device comprises a balloon comprising a bipolar electrode pair arranged in a capacitive coupling configuration with an insulation layer between the two electrodes. In one embodiment, the insulation layer coats the two electrodes. In one embodiment, the balloon comprises a non-conductive balloon filled with saline that is capacitively coupled to the target tissue through the dielectric layer formed by the substantially non-conductive balloon membrane. The capacitive coupling catheter device may advantageously not require direct electrode contact with the target tissue, thereby reducing current density levels and edge effects required by other devices. Capacitive coupling devices or methods similar to those described in U.S. Pat. No. 5,295,038, incorporated herein by reference, may be used. A return electrode path may also be provided.

In one embodiment, a resistive heating energy delivery catheter comprises a balloon catheter having a resistive heating element disposed thereon. For example, the balloon catheter may comprise spiral resistive heater that wraps around the balloon. Instead of inducing RF currents in the vascular tissue, DC or AC/RF currents can be used to generate heat in the balloon catheter itself and the heat can be transmitted to the surrounding vascular tissue (e.g., hepatic arterial tissue) by conduction.

In some embodiments, an RF energy delivery system delivers RF energy waves of varying duration. In some embodiments, the RF energy delivery system varies the amplitude of the RF energy. In other embodiments, the RF energy delivery system delivers a plurality of RF wave pulses. For example, the RF energy delivery system may deliver a sequence of RF pulses. In some embodiments, the RF energy delivery system varies the frequency of RF energy. In other embodiments, the RF energy delivery system varies any one or more parameters of the RF energy, including, but not limited to, duration, amplitude, frequency, and total number of pulses or pulse widths. For example, the RF energy delivery system can deliver RF energy selected to most effectively modulate (e.g., ablate or otherwise disrupt) sympathetic nerve fibers in the hepatic plexus. In some embodiments, the frequency of the RF energy is maintained at a constant or substantially constant level.

In some embodiments, the frequency of the RF energy is between about 50 kHz and about 20 MHz, between about 100 kHz and about 2.5 MHz, between about 400 kHz and about 1 MHz, between about 50 kHz and about 5 MHz, between about 100 kHz and about 10 MHz, between about 500 kHz and about 15 MHz, less than 50 kHz, greater than 20 MHz, between about 3 kHz and about 300 GHz, or overlapping ranges thereof. Non-RF frequencies may also be used. For example, the frequency can range from about 100 Hz to about 3 kHz. In some embodiments, the amplitude of the voltage applied is between about 1 volt and 1000 volts, between about 5 volts and about 500 volts, between about 10 volts and about 200 volts, between about 20 volts and about 100 volts, between about 1 volt and about 10 volts, between about 5 volts and about 20 volts, between about 1 volt and about 50 volts, between about 15 volts and 25 volts, between about 20 volts and about 75 volts, between about 50 volts and about 100 volts, between about 100 volts and about 500 volts, between about 200 volts and about 750 volts, between about 500 volts and about 1000 volts, less than 1 volt, greater than 1000 volts, or overlapping ranges thereof.

In some embodiments, the current of the RF energy ranges from about 0.5 mA to about 500 mA, from about 1 mA to about 100 mA, from about 10 mA to about 50 mA, from about 50 mA to about 150 mA, from about 100 mA to about 300 mA, from about 250 mA to about 400 mA, from about 300 to about 500 mA, or overlapping ranges thereof. The current density of the applied RF energy can have a current density between about 0.01 mA/cm$^2$ and about 100 mA/cm$^2$, between about 0.1 mA/cm$^2$ and about 50 mA/cm$^2$, between about 0.2 mA/cm$^2$ and about 10 mA/cm$^2$, between about 0.3 mA/cm$^2$ and about 5 mA/cm$^2$, less than about 0.01 mA/cm$^2$, greater than about 100 mA/cm$^2$, or overlapping ranges thereof. In some embodiments, the power output of the RF generator ranges between about 0.1 mW and about 100 W, between about 1 mW and 100 mW, between about 1 W and 10 W, between about 10 W and 50 W, between about 25 W and about 75 W, between about 50 W and about 90 W, between about 75 W and about 100 W, or overlapping ranges thereof. In some embodiments, the total RF energy dose delivered at the target location (e.g., at an inner vessel wall, to the media of the vessel, to the adventitia of the vessel, or to the target nerves within or adhered to the vessel wall) is between about 100 J and about 2000 J, between about 150 J and about 500 J, between about 300 J and about 800 J, between about 500 J and about 1000 J, between about 800 J and about 1200 J, between about 1000 J and about 1500 J, and overlapping ranges thereof. In some embodiments, the impedance ranges from about 10 ohms to about 600 ohms, from about 100 ohms to about 300 ohms, from about 50 ohms to about 200 ohms, from about 200 ohms to about 500 ohms, from about 300 ohms to about 600 ohms, and overlapping ranges thereof.

The RF energy can be pulsed or continuous. The voltage, current density, frequencies, treatment duration, power, and/or other treatment parameters can vary depending on whether continuous or pulsed signals are used. For example, the voltage or current amplitudes may be significantly increased for pulsed RF energy. The duty cycle for the pulsed signals can range from about 0.0001% to about 100%, from about 0.001% to about 100%, from about 0.01% to about 100%, from about 0.1% to about 100%, from about 1% to about 10%, from about 5% to about 15%, from about 10% to about 50%, from about 20% to about 60% from about 25% to about 75%, from about 50% to about 80%, from about 75% to about 100%, or overlapping ranges thereof. The pulse durations or widths of the pulses can vary. For example, in some embodiments, the pulse durations can range from about 10 microseconds to about 1 millisecond; however, pulse durations less than 10 microseconds or greater than 1 millisecond can be used as desired and/or required. In accordance with some embodiments, the use of pulsed energy may facilitate reduced temperatures, reduced treatment times, reduced cooling requirements, and/or increased power levels without risk of increasing temperature or causing endothelial damage due to heating.

The treatment time durations can range from 1 second to 1 hour, from 5 seconds to 30 minutes, from 10 seconds to 10 minutes, from 30 seconds to 30 minutes, from 1 minute to 20 minutes, from 1 minute to 3 minutes, from 2 to four minutes, from 5 minutes to 10 minutes, from 10 minutes to 40 minutes, from 30 seconds to 90 seconds, from 5 seconds to 50 seconds, from 60 seconds to 120 seconds, overlapping ranges thereof, less than 1 second, greater than 1 hour, about 120 seconds, or overlapping ranges thereof. The duration may vary depending on various treatment parameters (e.g., amplitude, current density, proximity, continuous or pulsed, type of nerve, size of nerve). In some embodiments, the RF or other electrical energy is controlled such that delivery of the energy heats the target nerves or surrounding tissue in the range of about 50 to about 90 degrees Celsius (e.g., 60 to 75 degrees, 50 to 80 degrees, 70 to 90 degrees, or overlapping ranges thereof). In some embodiments, the temperature can be less than 50 or greater than 90 degrees Celsius. The electrode tip energy may range from 37 to 100 degrees Celsius. In some embodiments, RF ablation thermal lesion sizes range from about 0 to about 3 cm (e.g., between 1 and 5 mm, between 2 and 4 mm, between 5 and 10 mm, between 15 and 20 mm, between 20 and 30 mm, overlapping ranges thereof, about 2 mm, about 3 mm) or within one to ten (e.g., one to three, two to four, three to five, four to eight, five to ten) media thickness differences from a vessel lumen (for example, research has shown that nerves surrounding the common hepatic artery and other braches of the hepatic artery are generally within this range). In several embodiments, the media thickness of the vessel (e.g., hepatic artery) ranges from about 0.1 cm to about 0.25 cm. In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements.

In some embodiments, an RF ablation catheter is used to perform RF ablation of sympathetic nerve fibers in the hepatic plexus at one or more locations. For example, the RF ablation catheter may perform ablation in a circumferential or radial pattern to ablate sympathetic nerve fibers in the hepatic plexus at one or more locations (e.g., one, two, three, four, five, six, seven, eight, nine, ten, six to eight, four to eight, more than ten locations). In other embodiments, the sympathetic nerve fibers in the hepatic plexus are ablated at one or more points by performing RF ablation at a plurality of points that are linearly spaced along a vessel length. For example, RF ablation may be performed at one or more points linearly spaced along a length of the proper hepatic artery to ablate sympathetic nerve fibers in the hepatic plexus. In some embodiments, RF ablation is performed at one or more locations in any pattern to cause ablation of sympathetic nerve fibers in the hepatic plexus as desired and/or required (e.g., a spiral pattern or a series of linear patterns that may or may not intersect). The ablation patterns can comprise continuous patterns or intermittent patterns. In accordance with various embodiments, the RF ablation does not cause any lasting damage to the vascular wall because heat at the wall is dissipated by flowing blood, by cooling provided external to the body, or by increased cooling provided by adjacent organs and tissue structures (e.g., portal vein cooling and/or infusion), thereby creating a gradient with increasing temperature across the intimal and medial layers to the adventitia where the nerves travel. The adventitia is the external layer of the arterial wall, with the media being the middle layer and the intima being the inner layer. The intima comprises a layer of endothelial cells supported by a layer of connective tissue. The media is the thickest of the three vessel layers and comprises smooth muscle and elastic tissue. The adventitia comprises fibrous connective tissue.

In some embodiments, the energy output from the RF energy source may be modulated using constant temperature mode. Constant temperature mode turns the energy source on when a lower temperature threshold is reached and turns the energy source off when an upper temperature threshold is reached (similar to a thermostat). In some embodiments, an ablation catheter system using constant temperature mode requires feedback, which, in one embodiment, is provided by a temperature sensor. In some embodiments, the ablation catheter system comprises a temperature sensor that communicates with energy source (e.g., RF generator). In some of these embodiments, the energy source begins to deliver energy (e.g., turn on) when the temperature sensor registers that the temperature has dropped below a certain lower threshold level, and the energy source terminates energy delivery (e.g., turns off) when the temperature sensor registers that the temperature has exceeded a predetermined upper threshold level.

In some embodiments, the energy output from an energy delivery system may be modulated using a parameter other than temperature, such as tissue impedance. Tissue impedance may increase as tissue temperature increases. Impedance mode may be configured to turn the energy source on when a lower impedance threshold is reached and turn the energy source off when an upper impedance threshold is reached (in the same fashion as the constant temperature mode responds to increases and decreases in temperature). An energy delivery system using constant impedance mode may include some form of feedback mechanism, which, in one embodiment, is provided by an impedance sensor. In some embodiments, impedance is calculated by measuring voltage and current and dividing voltage by the current.

In some embodiments, a catheter-based energy delivery system comprises a first catheter with a first electrode and a second catheter with a second electrode. The first catheter is inserted within a target vessel (e.g., the common hepatic artery) and used to deliver energy to modulate nerves within the target vessel. The second catheter may be inserted within an adjacent vessel and the impedance can be measured between the two electrodes. For example, if the first catheter is inserted within the hepatic arteries, the second catheter can be inserted within the bile duct or the portal vein. In some embodiments, a second electrode is placed on the skin of the subject and the impedance is measured between the second electrode and an electrode of the catheter-based energy delivery system. In some embodiments, the second electrode may be positioned in other locations that are configured to provide a substantially accurate measurement of the impedance of the target tissues.

In some embodiments, the impedance measurement is communicated to the energy source (e.g., pulse generator). In some embodiments, the energy source begins to generate a pulse (i.e., turns on) when the impedance registers that the impedance has dropped below a certain lower threshold level, and the energy source terminates the pulse (i.e., turns off) when the impedance registers that the impedance has exceeded a predetermined upper threshold level.

In some embodiments, the energy output of the energy delivery system is modulated by time. In such embodiments, the energy source of the energy delivery system delivers energy for a predetermined amount of time and then terminates energy delivery for a predetermined amount of time. The cycle may repeat for a desired overall duration of treatment. In some embodiments, the predetermined amount of time for which energy is delivered and the predetermined amount of time for which energy delivery is terminated are empirically optimized lengths of time. In accordance with several embodiments, controlling energy delivery according to impedance and reducing energy delivery when impedance approaches a threshold level (or alternatively, modulating energy in time irrespective of impedance levels) advantageously provides for thermal energy to be focused at locations peripheral to the vessel lumen. For example, when the energy pulse is terminated, the vessel lumen may cool rapidly due to convective heat loss to blood, thereby protecting the endothelial cells from thermal damage. In some embodiments, the heat in the peripheral tissues (e.g., where the targeted nerves are located) dissipates more slowly via thermal conduction. In some embodiments, successive pulses tend to cause preferential heating of the peripheral (e.g., nerve) tissue. In accordance with several embodiments, when the impedance of tissue rises due to vaporization, electrical conductivity drops precipitously, thereby effectively preventing further delivery of energy to target tissues. In some embodiments, by terminating energy pulses before tissue impedance rises to this level (e.g., by impedance monitoring or time modulation), this deleterious effect may be avoided. In accordance with several embodiments, char formation is a consequence of tissue vaporization and carbonization, resulting from rapid increases in impedance, electrical arcing, and thrombus formation. By preventing impedance rises, charring of tissue may be avoided.

In some embodiments, total energy delivery is monitored by calculating the time integral of power output (which may be previously correlated to ablation characteristics) to track the progress of the therapy. In some embodiments, the relationship between temperature, time, and electrical field is monitored to obtain an estimate of the temperature field within the tissue surrounding the ablation electrode using the Arrhenius relationship. In some embodiments, a known thermal input is provided to the ablation electrode, on demand, in order to provide known initial conditions for assessing the surrounding tissue response. In some embodiments, a portion of the ablation region is temporarily cooled, and the resultant temperature is decreased. For example, for an endovascular ablation that has been in progress for a period of time, it may be expected that there is some elevated temperature distribution within the tissue. If a clinician wants to assess the progress of the therapy at a given time (e.g., $t_0$), the energy delivery can be interrupted, and cooled saline or gas can be rapidly circulated through the electrode to achieve a predetermined electrode temperature within a short period of time (e.g., about 1 second). In some embodiments, the resulting temperature rise (e.g., over about 5 seconds) measured at the electrode surface is then a representation of the total energy of the surrounding tissue. This process can be repeated through the procedure to track progress.

In some embodiments, a parameter, such as temperature, infrared radiation, or microwave radiation can be monitored to assess the magnitude of energy delivered to tissue, and thus estimate the degree of neuromodulation induced. Both the magnitude of thermal radiation (temperature), infrared radiation, and/or microwave radiation may be indicative of the amount of energy contained within a bodily tissue. In some embodiments, the magnitude is expected to decrease following the completion of the ablation as the tissue cools back towards body temperature, and the rate of this decrease, measured at a specific point (e.g., at the vessel lumen surface) can be used to assess the size of the ablation (e.g., slower decreases may correspond to larger ablation sizes). Any of the embodiments described herein may be used individually or in combination to indicate the actual size of the tissue lesion zone.

In various embodiments, the rate change of various treatment parameters (e.g., impedance, electrode temperature, tissue temperature, power, current, voltage, time, and/or energy is monitored substantially in real time and displayed on a user interface. Treatment parameter data may be stored on a data store for later reporting and/or analysis. In some embodiments, an energy delivery system receives inputs transduced from physiologic signals such as blood glucose levels, norepinephrine levels, or other physiological parameters indicative of the status of the progress of treatment.

Other methods of observing the tissue ablation zone and the surrounding anatomy may include prior, concomitant, or subsequent imaging intravascularly by modalities including but not limited to: intravascular ultrasound, optical coherence tomography, confocal microscopy, infrared spectroscopy, ultraviolet spectroscopy, Raman spectroscopy, and microwave thermometry. All such imaging modalities may advantageously be adapted to the hepatic artery because of its unique tolerance to low flow. In some embodiments, ultrasound elastography is advantageously used for imaging. Ultrasound elastography may show areas of localized tissue stiffness resulting from the denaturing of collagen proteins during thermal ablation (ablated regions tend to stiffen compared to the native tissue); for example, stiff regions may correspond to ablated regions. Intravascular ultrasound may be used for example, to detect or monitor the presence and depth of ablation lesions. For example, if the lesions are in the range of 2 to 6 mm from the lumen wall, the clinician may be confident that the target nerves were destroyed as a result of thermal coagulation. Extravascular ultrasound imaging may also be used.

2. Ultrasound

In some embodiments, an energy delivery system delivers ultrasonic energy to modulate (e.g., ablate, stimulate) sympathetic nerve fibers in the hepatic plexus. For example, the energy delivery system can employ focused ultrasonic energy such as high-intensity focused ultrasonic (HIFU) energy or low-intensity focused ultrasonic (LIFU) energy to ablate sympathetic nerve fibers. In some embodiments, the energy delivery system includes an ablation catheter connected to one or more ultrasound transducers. For example, the ultrasound transducer(s) can deliver ultrasonic energy to one or more ablation sites to ablate sympathetic nerve fibers in the hepatic plexus. The ultrasonic energy can be controlled by dosing, pulsing, or frequency selection. In some embodiments, HIFU energy can advantageously be focused at a distant point to reduce potential disturbance of the tissue of the blood vessel (e.g., the intima and the media layers) or surrounding tissues. HIFU energy can advantageously reduce the precision required for positioning of the ablation catheter. The one or more ultrasound transducers can be refocused during treatment to increase the number of treatment sites or to adjust the depth of treatment. In some embodiments, the use of HIFU energy can result in increased concentrations of heat for a shorter duration and can simultaneously focus energy at multiple focal points, thereby reducing the total time required to administer the neuromodulation procedure.

In some embodiments, the energy delivery system comprises a focused ultrasound (e.g., HIFU) ablation catheter and an acoustic frequency generator. The ablation catheter can be steerable from outside of the subject using a remote mechanism. The distal end of the ablation catheter can be flexible to allow for deflection or rotational freedom about an axis of the catheter shaft to facilitate positioning within a hepatic or other artery. For example, the one or more ultrasound transducers, which may be single element or multiple element transducers, against the intima of the artery or spaced at a distance from the intimal layer. In some embodiments, the ablation catheter comprises focusing (e.g., parabolic) mirrors or other reflectors, gas-filled or liquid-filled balloons, and/or other structural focusing elements to facilitate delivery of the ultrasonic energy. The one or more transducers can be cylindrical, rectangular, elliptical, or any other shape. The ablation catheter can comprise sensors and control circuits to monitor temperature and prevent overheating or to acquire other data corresponding to the one or more ultrasound transducers, the vessel wall and/or the blood flowing across the ultrasound transducer. In some embodiments, the sensors provide feedback to control delivery of the ultrasonic energy. In some embodiments, the ultrasound energy is controlled such that delivery of the ultrasound energy heats the arterial tissue in the range of about 40 to about 90° C. (e.g., 40° C. to 60° C., 60° C. to 75° C., 65° C. to 80° C., 60° C. to 90° C., or overlapping ranges thereof. In some embodiments, the temperature can be less than 40° C. or greater than 90° C.

The frequencies used to ablate the sympathetic nerves can vary based on expected attenuation, the containment of the beam both laterally and axially, treatment depths, type of nerve, and/or other parameters. In some embodiments, the frequencies used range from about 20 kHz to about 20 MHz, from about 500 kHz to about 10 MHz, from about 1 MHz to about 5 MHz, from about 2 MHz to about 6 MHz, from about 3 MHz to about 8 MHz, less than 20 kHz, greater than 20 MHz or overlapping ranges thereof. However, other frequencies can be used without limiting the scope of the disclosure. In some embodiments, the HIFU catheter can also transmit frequencies that can be used for imaging purposes or for confirmation of successful ablation or denervation purposes. In some embodiments, the HIFU catheter delivers energy having parameters such that cavitation does not occur. The average ultrasound intensity for ablation of sympathetic nerve fibers in the hepatic plexus, celiac plexus or other sympathetic nerve fibers can range from about 1 W/cm$^2$ to about 10 kW/cm$^2$, from about 500 W/cm$^2$ to about 5 kW/cm$^2$, from about 2 W/cm$^2$ to about 8 kW/cm$^2$, from about 1 kW/cm$^2$ to about 10 kW/cm$^2$, from about 25 W/cm$^2$ to about 200 W/cm$^2$, from about 200 W/cm$^2$ to about 1 MW/cm$^2$, less than 1 W/cm$^2$, greater than 10 kW/cm$^2$, or overlapping ranges thereof. Power levels may range from about 25 W/cm$^2$ to about 1 MW/cm$^2$ (depending on the intensity of the ultrasound energy and/or other parameters). The ultrasound energy can be continuous or pulsed. The power levels or energy density levels used for pulsed ultrasound energy may be higher than the power levels used for continuous ultrasound energy.

The treatment time for each target ablation site can range from about 5 seconds to about 120 seconds, from about 10 seconds to about 60 seconds, from about 20 seconds to about 80 seconds, from about 30 seconds to about 90 seconds, less than 10 seconds, greater than 120 seconds, one minute to fifteen minutes, ten minutes to one hour, or overlapping ranges thereof. In accordance with several embodiments, the parameters used are selected to disable, block, cease or otherwise disrupt conduction of sympathetic nerves of the hepatic plexus for at least several months while creating minimal damage of the arterial walls or surrounding tissues or organs.

3. Lasers

In several embodiments, lasers may be used to modulate (e.g., ablate) sympathetic nerve activity of the hepatic plexus or other nerves innervating the liver. Although lasers are not generally used for arterial nerve ablation in other arteries, the wall thickness of the hepatic arteries is substantially less than the thickness of other arterial structures, thereby rendering laser energy delivery possible. In some embodiments, one or more lasers are used to ablate nerves located within about 2 mm of the intimal surface, within about 1.5 mm of the intimal surface, within about 1 mm of the intimal surface, or within about 0.5 mm of the intimal surface of a hepatic artery. In some embodiments, chromophore staining of sympathetic fibers is performed to selectively enhance sympathetic nerve absorption of laser energy. In some embodiments, balloons are used to stretch the hepatic artery, thereby thinning the arterial wall and decreasing the depth from the intimal surface to the sympathetic nerve fibers, and thereby improving the delivery of the laser energy.

Other forms of optical or light energy may also be used. The light source may include an LED light source, an electroluminescent light source, an incandescent light source, a fluorescent light source, a gas laser, a chemical laser, a dye laser, a metal-vapor laser, a solid state laser, a semiconductor laser, a vertical cavity surface emitting laser, or other light source. The wavelength of the optical or laser energy may range from about 300 nm to about 2000 nm, from about 500 nm to about 1100 nm, from about 600 nm to about 1000 nm, from about 800 nm to about 1200 nm, from about 1000 nm to about 1600 nm, or overlapping ranges thereof.

4. Externally-Initiated

Figure 18:
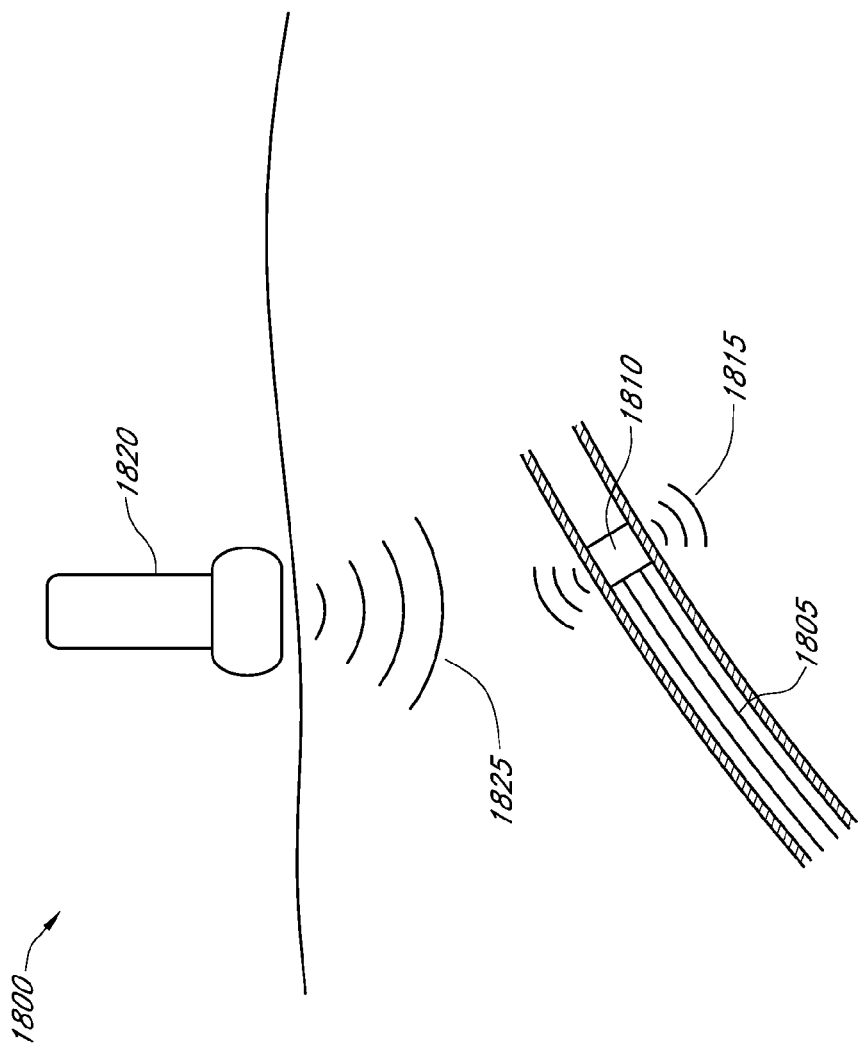
FIG. 18 illustrates an embodiment of a microwave-based ablation catheter system.

In accordance with various embodiments, energy delivery is initiated from a source external to the subject (e.g., extracorporeal activation). FIG. 18 illustrates an embodiment of a microwave-based energy delivery system 1800. The microwave-based energy delivery system 1800 comprises an ablation catheter 1805 and a microwave generating device 1820. In some embodiments, other energy sources may also be delivered externally.

In some embodiments, the ablation catheter 1805 comprises a high conductivity probe 1810 disposed at its distal end. In operation, the ablation catheter 1805 may be inserted into a target vessel and positioned such that the high conductivity probe 1810 is proximate to the site targeted for ablation. The microwave generating device 1820 is located outside a subject's body and positioned such that focused microwaves 1825 are delivered towards the target vessel and the high conductivity probe 1810. In several embodiments, when the delivered focused microwaves 1825 contact the high conductivity probe 1810, they induce eddy currents within the high conductivity probe 1810, thereby heating the high conductivity probe 1810. The thermal energy 1815 generated from the heating of the high conductivity probe can heat the target tissue through conductive heat transfer. In some embodiments, the thermal energy 1815 generated is sufficient to ablate nerves within or disposed on the target tissue (e.g., vessel wall). In various embodiments, the high conductivity probe 1810 has a conductivity greater than 10^1 Siemens/meter.

Figure 19:
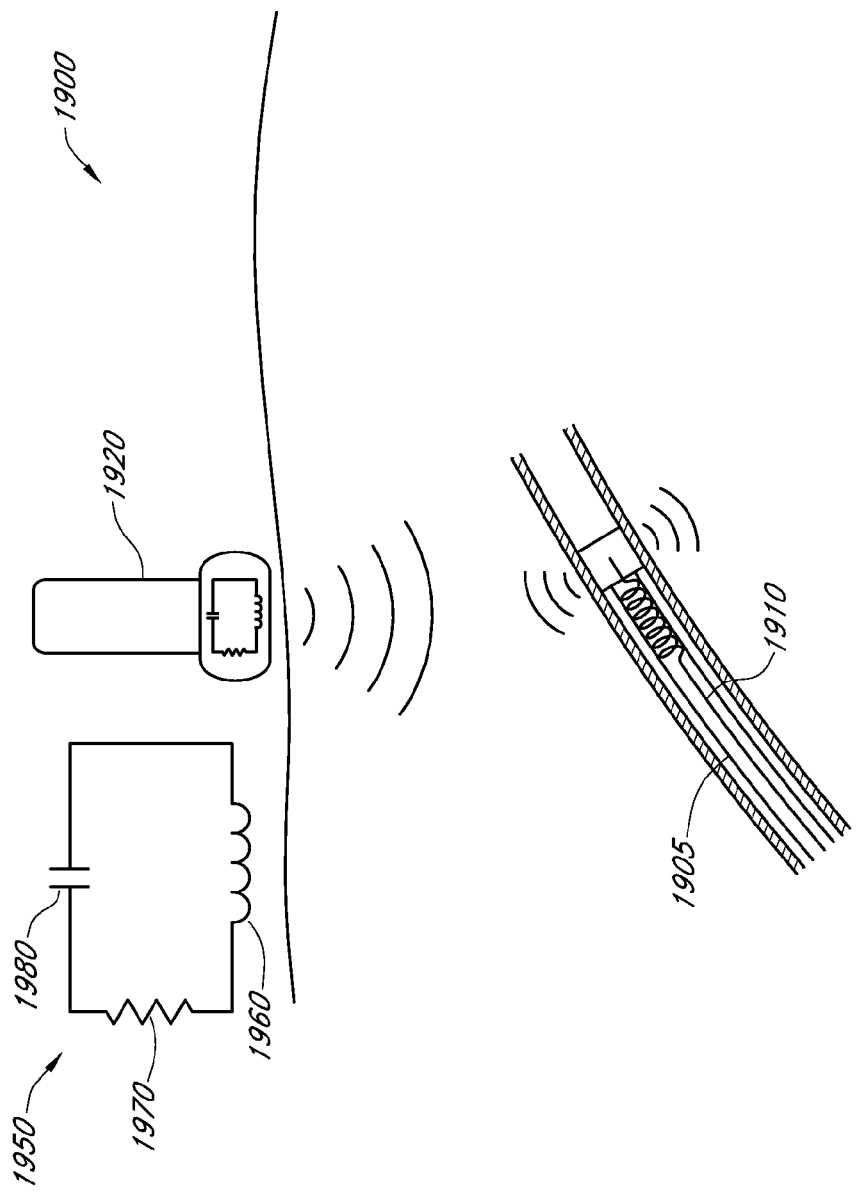
FIG. 19 illustrates an embodiment of an induction-based ablation catheter system.

FIG. 19 illustrates an embodiment of an induction-based energy delivery catheter system 1900. In the illustrated embodiment, the induction-based energy delivery system 1900 comprises a catheter 1905, an induction coil 1910, an external inductor power circuit 1950, an inductor 1960, a resistor 1970, and a capacitor 1980. In one embodiment, the induction coil 1910 is disposed at the distal end of the catheter 1905. In operation, the induction coil 1910 may act as an inductor to receive energy from the external inductive power circuit 1950. In some embodiments, the external inductive power circuit 1950 is positioned such that the inductor 1960 is adjacent the induction coil 1910 within a sufficient induction range. In some embodiments, current is delivered through the external inductive power circuit 1950, thereby causing current to flow in the induction coil 1910 and delivering subsequent ablative energy to surrounding tissues. In one embodiment, an induction coil is used in combination with any of the windowed catheter devices described herein (such as the windowed catheter devices described in connection with FIGS. 16A and 16B). For example, the induction coil may be placed within a lumen of a catheter or sleeve having one or more windows configured to permit the selective delivery of energy to the target tissue.

In some embodiments, one or more synthetic emboli may be inserted within a target vessel and implanted or lodged therein (at least temporarily). The synthetic emboli may advantageously be sized to match the anatomy of the target vessel (e.g., based on angiography of the target location and vessel diameter). The synthetic emboli may be selected based on a measured or estimated dimension of the target vessel. In one embodiment, an energy delivery catheter is coupled to the one or more synthetic emboli inserted within a target vessel to deliver energy. In some embodiments, energy is delivered transcutaneously to the synthetic emboli using inductive coupling as described in connection with FIG. 21, thereby eliminating the need for an energy delivery catheter. The synthetic emboli may comprise an induction coil and a plurality of electrodes embedded within an insulating support structure comprised of high dielectric material. After appropriate energy has been delivered to modulate nerves associated with the target vessel, the one or more emboli may be removed.

In several embodiments of the invention, the energy-based delivery systems comprise cooling systems that are used to, for example, reduce thermal damage to regions surrounding the target area. For example, cooling may lower (or maintain) the temperature of tissue at below a particular threshold temperature (e.g., at or between 40 to 50 degrees Celsius), thereby preventing or reducing cell necrosis. Cooling balloons or other expandable cooling members are used in some embodiments. In one embodiment, ablation electrodes are positioned on a balloon, which is expanded using cooling fluid. In some embodiments, cooling fluid is circulated through a delivery system (e.g., a catheter system). In some embodiments, cooling fluid (such as pre-cooled saline) may be delivered (e.g., ejected) from a catheter device in the treatment region. In further embodiments, cooling fluid is continuously or intermittently circulated internally within the catheter device to cool the endothelial wall in the absence of sufficient blood flow.

D. Steam/Hot Water Neuromodulation

Figure 20:
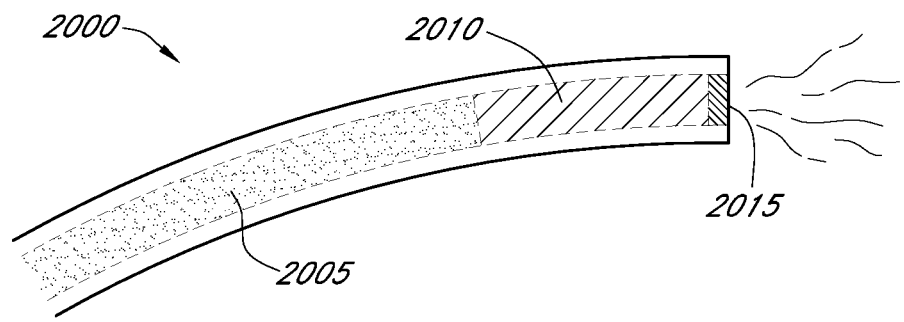
FIG. 20 illustrates an embodiment of a steam ablation catheter.

FIG. 20 illustrates an embodiment of a steam ablation catheter 2000. In the illustrated embodiment, the steam ablation catheter 2000 comprises a water channel 2005, a steam generating head 2010, and a steam outlet 2015. In operation, water may be forced through the water channel 2005 and caused to enter the steam generating head 2010. In one embodiment, the steam generating head 2010 converts the water into steam, which exits the steam ablation catheter 2000 through the steam outlet 2015.

In some embodiments, steam is used to ablate or denervate the target anatomy (e.g., hepatic arteries and nerves associated therewith). In accordance with several embodiments, water is forced through the ablation catheter 2000 and out through the steam generating head 2010 (which converts the water into steam) and the steam is directed to an ablation target. The steam ablation catheter 2000 may comprise one or more window along the length of the catheter body.

Figure 21:
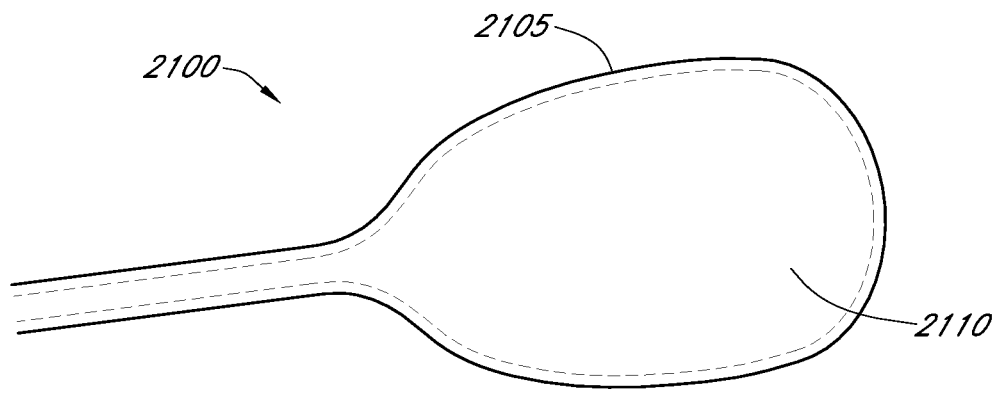
FIG. 21 illustrates an embodiment of a hot water balloon ablation catheter.

FIG. 21 illustrates an embodiment of a hot fluid balloon ablation catheter 2100. In the illustrated embodiment, the hot fluid balloon ablation catheter 2100 comprises an inflatable balloon 2105. In some embodiments, the inflatable balloon 2105 is filled with a temperature variable fluid 2110. In accordance with several embodiments, hot water is the temperature variable fluid 2110 used to fill the inflatable balloon 2105. The heat generated from the hot fluid within the inflatable balloon may be sufficient to ablate or denervate the target anatomy (e.g., hepatic arteries and nerves associated therewith). In some embodiments, the inflatable balloon 2105 is inserted to the ablation site and inflated with scalding or boiling fluid (e.g., water), thereby heating tissue surrounding the inflatable balloon 2105 sufficient to ablate or denervate the tissue. In some embodiments, the hot fluid within the balloon 2105 is within the temperature range of about 120° F. to about 212° F., from about 140° F. to about 212° F., from about 160° F. to about 212° F., from about 180° F. to about 212° F., about 200° F. to about 212° F., or overlapping ranges thereof. In some embodiments, the balloon ablation catheter 2100 comprises a temperature sensor and fluid (e.g., water) at different temperatures may be inserted and withdrawn as treatment dictates. In some embodiments, the inflatable balloon 2105 is made out of polyurethane or any other heat-resistant inflatable material.

E. Chemical Neuromodulation

In some embodiments, drugs are used alone or in combination with another modality to cause neuromodulation. Drugs include, but are not limited to, muscarinic receptor agonists, anticholinesterase agents, nicotinic receptor agonists, and nicotine receptor antagonists. Drugs that directly affect neurotransmission synthesis, degradation, or reuptake are used in some embodiments.

In some embodiments, drugs (either alone or in combination with energy modalities) can be used for neuromodulation. For example, a delivery catheter may have one or more internal lumens. In some embodiments, one or more internal lumens are in fluid communication with a proximal opening and with a distal opening of the delivery catheter. In some embodiments, at least one distal opening is located at the distal end of the delivery catheter. In some embodiments, at least one proximal opening is located at the proximal end of the delivery catheter. In some embodiments, the at least one proximal opening is in fluid communication with at least one reservoir.

In some embodiments, at least one reservoir is a drug reservoir that holds drugs or therapeutic agents capable of modulating sympathetic nerve fibers in the hepatic plexus. In some embodiments, a separate drug reservoir is provided for each drug used with the delivery catheter system. In other embodiments, at least one drug reservoir may hold a combination of a plurality of drugs or therapeutic agents. Any drug that is capable of modulating nerve signals may be used in accordance with the embodiments disclosed herein. In some embodiments, neurotoxins (e.g., botulinum toxins) are delivered to the liver, pancreas, or other surrounding organs or nerves associated therewith. In some embodiments, neurotoxins (e.g., botulinum toxins) are not delivered to the liver, pancreas, or other surrounding organs or nerves associated therewith.

In some embodiments, a delivery catheter system includes a delivery device that delivers one or more drugs to one or more target sites. For example, the delivery device may be a pump. Any pump, valve, or other flow regulation member capable of delivering drugs through a catheter may be used. In some embodiments, the pump delivers at least one drug from the at least one drug reservoir through the at least one internal lumen of the catheter delivery system to the one or more target sites.

In some embodiments, the pump selects the drug dosage to be delivered from the reservoir to the target site(s). For example, the pump can selectively vary the total amount of one or more drugs delivered as required for neuromodulation. In some embodiments, a plurality of drugs is delivered substantially simultaneously to the target site. In other embodiments, a plurality of drugs is delivered in series. In other embodiments, a plurality of drugs is delivered substantially simultaneously and at least one other drug is delivered either before or after the plurality of drugs is delivered to the target site(s). Drugs or other agents may be used without delivery catheters in some embodiments. According to several embodiments, drugs may have an inhibitory or stimulatory effect.

In some embodiments, an ablation catheter system uses chemoablation to ablate nerve fibers (e.g., sympathetic nerve fibers in the hepatic plexus). For example, the ablation catheter may have one or more internal lumens. In some embodiments, one or more internal lumens are in fluid communication with a proximal opening and with a distal opening. In some embodiments, at least one distal opening is located in the distal end of an ablation catheter. In some embodiments, at least one proximal opening is located in the proximal end of the ablation catheter. In some embodiments, at least one proximal opening is in fluid communication with at least one reservoir.

In some embodiments, at least one reservoir holds and/or stores one or more chemicals capable of disrupting (e.g., ablating, desensitizing, destroying) nerve fibers (e.g., sympathetic nerve fibers in the hepatic plexus). In some embodiments, a separate reservoir is provided for each chemical used with the ablation catheter system. In other embodiments, at least one reservoir may hold any combination of chemicals. Any chemical that is capable of disrupting nerve signals may be used in accordance with the embodiments disclosed herein. For example, one or more chemicals or desiccants used may include phenol or alcohol, guanethidine, zinc sulfate, nanoparticles, radiation sources for brachytherapy, neurostimulants (e.g., methamphetamine), and/or oxygen radicals (e.g., peroxide). However, any chemical that is capable of ablating sympathetic nerve fibers in the hepatic plexus may be used in accordance with the embodiments disclosed herein. In some embodiments, chemoablation is carried out using a fluid delivery needle delivered percutaneously, laparascopically, or via an intravascular approach.

F. Cryomodulation

In some embodiments, the invention comprises cryotherapy or cryomodulation. In one embodiment, the ablation catheter system uses cryoablation techniques for neuromodulation. In one embodiment, cryoablation is used to ablate sympathetic nerve fibers in the hepatic plexus. For example, the ablation catheter may have one or more internal lumens. In some embodiments, one or more internal lumens are in fluid communication with a proximal opening. In some embodiments, at least one proximal opening is located in the proximal end of the ablation catheter. In some embodiments, at least one proximal opening is in fluid communication with at least one reservoir (e.g., a cryochamber). In some embodiments, the at least one reservoir holds one or more coolants including but not limited to liquid nitrogen. The ablation catheter can comprise a feed line for delivering coolant to a distal tip of the ablation catheter and a return line for returning spent coolant to the at least one reservoir. The coolant may reach a temperature sufficiently low to freeze and ablate sympathetic nerve fibers in the hepatic plexus. In some embodiments, the coolant can reach a temperature of less than 75 degrees Celsius below zero, less than 80 degrees Celsius below zero, less than 90 degrees Celsius below zero, or less than 100 degrees Celsius below zero.

In some embodiments, the ablation catheter system includes a delivery device that controls delivery of one or more coolants through one or more internal lumens to the target site(s). For example, the delivery device may be a pump. Any pump, valve or other flow regulation member that is capable of delivering coolants through a catheter may be used. In some embodiments, the pump delivers at least one coolant from at least one reservoir, through at least one proximal opening of the catheter body, through at least one internal lumen of the catheter body, and to the distal end of the ablation catheter (e.g., via a feed line or coolant line).

In some embodiments, the target nerves may be irreversibly cooled using an implantable Peltier cooling device. In some embodiments, an implantable cooling device is configured to be refilled with an inert gas that is injected at pressure into a reservoir within the implantable device and then released selectively in the vicinity of the target nerves, cooling them in an adiabatic fashion, thereby slowing or terminating nerve conduction (either temporarily or permanently). In some embodiments, local injections or infusion of ammonium chloride is used to induce a cooling reaction sufficient to alter or inhibit nerve conduction. In some embodiments, delivery of the coolant to the distal end of the ablation catheter, which may comprise one or more ablation electrodes or a metal-wrapped cylindrical tip, causes denervation of sympathetic nerve fibers in the hepatic plexus. For example, when the ablation catheter is positioned in or near the proper hepatic artery or the common hepatic artery, the temperature of the coolant may cause the temperature of the surrounding area to decrease sufficiently to denervate sympathetic nerve fibers in the hepatic plexus. In some embodiments, cryoablation is performed using a cryocatheter. Cryoablation can alternatively be performed using one or more probes alone or in combination with a cryocatheter.

The treatment time for each target ablation site can range from about 5 seconds to about 100 seconds, 5 minutes to about 30 minutes, from about 10 minutes to about 20 minutes from about 5 minutes to about 15 minutes, from about 10 minutes to about 30 minutes, less than 5 seconds, greater than 30 minutes, or overlapping ranges thereof. In accordance with several embodiments, the parameters used are selected to disable, block, cease or otherwise disrupt conduction of, for example, sympathetic nerves of the hepatic plexus. The effects on conduction of the nerves may be permanent or temporary. One, two, three, or more cooling cycles can be used.

In some embodiments, any combination of drug delivery, chemoablation, and/or cryoablation is used for neuromodulation, and may be used in combination with an energy modality. In several embodiments, cooling systems are provided in conjunction with energy delivery to, for example, protect tissue adjacent the nerve fibers.

III. Image Guidance, Mapping and Selective Positioning

Image guidance techniques may be used in accordance with several of the embodiments disclosed herein. For example, a visualization element (e.g., a fiber optic scope) may be provided in combination with a catheter-based energy or fluid delivery system to aid in delivery and alignment of a neuromodulation catheter. In other embodiments, fluoroscopic, ultrasound, Doppler or other imaging is used to aid in delivery and alignment of the neuromodulation catheter. In some embodiments, radiopaque markers are located at the distal end of the neuromodulation catheter or at one or more locations along the length of the neuromodulation catheter. For example, for catheters having electrodes, at least one of the electrodes may comprise a radiopaque material. Computed tomography (CT), fluorescence, radiographic, thermography, Doppler, optical coherence tomography (OCT), intravascular ultrasound (IVUS), and/or magnetic resonance (MR) imaging systems, with or without contrast agents or molecular imaging agents, can also be used to provide image guidance of a neuromodulation catheter system. In some embodiments, the neuromodulation catheter comprises one or more lumens for insertion of imaging, visualization, light delivery, aspiration or other devices.

In accordance with some embodiments, image or visualization techniques and systems are used to provide confirmation of disruption (e.g., ablation, destruction, severance, denervation) of the nerve fibers being targeted. In some embodiments, the neuromodulation catheter comprises one or more sensors (e.g., sensor electrodes) that are used to provide confirmation of disruption (e.g., ablation, destruction, severance, denervation) of communication of the nerve fibers being targeted.

In some embodiments, the sympathetic and parasympathetic nerves are mapped prior to modulation. In some embodiments, a sensor catheter is inserted within the lumen of the vessel near a target modulation area. The sensor catheter may comprise one sensor member or a plurality of sensors distributed along the length of the catheter body. After the sensor catheter is in place, either the sympathetic nerves or the parasympathetic nerves may be stimulated. In some embodiments, the sensor catheter is configured to detect electrical activity. In some embodiments, when the sympathetic nerves are artificially stimulated and parasympathetic nerves are left static, the sensor catheter detects increased electrical activity and the data obtained from the sensor catheter is used to map the sympathetic nervous geometry. In some embodiments, when the parasympathetic nerves are artificially stimulated and sympathetic nerves are left static, the sensor catheter detects increased electrical activity and the data obtained from the sensor catheter is used to map the parasympathetic nervous geometry. In some embodiments, mapping the nervous geometry using nervous stimulation and the sensor catheter advantageously facilitates improved or more informed selection of the target area to modulate, leaving select nerves viable while selectively ablating and disrupting others. As an example of one embodiment, to selectively ablate sympathetic nerves, the sympathetic nerves may be artificially stimulated while a sensor catheter, already inserted, detects and maps areas of increased electrical activity. To disrupt the sympathetic nerves, only the areas registering increased electrical activity may need to be ablated.

In one embodiment, a method of targeting sympathetic nerve fibers involves the use of electrophysiology mapping tools. While applying central or peripheral nervous signals intended to increase sympathetic activity (e.g., by administering noradrenaline or electrical stimulation), a sensing catheter may be used to map the geometry of the target vessel (e.g., hepatic artery) and highlight areas of increased electrical activity. An ablation catheter may then be introduced and activated to ablate the mapped areas of increased electrical activity, as the areas of increased electrical activity are likely to be innervated predominantly by sympathetic nerve fibers. In some embodiments, nerve injury monitoring (NIM) methods and devices are used to provide feedback regarding device proximity to sympathetic nerves located perivascularly. In one embodiment, a NIM electrode is connected laparoscopically or thoracoscopically to sympathetic ganglia.

In some embodiments, to selectively target the sympathetic nerves, local conductivity may be monitored around the perimeter of the hepatic artery. Locations corresponding to maximum impedance are likely to correspond to the location of the sympathetic nerve fibers, as they are furthest away from the bile duct and portal vein, which course posterior to the hepatic artery and which are highly conductive compared to other tissue surrounding the portal triad. In some methods, to selectively disrupt sympathetic nerves, locations with increased impedance are selectively modulated (e.g., ablated). In some embodiments, one or more return electrodes are placed in the portal vein and/or bile duct to enhance the impedance effects observed in sympathetic nervous tissues. In some embodiments, return electrodes are placed on areas of the skin perfused with large veins and having decreased fat and/or non-vascular tissues (such as the neck or wrist, etc.). The resistance between the portal vein and other veins may be very low because of the increased electrical conductivity of blood relative to other tissues. Therefore, the impedance effects may be enhanced because comparatively small changes in resistance between various positions on the hepatic artery and the portal vein are likely to have a relatively large impact on the overall resistance registered.

In some embodiments, the sympathetic nerves are targeted locationally. It may be observed in some subjects that sympathetic nerve fibers tend to run along a significant length of the proper hepatic artery while the parasympathetic nerve fibers tend to join towards the distal extent of the proper hepatic artery. In some embodiments, sympathetic nerves are targeted by ablating the proper hepatic artery towards its proximal extent (e.g., generally half-way between the first branch of the celiac artery and the first branch of the common hepatic artery or about one centimeter, about two centimeters, about three centimeters, about four centimeters, or about five centimeters beyond the proper hepatic artery branch). Locational targeting may be advantageous because it can avoid damage to critical structures such as the bile duct and portal vein, which generally approach the hepatic artery as it courses distally towards the liver.

In some embodiments, neuromodulation location is selected by relation to the vasculature's known branching structure (e.g., directly after a given branch). In some embodiments, neuromodulation location is selected by measurement (e.g., insertion of a certain number of centimeters into the target vessel). Because the relevant nervous and vessel anatomy is highly variable in humans, it may be more effective in some instances to select neuromodulation location based on a position relative to the branching anatomy, rather than based on a distance along the hepatic artery. In some subjects, nerve fiber density is qualitatively increased at branching locations.

In some embodiments, a method for targeting sympathetic nerve fibers comprises assessing the geometry of arterial structures distal of the celiac axis using angiography. In one embodiment, the method comprises characterizing the geometry into any number of common variations and then selecting neuromodulation (e.g., ablation) locations based on the expected course of the parasympathetic nerve fibers for a given arterial variation. Because arterial length measurements can vary from subject to subject, in some embodiments, this method for targeting sympathetic nerve fibers is performed independent of arterial length measurements. The method may be used for example, when it is desired to denervate or ablate a region adjacent and proximal to the bifurcation of the common hepatic artery into the gastroduodenal and proper hepatic arteries.

In the absence of nerve identification under direct observation, nerves can be identified based on their physiologic function. In some embodiments, mapping and subsequent modulation is performed using glucose and norepinephrine ("NE") levels. In some embodiments, glucose and NE levels respond with fast time constants. Accordingly, a clinician may stimulate specific areas (e.g., in different directions or circumferential clock positions or longitudinal positions) in a target artery or other vessel, monitor the physiologic response, and then modulate (e.g., ablate) only in the locations that exhibited the undesired physiologic response. Sympathetic nerves tend to run towards the anterior portion of the hepatic artery, while the parasympathetic nerves tend to run towards the posterior portion of the hepatic artery. Therefore, one may choose a location not only anterior, but also (using the aforementioned glucose and NE level measurements) a specific location in the anterior region that demonstrated the strongest physiologic response to stimulation (e.g., increase in glucose levels due to sympathetic stimulation). In some embodiments, stimulation with 0.1 s-on, 4.9 s-off, 14 Hz, 0.3 ms, 4 mA pulsed RF energy is a sympathetic activator and stimulation with 2 s-on, 3 s-off, 40 Hz, 0.3 ms, 4 mA pulsed RF energy is a parasympathetic activator. However, other parameters of RF energy or other energy types may be used.

In some embodiments, using electrical and/or positional selectivity, a clinician could apply a stimulation pulse or signal and monitor a physiologic response. Some physiologic responses that may indicate efficacy of treatment include, but are not limited to, the following: blood glucose levels, blood and/or tissue NE levels, vascular muscle tone, blood insulin levels, blood glucagon levels, blood C peptide levels, blood pressure (systolic, diastolic, average), and heart rate. In some cases, blood glucose and tissue NE levels may be the most accurate and readily measured parameters. The physiologic responses may be monitored or assessed by arterial or venous blood draws, nerve conduction studies, oral or rectal temperature readings, or percutaneous or surgical biopsy. In some embodiments, transjugular liver biopsies are taken after each incremental ablation to measure the resultant reduction in tissue NE levels and treatment may be titrated or adjusted based on the measured levels. For example, in order to measure tissue NE levels in the liver, a biopsy catheter may be inserted by a TIPS approach or other jugular access to capture a sample of liver parenchyma. In some embodiments, the vein wall of the portal vein may safely be violated to obtain the biopsy, as the vein is surrounded by the liver parenchyma, thereby preventing blood loss.

In some embodiments, ablation is performed using an ablation catheter with radiopaque indicators capable of indicating proper position when viewed using fluoroscopic imaging. Due to the two-dimensional nature of fluoroscopic imaging, device position can only be determined along a single plane, providing a rectangular cross-section view of the target vasculature. In order to overcome the difficulty of determining device position along a vessel circumference without repositioning the fluoroscopic imaging system, rotational positioning indicators that are visible using fluoroscopic imaging may advantageously be incorporated on an endovascular ablation device to indicate the circumferential position of ablation components (e.g., electrodes) relative to the vessel anatomy.

In one embodiment, an ablation catheter having an ablation electrode comprises three radiopaque indicators positioned along the longitudinal axis of the ablation catheter. In one embodiment, the first radiopaque indicator is positioned substantially adjacent to the electrode on the device axis; the second radiopaque indicator is positioned proximal to the electrode on the device axis; and the third radiopaque indicator is positioned off the device axis. In one embodiment, the third radiopaque indicator is positioned between the first and second radiopaque indicators. In embodiments with three radiopaque indicators, the ablation electrode is configured to contact the vessel wall through deflection from the central axis of the catheter. In one embodiment, alignment of the first and second radiopaque indicators means that the ablation electrode is located in a position spaced from, and directly perpendicular to, the imaging plane (e.g., either anteriorly or posteriorly assuming a coronal imaging plane). In one embodiment, the position of the third radiopaque indicator indicates the anterior-posterior orientation. For example, position of the third radiopaque indicator above, on, or below the line formed between the first and second radiopaque indicators may provide the remaining information necessary to allow the user to infer the position of the ablation catheter.

IV. Alternative Catheter Delivery Methods

In addition to being delivered intravascularly through an artery, the neuromodulation systems described herein (e.g., ablation catheter systems) can be delivered intravascularly through the venous system. For example, an ablation catheter system may be delivered through the portal vein. In other embodiments, an ablation catheter system is delivered intravascularly through the inferior vena cava. Any other intravascular delivery method or approach may be used to deliver neuromodulation systems, e.g., for modulation of sympathetic nerve fibers in the hepatic plexus.

In some embodiments, the neuromodulation systems (e.g., catheter systems) are delivered transluminally to modulate nerve fibers. For example, catheter systems may be delivered transluminally through the stomach. In other embodiments, the catheter systems are delivered transluminally through the duodenum, or transluminally through the biliary tree via endoscopic retrograde cholangiopancreatography (ERCP). Any other transluminal or laparoscopic delivery method may be used to deliver the catheter systems according to embodiments described herein.

In some embodiments, the catheter systems are delivered percutaneously to the biliary tree to ablate sympathetic nerve fibers in the hepatic plexus. Any other minimally invasive delivery method may be used to deliver neuromodulation systems for modulation or disruption of sympathetic nerve fibers in the hepatic plexus as desired and/or required.

In some embodiments, an open surgical procedure is used to modulate sympathetic nerve fibers in the hepatic plexus. Any open surgical procedure may be used to access the hepatic plexus. In conjunction with an open surgical procedure, any of the modalities described herein for neuromodulation may be used. For example, RF ablation, ultrasound ablation, HIFU ablation, ablation via drug delivery, chemoablation, cryoablation, ionizing energy delivery (such as X-ray, proton beam, gamma rays, electron beams, and alpha rays) or any combination thereof may be used with an open surgical procedure. In one embodiment, nerve fibers (e.g., in or around the hepatic plexus) are surgically cut in conjunction with an open surgical procedure in order to disrupt sympathetic signaling, e.g., in the hepatic plexus.

In some embodiments, a non-invasive procedure or approach is used to ablate sympathetic nerve fibers in the hepatic plexus and/or other nerve fibers. In some embodiments, any of the modalities described herein, including, but not limited, to ultrasonic energy, HIFU energy, electrical energy, magnetic energy, light/radiation energy or any other modality that can effect non-invasive ablation of nerve fibers, are used in conjunction with a non-invasive (e.g., transcutaneous) procedure to ablate sympathetic nerve fibers in the hepatic plexus and/or other nerve fibers.

V. Stimulation

According to some embodiments, neuromodulation is accomplished by stimulating nerves and/or increasing neurotransmission. Stimulation, in one embodiment, may result in nerve blocking. In other embodiments, stimulation enhances nerve activity (e.g., conduction of signals).

In accordance with some embodiments, therapeutic modulation of nerve fibers is carried out by neurostimulation of autonomic (e.g., sympathetic or parasympathetic) nerve fibers. Neurostimulation can be provided by any of the devices or systems described above (e.g., ablation catheter or delivery catheter systems) and using any of the approaches described above (e.g., intravascular, laparoscopic, percutaneous, non-invasive, open surgical). In some embodiments, neurostimulation is provided using a temporary catheter or probe. In other embodiments, neurostimulation is provided using an implantable device. For example, an electrical neurostimulator can be implanted to stimulate parasympathetic nerve fibers that innervate the liver, which could advantageously result in a reduction in blood glucose levels by counteracting the effects of the sympathetic nerves.

In some embodiments, the implantable neurostimulator includes an implantable pulse generator. In some embodiments, the implantable pulse generator comprises an internal power source. For example, the internal power source may include one or more batteries. In one embodiment, the internal power source is placed in a subcutaneous location separate from the implantable pulse generator (e.g., for easy access for battery replacement). In other embodiments, the implantable pulse generator comprises an external power source. For example, the implantable pulse generator may be powered via an RF link. In other embodiments, the implantable pulse generator is powered via a direct electrical link. Any other internal or external power source may be used to power the implantable pulse generator in accordance with the embodiments disclosed herein.

In some embodiments, the implantable pulse generator is electrically connected to one or more wires or leads. The one or more wires or leads may be electrically connected to one or more electrodes. In some embodiments, one or more electrodes are bipolar. In other embodiments, one or more electrodes are monopolar. In some embodiments, there is at least one bipolar electrode pair and at least one monopolar electrode. In some embodiments, one or more electrodes are nerve cuff electrodes. In other embodiments, one or more electrodes are conductive anchors.

In some embodiments, one or more electrodes are placed on or near parasympathetic nerve fibers that innervate the liver. In some embodiments, the implantable pulse generator delivers an electrical signal to one or more electrodes. In some embodiments, the implantable pulse generator delivers an electrical signal to one or more electrodes that generates a sufficient electric field to stimulate parasympathetic nerve fibers that innervate the liver. For example, the electric field generated may stimulate parasympathetic nerve fibers that innervate the liver by altering the membrane potential of those nerve fibers in order to generate an action potential.

In some embodiments, the implantable pulse generator recruits an increased number of parasympathetic nerve fibers that innervate the liver by varying the electrical signal delivered to the electrodes. For example, the implantable pulse generator may deliver a pulse of varying duration. In some embodiments, the implantable pulse generator varies the amplitude of the pulse. In other embodiments, the implantable pulse generator delivers a plurality of pulses. For example, the implantable pulse generator may deliver a sequence of pulses. In some embodiments, the implantable pulse generator varies the frequency of pulses. In other embodiments, the implantable pulse generator varies any one or more parameters of a pulse including, but not limited to, duration, amplitude, frequency, and total number of pulses.

In some embodiments, an implantable neurostimulator chemically stimulates parasympathetic nerve fibers that innervate the liver. For example, the chemical neurostimulator may be an implantable pump. In some embodiments, the implantable pump delivers chemicals from an implanted reservoir. For example, the implantable pump may deliver chemicals, drugs, or therapeutic agents to stimulate parasympathetic nerve fibers that innervate the liver.

In some embodiments, the implantable neurostimulator uses any combination of electrical stimulation, chemical stimulation, or any other method to stimulate parasympathetic nerve fibers that innervate the liver.

In some embodiments, non-invasive neurostimulation is used to stimulate parasympathetic nerve fibers that innervate the liver. For example, transcutaneous electrical stimulation may be used to stimulate parasympathetic nerve fibers that innervate the liver. In other embodiments, any method of non-invasive neurostimulation is used to stimulate parasympathetic nerve fibers that innervate the liver.

In accordance with the embodiments disclosed herein, parasympathetic nerve fibers other than those that innervate the liver are stimulated to treat diabetes and/or other conditions, diseases, disorders, or symptoms related to metabolic conditions. For example, parasympathetic nerve fibers that innervate the pancreas, parasympathetic nerve fibers that innervate the adrenal glands, parasympathetic nerve fibers that innervate the small intestine, parasympathetic nerves that innervate the stomach, parasympathetic nerve fibers that innervate the kidneys (e.g., the renal plexus) or any combination of parasympathetic nerve fibers thereof may be stimulated in accordance with the embodiments herein disclosed. Any autonomic nerve fibers can be therapeutically modulated (e.g., disrupted or stimulated) using the devices, systems, and methods described herein to treat any of the conditions, diseases, disorders, or symptoms described herein (e.g., diabetes or diabetes-related conditions). In some embodiments, visceral fat tissue of the liver or other surrounding organs is stimulated. In some embodiments, intrahepatic stimulation or stimulation to the outer surface of the liver is provided. In some embodiments, stimulation (e.g., electrical stimulation) is not provided to the outer surface of the liver or within the liver (e.g., to the liver parenchyma), is not provided to the vagal or vagus nerves, is not provided to the hepatic portal vein, and/or is not provided to the bile ducts.

Stimulation may be performed endovascularly or extravascularly. In one embodiment, a stimulation lead is positioned intravascularly in the hepatic arterial tree adjacent parasympathetic nerves. The main hepatic branch of the parasympathetic nerves may be stimulated by targeting a location in proximity to the proper hepatic artery or multiple hepatic branches tracking the left and right hepatic artery branches and subdivisions. In one embodiment, the stimulation lead is positioned within a portion of the hepatoesophageal artery and activated to stimulate parasympathetic nerves surrounding the hepatoesophageal artery, as both vagal branches travel along the hepatoesophageal artery.

In one embodiment, the stimulation lead is positioned in the portal vein and activated to stimulate nerve fibers surrounding the portal vein, which may have afferent parasympathetic properties. In one embodiment, the stimulation lead is positioned across the hepatic parenchyma from a central venous approach (e.g., via a TIPS-like procedure) or positioned by arterial access through the hepatic artery and then into the portal vein. In one embodiment, the portal vein is accessed extravascularly through a percutaneous approach. The stimulation lead may be longitudinally placed in the portal vein or wrapped around the portal vein like a cuff. Extravascular stimulation of the portal vein may be performed by placing the stimulation lead directly on the parasympathetic fibers adhered to or within the exterior vessel wall. In various embodiments, the stimulation lead is placed percutaneously under fluoroscopy guidance, using a TIPS-like approach through the wall of the portal vein, by crossing the arterial wall, or by accessing the biliary tree.

In some embodiments, the stimulation lead is stimulated continuously or chronically to influence resting hepatic glucose product and glucose uptake. In various embodiments, stimulation is performed when the subject is in a fasting or a fed state, depending on a subject's glucose excursion profile. In some embodiments, stimulation may be programmed to occur automatically at different times (e.g., periodically or based on feedback). For example, a sensory lead may be positioned in the stomach or other location to detect food ingestion and trigger stimulation upon detection. In some embodiments, the stimulation is controlled or programmed by the subject or remotely by a clinician over a network.

In some embodiments, stimulation with 0.1 s-on, 4.9 s-off, 14 Hz, 0.3 ms, 4 mA pulsed RF energy is used for sympathetic nerve stimulation and stimulation with 2 s-on, 3 s-off, 40 Hz, 0.3 ms, 4 mA pulsed RF energy is used for parasympathetic activation. However, other parameters of RF energy or other energy types may be used.

Parasympathetic stimulation may also cause afferent effects along the vagus nerve, in addition to efferent effects to the liver resulting in changes in hepatic glucose production and uptake. The afferent effects may cause other efferent neurally mediated changes in metabolic state, including, but not limited to one or more of the following: an improvement of beta cell function in the pancreas, increased muscle glucose uptake, changes in gastric or duodenal motility, changes in secretion or important gastric and duodenal hormones (e.g., an increase in ghrelin in the stomach to signal satiety, and/or an increase in glucagon-like peptide-1 (GLP-1) from the duodenum to increase insulin sensitivity).

VI. Examples

Examples provided below are intended to be non-limiting embodiments of the invention.

A. Example 1

Figure 23A:
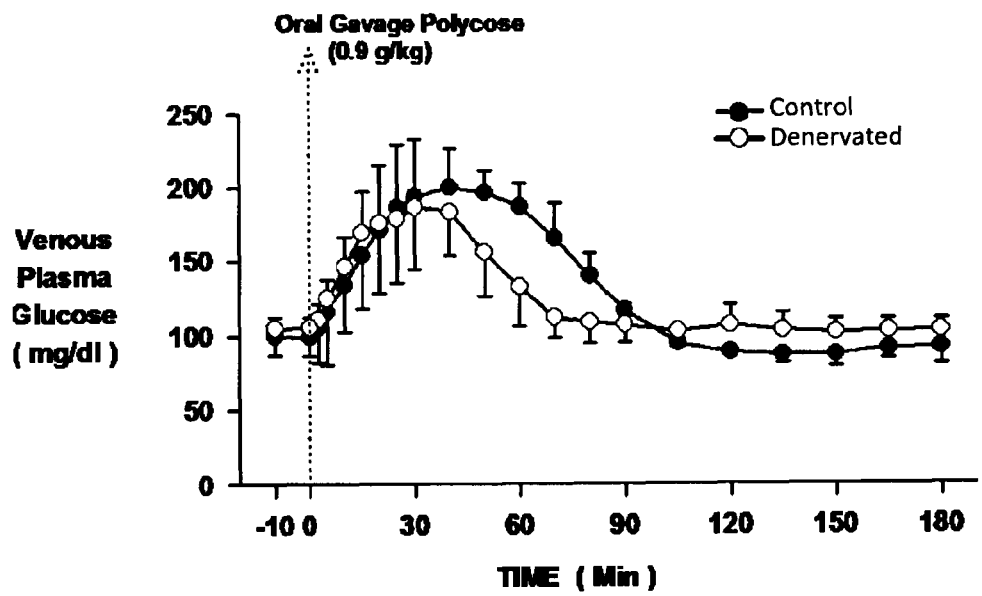
FIGS. 23A and 23B illustrate graphs of data from hepatic denervation studies, in accordance with embodiments of the invention.

Three dogs were put on a high fat, high fructose diet for four weeks, thereby rendering the dogs insulin resistant. As a control, a 0.9 g/kg oral gavage polycose dose was administered at four weeks after initiation of the high-fat, high fructose diet after an overnight fast and oral glucose tolerance tests were performed at various time intervals to track glucose levels. The common hepatic arteries of the three dogs were then surgically denervated. Another 0.9 g/kg oral gave polycose dose was administered after an overnight fast about two to three weeks following hepatic denervation. Oral glucose tolerance tests were performed at various time intervals after administration of the polycose. FIG. 23A illustrates a graph of the average venous plasma glucose over time for the three dogs reported by the two oral glucose tolerance tests (OGTTs). The curve with the data points represented by black circles represents the average of the glucose measurements from the OGTT testing of the three dogs after the four weeks of high fat, high fructose diet before hepatic denervation. The oral gavage polycose doses were administered at time zero shown in FIG. 23A. The curve with the data points represented as white circles represents the average of the glucose measurements from the OGTT testing of the same three dogs two to three weeks after hepatic denervation. As can be seen in FIG. 23A, the glucose values after hepatic denervation peaked at lower glucose concentrations and dropped much more rapidly than the glucose values prior to hepatic denervation. In accordance with several embodiments, the results of the study provide strong evidence of the efficacy of hepatic denervation for controlling blood glucose levels.

B. Example 2

Figure 23B:
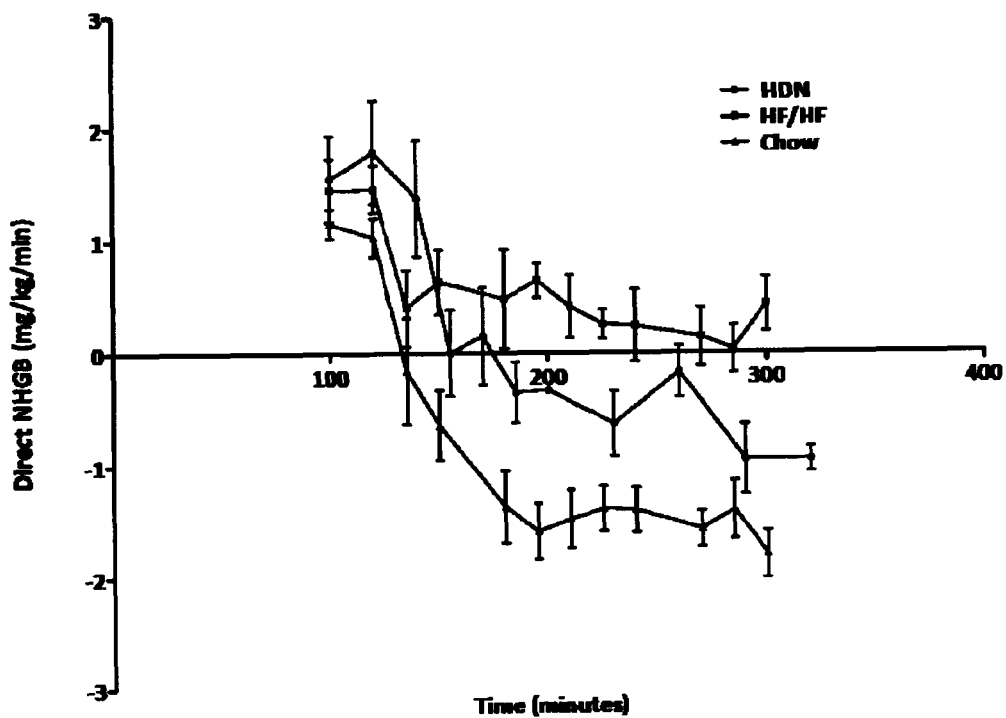

FIG. 23B illustrates the net hepatic glucose balanced obtained during a hyperglycemic-hyperinsulinemic clamp study. The data represented with circle indicators (HDN) represents the average net hepatic glucose levels of the same 3 dogs from Example 1 four weeks after denervation. The data represented with square indicators (HF/HF) represents the average net hepatic glucose levels of 5 dogs that were fed a high fat, high fructose diet. The data represented with the triangle indicators (Chow) represents the average net hepatic glucose levels of 5 dogs fed a normal diet. The data shows that toward the end of the curves, hepatic denervation restores net hepatic glucose balance to about 60% back to baseline, which suggests insulin resistance in the liver in the HF/HF dog model is largely corrected by hepatic denervation, and which indicates that hepatic denervation has an effect on hepatic glucose uptake and/or hepatic glucose production.

C. Example 3

A hepatic artery was harvested from a porcine liver as far proximal as the common hepatic artery and as far distal as the bifurcation of the left hepatic artery and the right hepatic artery. The arterial plexus was sandwiched between two sections of liver parenchyma (a "bed" and a "roof"), and placed in a stainless steel tray to serve as a return electrode. A total of 3 arteries were ablated using a RADIONICS RFG-3C RF generator using a NiTi/dilator sheath, having an exposed surface of approximately 1/16" to 3/32" in length. RF energy was applied for 117 seconds in each case, with the generator power setting at 4 (generally delivering 2-3 W into 55-270Ω). For the first 2 sample arteries, a K-type thermocouple was used to monitor extravascular temperatures, which reached 50-63° C. The first ablation was performed in the left hepatic artery, the second ablation was performed in the right hepatic artery, and the third ablation was performed in the proper hepatic artery. For the first ablation in the left hepatic artery having a lumen diameter of 1.15 mm, two ablation zone measurements were obtained (0.57 mm and 0.14 mm). A roughly 3 mm coagulation zone was measured. The electrode exposure distance was 3/32". For the second ablation in the right hepatic artery, an electrode exposure distance of 1/16" was used. The generator impeded out due to high current density and no ablation lesion was observed. For the third ablation of the proper hepatic artery having a lumen diameter of 2 mm and using an electrode exposure distance was 3/32", three ablation zone widths of 0.52 mm, 0.38 mm and 0.43 mm were measured. The measured ablation zone widths support the fact that nerves surrounding the proper hepatic artery (which may be tightly adhered to or within the arterial wall) can be denervated using an intravascular approach. Histological measurements of porcine hepatic artery segments have indicated that hepatic artery nerves are within 1-10 medial thicknesses (approximately 1-3 mm) from the lumen surface, thereby providing support for modulation (e.g., denervation, ablation, blocking conduction of, or disruption) of nerves innervating branches of the hepatic artery endovascularly using low-power RF energy (e.g., less than 10 W and/or less than 1 kJ) or other energy modalities. Nerves innervating the renal artery are generally within the 4-6 mm range from the lumen of the renal artery.

D. Example 4

An acute animal lab was performed on a common hepatic artery and a proper hepatic artery of a porcine model. The common hepatic artery was ablated 7 times and the proper hepatic artery was ablated 3 times. According to one embodiment of the invention, temperature-control algorithms (e.g., adjusting power manually to achieve a desired temperature) were implemented at temperatures ranging from 50° C. to 80° C. and for total ablation times ranging from 2 to 4 minutes. According to one embodiment of the invention, the electrode exposure distance for all of the ablations was 3/32". Across all ablations the ablation parameters generally ranges as follows, according to various embodiments of the invention: resistance ranged from about 0.1 ohms to about 869 ohms (generally about 100 ohms to about 300 ohms), power output ranged from about 0.1 W to about 100 W (generally about 1 Watt to about 10 Watts), generator voltage generally ranged from about 0.1 V to about 50 V, current generally ranged from about 0.01 A to about 0.5 A, and electrode tip temperature generally ranged from about 37° C. to about 99° C. (generally +/−5° C. from the target temperature of each ablation). Energy was titrated on the basis of temperature and time up to approximately 1 kJ or more in many ablations. Notching was observed under fluoroscopy in locations corresponding to completed ablations, which may be a positive indicator of ablative success, as the thermal damage caused arterial spasm.

It was observed that, although separation of ablation regions by 1 cm was attempted, the ablation catheter skipped distally during the ablation procedure, which is believed to have occurred due to the movement of the diaphragm during the ablation procedure, thereby causing movement of the anatomy and hepatic arterial vasculature surrounding the liver (which may be a unique challenge for the liver anatomy).

Unlike previous targets for endovascular ablation (e.g., renal arteries, which course generally straight toward the kidneys), the hepatic arterial vasculature is highly variable and tortuous. It was observed during the study that catheters having a singular articulated shape may not be able to provide adequate and consistent electrode contact force to achieve ablative success. For example, in several ablation attempts using an existing commercially-available RF ablation catheter, with energy delivered according to a manually-implemented constant-temperature algorithm, the power level was relatively high with low variability in voltage output required to maintain the target temperature. This data is generally indicative of poor vessel wall contact, as the electrode is exposed to higher levels of cooling from the blood (thereby requiring higher power output to maintain a particular target temperature). Additionally, tissue resistivity is a function of temperature. Although the tissue within the vessel wall is spatially fixed, there is constant mass flux of "refreshed" blood tissue in contact with the electrode at physiologic temperatures. Consequently, in one embodiment, when the electrode is substantially in contact with "refreshed" blood at physiologic temperatures, the electrode "sees" substantially constant impedance. Due to the correlation between impedance and voltage (e.g., $P=V^2/R$), the substantially constant impedance is reflected in a substantially constant (less variable) voltage input required to maintain a target electrode tip temperature. Therefore, particular embodiments (such as those described, for example, in FIGS. 14 and 15 advantageously enable adequate electrode contact in any degree of hepatic artery tortuosity that may be encountered clinically.

E. Example 5

A numerical model representing the hepatic artery and surrounding structures was constructed in COMSOL Multiphysics 4.3. using anatomical, thermal, and electrical tissue properties. Thermal and electrical properties are a function of temperature. Electrical conductivity (sigma, or σ) generally varies according to the equation $\sigma = \sigma_0 e^{0.015(T-T_0)}$, where $\sigma_0$ is the electrical conductivity measured at physiologic temperatures ($T_0$) and T is temperature. With reference to FIGS. 22A-22D, model geometry was assessed and included regions representing the hepatic artery lumen, bile duct 2205, and portal vein 2210. The bile 2205 duct and portal vein 2210 were modeled as grounded structures, highlighting the effect of these structures on current flow. By calculating liver blood flow and the relative contributions from the hepatic artery and portal vein 2210, we determined the flow in the hepatic artery was significantly lower than flow rates in other arteries (e.g., renal arteries). In one embodiment, the estimated flow rate was 139.5 mL/min. for the hepatic artery. Using the model described above, independent solutions were first obtained for monopolar and bipolar electrode configuration. A geometric model corresponding to the common hepatic artery was created and a time-dependent solution was calculated in COMSOL using the bioheat equation, $\rho_b c_{pb} \partial T/\partial t = \nabla(k \nabla T_t) + \rho_b u c_{pb}(T_B - T) + q_m$, which, in one embodiment, relates the temperature at any point in the model as a function of the temperature gradient in the tissue, blood perfusion, blood temperature entering the geometric region of interest, and the heat generated ($q_m$) as a function of RF energy deposition.

Figure 22A:
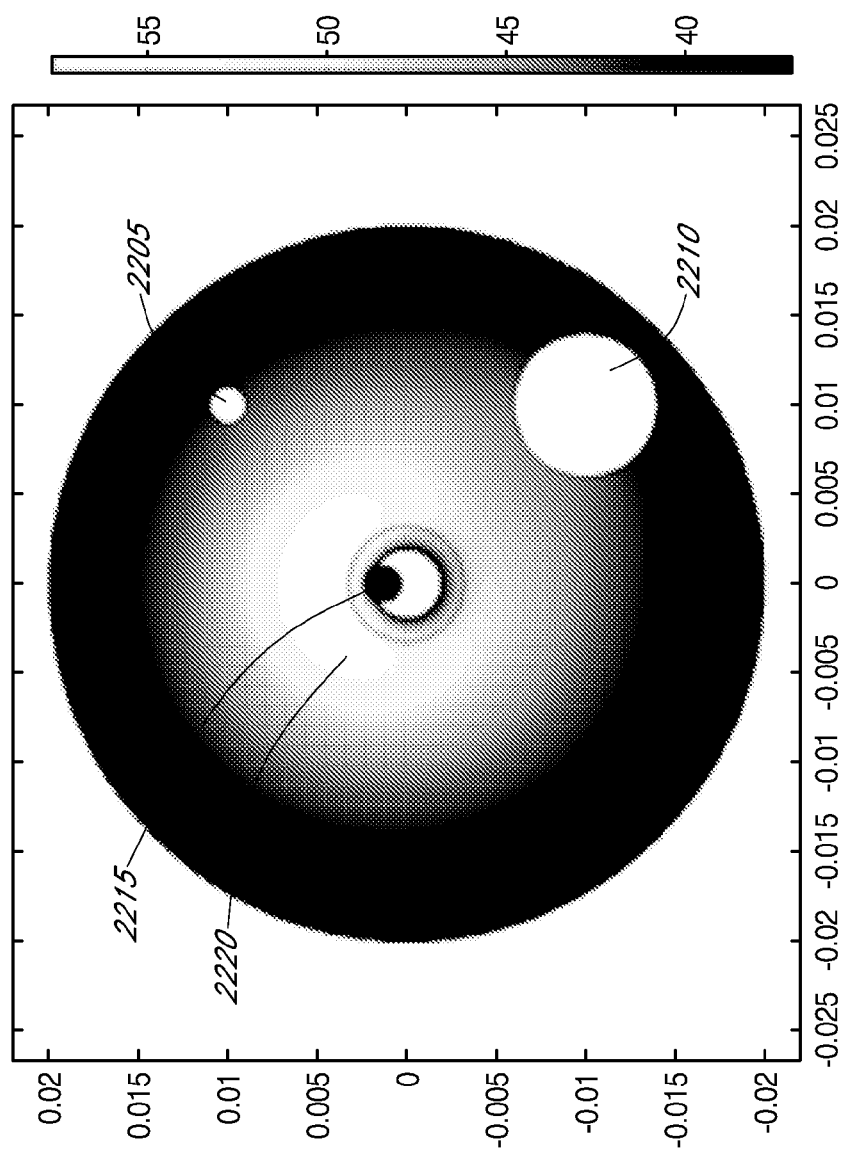
FIGS. 22A-22D illustrate geometric models.
Figure 22B:
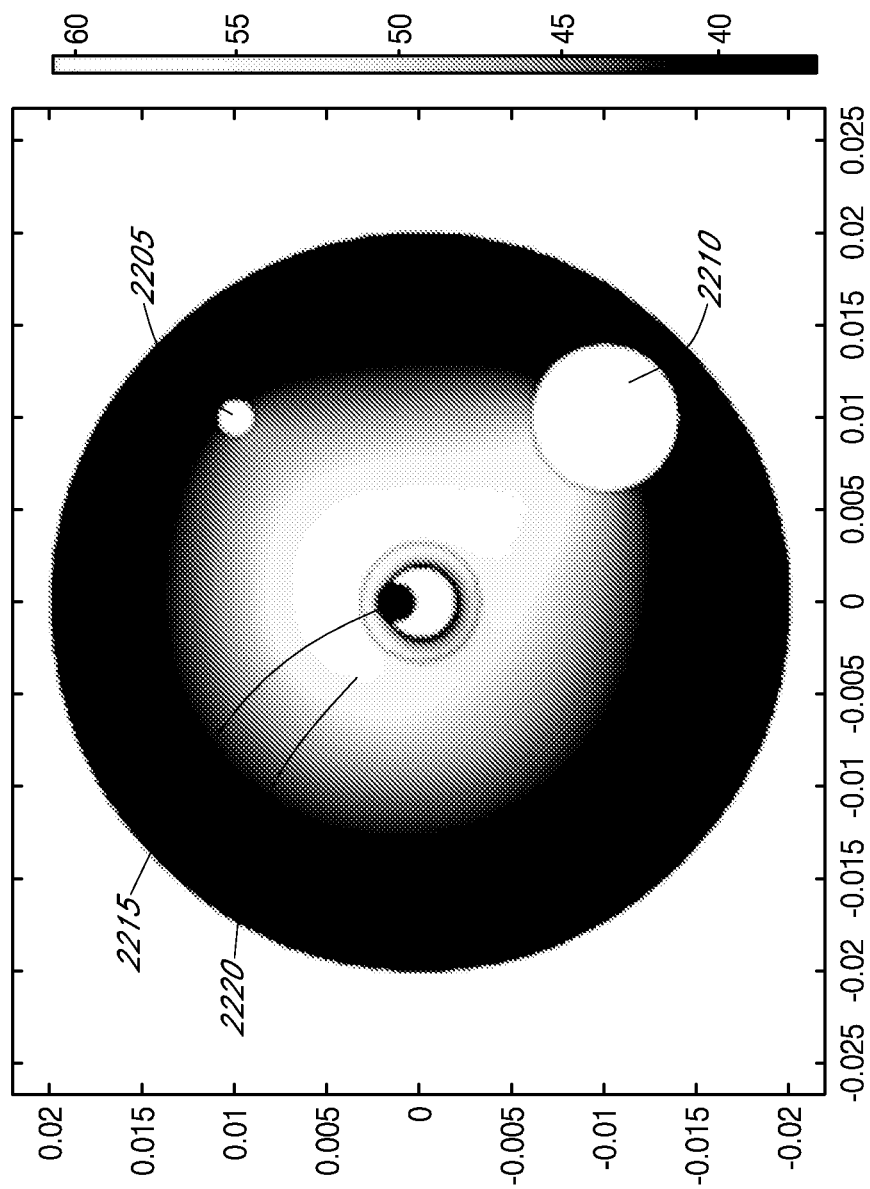
Figure 22C:
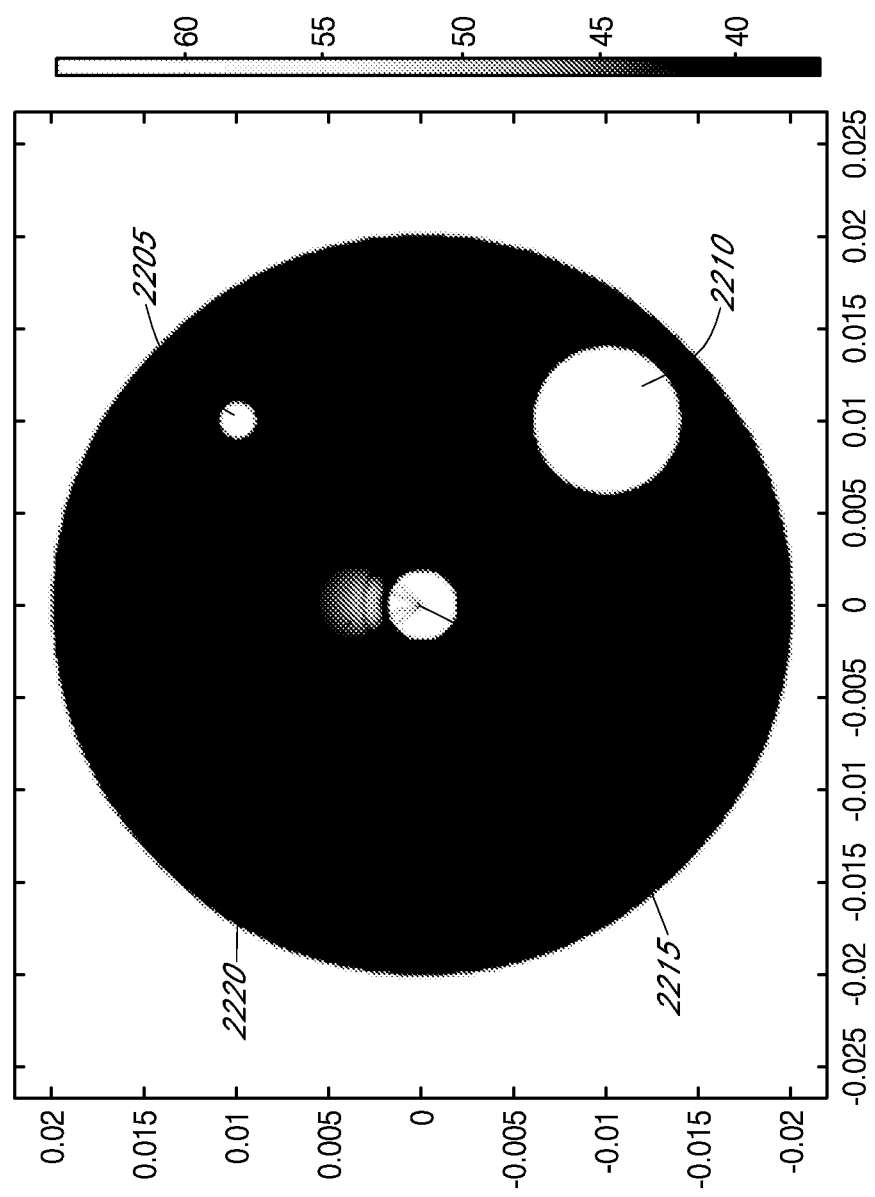
Figure 22D:
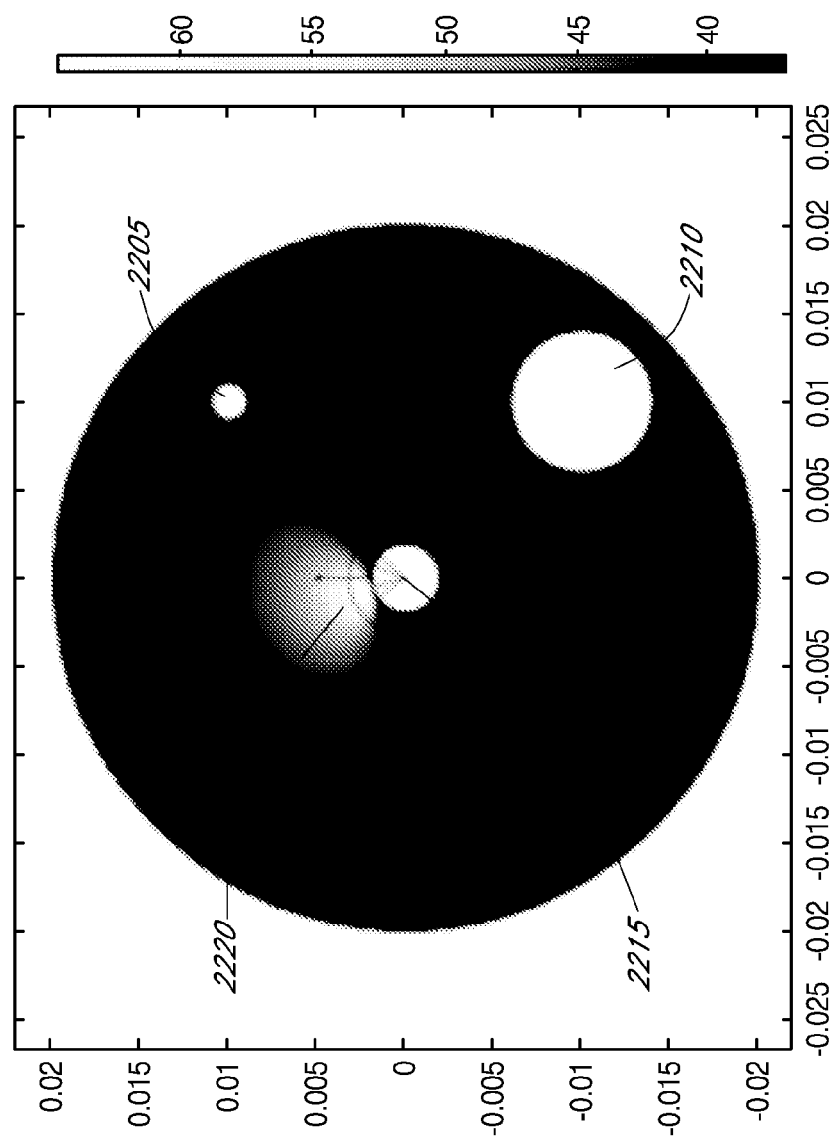

FIGS. 22A and 22B illustrate a geometric model of RF energy deposition in the common hepatic artery using a single electrode, with the conductivity of the bile duct 2205 and the portal vein 2210 grounded (FIG. 22A) and accounted for (FIG. 22B). As shown in FIG. 22B, biliary and portal vein conductivity can influence where ablation energy travels when a single electrode 2215 is used. FIGS. 22C and 22D illustrate a geometric model of RF energy deposition in the common hepatic artery for a bipolar electrode configuration 2215, with the conductivity of the bile duct 2205 and the portal vein 2210 grounded (FIG. 22C) and accounted for (FIG. 22D).

The shape of the electric field and resulting thermal ablation 2220 was significantly affected in the monopolar ablation model due to biliary and portal vein conductivity (as shown in FIGS. 22A and 22B). Minimal effects due to biliary and portal vein conductivity (e.g., shaping effects) were observed in the shape of the electric field and resulting thermal ablation 2220 for the bipolar ablation model (shown in FIGS. 22C and 22D). FIGS. 22A and 22B were obtained when the pair of bipolar electrodes were modeled, according to one embodiment, as disposed at a location that is substantially tangent to the inner lumen of the artery, with each individual electrode having an arc length of 20 degrees and with an inter-electrode spacing of 10 degrees. In one embodiment, the edges of the electrodes have radii sufficient to reduce current concentrations (less than 0.001"). In several embodiments, the bipolar configuration advantageously provides effective ablation (e.g., thermal ablation of the hepatic artery) without significant effect on shaping of the ablation zone, despite the effects of biliary and portal vein conductivity due to proximity of the bile duct and portal vein to the common hepatic artery.

F. Example 6

Independent modeling solutions were obtained for an ablation with convective cooling (e.g., provided by blood flow alone) and for an ablation incorporating active cooling (e.g., 7° C. coolant) using the same bipolar configuration model described above in Example 5. The models showed significantly decreased temperatures at the location corresponding to the lumen (endothelial) interface. Higher power (45% higher power) was delivered to the active cooling model. Even with higher power delivered (e.g., 45% higher power) to the active cooling model, the endothelial region of the common hepatic artery remained cool (e.g. less than hyperthermic temperatures up to 1 mm from the lumen). The effective shaping of the thermal ablation zone was also directed into a more linear shape directed radially in the active cooling model. It was observed, that, in accordance with several embodiments, as cooling power is increased and RF power is increased, the linear shaping effect was magnified, thereby rendering the ablation zone capable of being directed or "programmed" (e.g., toward a more targeted location).

In some embodiments, the neuromodulation catheter (e.g., ablation catheter) designs described herein (e.g., the balloon catheters of FIGS. 13A-13C) advantageously provide effective modulation of nerves innervating branches of the hepatic artery without causing, or at least minimizing endothelial damage, if desired. For example, the catheters described herein can occlude the hepatic artery (e.g., using a balloon) and then circulate coolant in the region of the ablation (e.g., within the lumen of the balloon). In some embodiments, the catheters provide the unique advantage of both higher power net energy offered through larger electrode surface area (which may be enabled by the larger electrode sizes that can be manufactured on a balloon) and increased deposition time (which may be permitted by the ability to occlude flow to the hepatic artery for longer periods of time). In accordance with several embodiments, the increase in energy density through higher power mitigates the risk of damage to the endothelial wall by the flow of coolant within the balloon.

While the devices, systems and methods described herein have primarily addressed the treatment of diabetes (e.g., diabetes mellitus), other conditions, diseases, disorders, or syndromes can be treated using the devices, systems and methods described herein, including but not limited to ventricular tachycardia, atrial fibrillation or atrial flutter, inflammatory diseases, endocrine diseases, hepatitis, pancreatitis, gastric ulcers, gastric motility disorders, irritable bowel syndrome, autoimmune disorders (such as Crohn's disease), obesity, Tay-Sachs disease, Wilson's disease, NASH, NAFLD, leukodystrophy, polycystic ovary syndrome, gestational diabetes, diabetes insipidus, thyroid disease, and other metabolic disorders, diseases, or conditions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above.

What is claimed is:

1. A method for thermally-induced hepatic neuromodulation to decrease blood glucose levels within a subject, comprising:
    identifying a subject having a metabolic disorder,
    inserting a radiofrequency (RF) ablation catheter into vasculature of said subject;
    advancing the RF ablation catheter to a location within a common hepatic artery of the vasculature;

wherein the location is within the common hepatic artery between a branch of the celiac artery and a branch of the common hepatic artery; and using the RF ablation catheter to intravascularly deliver a therapeutically effective amount of RF energy to an inner wall of the common hepatic artery to ablate one or more sympathetic nerves of a hepatic plexus, thereby decreasing blood glucose levels within the subject, wherein the RF ablation catheter comprises two electrodes, and wherein the RF ablation catheter is configured to maintain sufficient contact pressure of at least one of said electrodes against the inner wall of the common hepatic artery while the RF energy is being delivered, wherein the RF energy is caused to be delivered to an anterior 180° arc of the inner wall of the common hepatic artery, thereby ablating sympathetic nerves without ablating parasympathetic nerves.

2. The method of claim 1, wherein the ablation catheter comprises a balloon catheter configured to maintain the sufficient contact pressure of the at least one electrode against the inner wall of the common hepatic artery.

3. The method of claim 1, wherein the ablation catheter comprises a steerable distal tip configured to maintain the sufficient contact pressure of the at least one electrode against the inner wall of the common hepatic artery.

4. The method of claim 1, wherein the sufficient contact pressure is between about 5 g/mm$^2$ and about 100 g/mm$^2$.

5. The method of claim 1, wherein the sufficient contact pressure is between about 0.1 g/mm$^2$ and about 10 g/mm$^2$.

6. The method of claim 1, wherein the therapeutically effective amount of RF energy is in the range of between about 100 J and about 1 kJ.

7. The method of claim 1, wherein the therapeutically effective amount of RF energy has a power level between about 0.1 W and about 10 W.

8. The method of claim 1, wherein the RF energy has a power level between about 3 W and about 8 W.

9. The method of claim 1, further comprising providing cooling to a portion of the common hepatic artery that is not being targeted by the RF energy.

10. A method for thermally-induced hepatic neuromodulation to decrease blood glucose levels within a subject, comprising:
    delivering a radiofrequency (RF) ablation catheter to a vicinity of a hepatic plexus within a hepatic artery branch, the RF ablation catheter comprising two electrodes;
    positioning at least one of the two electrodes in contact with an inner wall of the hepatic artery branch; and
    disrupting neural communication of sympathetic nerves of the hepatic plexus surrounding the hepatic artery branch by applying an electrical signal to the at least one electrode, thereby causing thermal energy to be delivered by the at least one electrode to heat the inner wall of the hepatic artery branch,
    wherein disrupting neural communication comprises permanently disabling neural communication of sympathetic nerves of the hepatic plexus.

11. The method of claim 10, wherein the hepatic artery branch is the proper hepatic artery.

12. The method of claim 10, wherein the hepatic artery branch is the common hepatic artery.

13. The method of claim 10, further comprising providing cooling to a portion of the hepatic artery branch that is not being targeted by the energy.

14. The method of claim 10, wherein the catheter is configured to maintain contact pressure against the inner wall of the hepatic artery branch.

15. The method of claim 14, wherein the contact pressure is between about 5 g/mm$^2$ and about 100 g/mm$^2$.

16. The method of claim 14, wherein the contact pressure is between about 0.1 g/mm$^2$ and about 10 g/mm$^2$.

17. The method of claim 10, wherein the energy is in the range of between about 100 J and about 1 kJ.

18. The method of claim 10, wherein the energy has a power level between about 0.1 W and about 10 W.

19. The method of claim 10, wherein the energy has a power level between about 3 W and about 8 W.

20. A method for thermally-induced hepatic neuromodulation to decrease blood glucose levels within a subject, comprising:
    delivering a radiofrequency (RF) ablation catheter to a vicinity of a hepatic plexus within a hepatic artery branch, the RF ablation catheter comprising two electrodes;
    positioning at least one of the two electrodes in contact with an inner wall of the hepatic artery branch; and
    disrupting neural communication of sympathetic nerves of the hepatic plexus surrounding the hepatic artery branch by applying an electrical signal to the at least one electrode, thereby causing thermal energy to be delivered by the at least one electrode to heat the inner wall of the hepatic artery branch,
    wherein disrupting neural communication comprises temporarily inhibiting or reducing neural communication of sympathetic nerves of the hepatic plexus.

21. The method of claim 20, wherein the hepatic artery branch is the proper hepatic artery.

22. The method of claim 20, wherein the hepatic artery branch is the common hepatic artery.

23. The method of claim 20, further comprising providing cooling to a portion of the hepatic artery branch that is not being targeted by the energy.

24. The method of claim 20, wherein the catheter is configured to maintain contact pressure against the inner wall of the hepatic artery branch.

25. The method of claim 24, wherein the contact pressure is between about 5 g/mm$^2$ and about 100 g/mm$^2$.

26. The method of claim 24, wherein the contact pressure is between about 0.1 g/mm$^2$ and about 10 g/mm$^2$.

27. The method of claim 20, wherein the energy is in the range of between about 100 J and about 1 kJ.

28. The method of claim 20, wherein the energy has a power level between about 0.1 W and about 10 W.

29. The method of claim 20, wherein the energy has a power level between about 3 W and about 8 W.

30. A method for thermally-induced hepatic neuromodulation to decrease blood glucose levels within a subject, comprising:
    delivering a radiofrequency (RF) ablation catheter to a vicinity of a hepatic plexus within a hepatic artery branch, the RF ablation catheter comprising two electrodes;
    positioning at least one of the two electrodes in contact with an inner wall of the hepatic artery branch;
    disrupting neural communication of sympathetic nerves of the hepatic plexus surrounding the hepatic artery branch by applying an electrical signal to the at least one electrode, thereby causing thermal energy to be delivered by the at least one electrode to heat the inner wall of the hepatic artery branch; and positioning the RF ablation catheter in the vicinity of the celiac plexus of the subject and disrupting neural communication of sympathetic nerves of the celiac plexus by causing RF energy to be emitted from the at least one electrode of the RF ablation catheter.

31. The method of claim 30, wherein the hepatic artery branch is the proper hepatic artery.

32. The method of claim 30, wherein the hepatic artery branch is the common hepatic artery.

33. The method of claim 30, further comprising providing cooling to a portion of the hepatic artery branch that is not being targeted by the energy.

34. The method of claim 30, wherein the catheter is configured to maintain contact pressure against the inner wall of the hepatic artery branch.

35. The method of claim 34, wherein the contact pressure is between about 5 g/mm$^2$ and about 100 g/mm$^2$.

36. The method of claim 34, wherein the contact pressure is between about 0.1 g/mm$^2$ and about 10 g/mm$^2$.

37. The method of claim 30, wherein the energy is in the range of between about 100 J and about 1 kJ.

38. The method of claim 30, wherein the energy has a power level between about 0.1 W and about 10 W.

39. A method for thermally-induced hepatic neuromodulation to decrease blood glucose levels within a subject, comprising:
delivering a neuromodulation catheter within a hepatic artery to a vicinity of a hepatic plexus of a subject; and
modulating nerves of the hepatic plexus by using said catheter to deliver energy to the hepatic plexus sufficient to modulate one or more nerves within the hepatic plexus to decrease at least one of blood glucose levels or triglyceride levels in said subject,
wherein modulating the nerves of the hepatic plexus comprises denervating sympathetic nerves of the hepatic plexus without denervating parasympathetic nerves of the hepatic plexus.

40. The method of claim 30, wherein the energy has a power level between about 3 W and about 8 W.

41. The method of claim 39, wherein the hepatic artery is the proper hepatic artery.

42. The method of claim 39, wherein the hepatic artery is the common hepatic artery.

43. The method of claim 39, further comprising providing cooling to a portion of the hepatic artery that is not being targeted by the energy.

44. The method of claim 39, wherein the catheter is configured to maintain contact pressure against an inner wall of the hepatic artery.

45. The method of claim 44, wherein the contact pressure is between about 5 g/mm$^2$ and about 100 g/mm$^2$.

46. The method of claim 44, wherein the contact pressure is between about 0.1 g/mm$^2$ and about 10 g/mm$^2$.

47. The method of claim 39, wherein the energy is in the range of between about 100 J and about 1 kJ.

48. The method of claim 39, wherein the energy has a power level between about 0.1 W and about 10 W.

49. The method of claim 39, wherein the energy has a power level between about 3 W and about 8 W.

50. A method for thermally-induced hepatic neuromodulation to decrease blood glucose levels within a subject, comprising:
delivering a neuromodulation catheter within a hepatic artery to a vicinity of a hepatic plexus of a subject; and
modulating nerves of the hepatic plexus by using said energy catheter to deliver energy to the hepatic plexus sufficient to modulate one or more nerves within the hepatic plexus to decrease at least one of blood glucose levels or triglyceride levels in said subject,
wherein modulating the nerves of the hepatic plexus comprises denervating sympathetic nerves of the hepatic plexus and stimulating parasympathetic nerves of the hepatic plexus.

51. The method of claim 50, wherein the hepatic artery is the proper hepatic artery.

52. The method of claim 50, wherein the hepatic artery is the common hepatic artery.

53. The method of claim 50, further comprising providing cooling to a portion of the hepatic artery that is not being targeted by the energy.

54. The method of claim 50, wherein the catheter is configured to maintain contact pressure against an inner wall of the hepatic artery.

55. The method of claim 54, wherein the contact pressure is between about 5 g/mm$^2$ and about 100 g/mm$^2$.

56. The method of claim 54, wherein the contact pressure is between about 0.1 g/mm$^2$ and about 10 g/mm$^2$.

57. The method of claim 50, wherein the energy is in the range of between about 100 J and about 1 kJ.

58. The method of claim 50, wherein the energy has a power level between about 0.1 W and about 10 W.

59. The method of claim 50, wherein the energy has a power level between about 3 W and about 8 W.

60. A method for thermally-induced hepatic neuromodulation to decrease blood glucose levels within a subject, comprising:
delivering a neuromodulation catheter within a hepatic artery to a vicinity of a hepatic plexus of a subject; and
modulating nerves of the hepatic plexus by using said energy catheter to deliver energy to the hepatic plexus sufficient to modulate one or more nerves within the hepatic plexus to decrease at least one of blood glucose levels or triglyceride levels in said subject,
wherein the energy delivered comprises radiofrequency energy sufficient to denervate said one or more nerves.

61. The method of claim 60, wherein the hepatic artery is the proper hepatic artery.

62. The method of claim 60, wherein the hepatic artery is the common hepatic artery.

63. The method of claim 60, further comprising providing cooling to a portion of the hepatic artery that is not being targeted by the energy.

64. The method of claim 60, wherein the catheter is configured to maintain contact pressure against an inner wall of the hepatic artery.

65. The method of claim 64, wherein the contact pressure is between about 5 g/mm$^2$ and about 100 g/mm$^2$.

66. The method of claim 64, wherein the contact pressure is between about 0.1 g/mm$^2$ and about 10 g/mm$^2$.

67. The method of claim 60, wherein the energy is in the range of between about 100 J and about 1 kJ.

68. The method of claim 60, wherein the energy has a power level between about 0.1 W and about 10 W.

69. The method of claim 60, wherein the energy has a power level between about 3 W and about 8 W.

* * * * *

UNITED STATES PATENT AND TRADEMARK OFFICE
CERTIFICATE OF CORRECTION

PATENT NO. : 8,568,399 B2  
APPLICATION NO. : 13/789521  
DATED : October 29, 2013  
INVENTOR(S) : Azamian et al.

Page 1 of 1

It is certified that error appears in the above-identified patent and that said Letters Patent is hereby corrected as shown below:

In the Specification

In column 45 at line 32, Change "10^1" to --10^3--.

In the Claims

In column 63 at line 1, In Claim 30, change the second instance of "the" at the end of line 1 to --a--.

In column 64 at line 2, In Claim 50, before "catheter" delete "energy".

In column 64 at line 38, In Claim 60, before "catheter" delete "energy".

Signed and Sealed this
Twenty-first Day of October, 2014

Michelle K. Lee
*Deputy Director of the United States Patent and Trademark Office*